US011591570B2

(12) United States Patent
Bhat et al.

(10) Patent No.: US 11,591,570 B2
(45) Date of Patent: Feb. 28, 2023

(54) RECOMBINANT CARDIOMYOCYTES AND CARDIOMYOCYTE CELL LINES EXPRESSING HERG

(71) Applicant: The Governors of the University of Alberta, Edmonton (CA)

(72) Inventors: Rakesh Bhat, Edmonton (CA); Michael Houghton, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 667 days.

(21) Appl. No.: 16/333,549

(22) PCT Filed: Sep. 13, 2017

(86) PCT No.: PCT/CA2017/051076
§ 371 (c)(1),
(2) Date: Mar. 14, 2019

(87) PCT Pub. No.: WO2018/049519
PCT Pub. Date: Mar. 22, 2018

(65) Prior Publication Data
US 2020/0181577 A1    Jun. 11, 2020

Related U.S. Application Data

(60) Provisional application No. 62/395,371, filed on Sep. 15, 2016.

(51) Int. Cl.
| | | |
|---|---|---|
| C12N 15/63 | (2006.01) | |
| C12N 15/79 | (2006.01) | |
| A61K 48/00 | (2006.01) | |
| C07H 21/04 | (2006.01) | |
| C12N 5/077 | (2010.01) | |
| C07K 14/705 | (2006.01) | |
| C12N 15/86 | (2006.01) | |
| G01N 27/26 | (2006.01) | |
| G01N 33/50 | (2006.01) | |
| G01N 33/68 | (2006.01) | |

(52) U.S. Cl.
CPC .......... *C12N 5/0657* (2013.01); *C07K 14/705* (2013.01); *C12N 15/86* (2013.01); *G01N 27/26* (2013.01); *G01N 33/5061* (2013.01); *C07H 21/04* (2013.01); *C12N 15/63* (2013.01); *C12N 2503/02* (2013.01); *C12N 2510/00* (2013.01); *G01N 33/6872* (2013.01)

(58) Field of Classification Search
CPC ........ C12N 15/63; C12N 15/85; C12N 15/86; C12N 2510/00; C07H 21/04
See application file for complete search history.

(56) References Cited

U.S. PATENT DOCUMENTS

2015/0193575 A1    7/2015  Houghton et al.

FOREIGN PATENT DOCUMENTS

| | | |
|---|---|---|
| WO | 2000006772 A1 | 10/2000 |
| WO | 2009108905 A2 | 3/2009 |
| WO | 2015085432 A1 | 6/2015 |

OTHER PUBLICATIONS

Houghton et al., 2015, US 20150193575 A1.*
Lin et al., 2010, Am J Physiol Heart Circ Physiol, vol. 298, p. H1842-H1849.*
Li et al., 2008, US 20080090984 A1.*
Owman et al., 2004, US 20040019109 A1.*
Robertson et al., 2005, Geneseq Accession No. AEA04319, computer printout, pp. 1-4.*
Bhat et al., 2018, "A human cardiomyocyte cell-line expressing hERG: An improved system for testing drug-associated hERG blocking and cardiotoxicity," Journal of Pharmacological and Toxicological Methods, 93:114, abstract.
Fleury et al., 2003, "Multiply attenuated, self-inactivating lentiviral vectors efficiently deliver and express genes for extended periods of time in adult rat cardiomyocytes in vivo," Circulation, 107(18):2375-2382.
Haraguchi et al., 2015, "Electrophysiological analysis of mammalian cells expressing hERG using automated 384-well-patch-clamp," BMC Pharmacol Toxicol., 16:39 (6 pages).
Hoppe et al., 2001, "Distinct gene-specific mechanisms of arrhythmia revealed by cardiac gene transfer of two long QT disease genes, HERG and KCNE1," Proc Natl Acad Sci USA, 98(9):5335-5340.
Hua et al., 2004, "Suppression of electrical alternans by overexpression of HERG in canine ventricular myocytes," Am J Physiol Heart Circ Physiol., 286(6):H2342-2352.
Liu et al., 2015, "Eag Domains regulate LQT Mutant hERG Channels in Human Induced Pluripotent Stem Cell-Derived Cardiomyocytes," PLoS One, 10(29): e0123951, 15 pages.
Matrai et al., 2010, "Recent advances in lentiviral vector development and applications," Mol Ther., 18(3):477-490.
Matsa et al., 2014, "Allele-specific RNA interference rescues the long-QT cardiomyocytes," European Heart Journal, 35:1078-1087.
Xue et al., 2009, "Stable overexpression of human metallothionein-IIA in a heart-derived cell line confers oxidative protection," Toxicol Lett., 188(1)70-76.

\* cited by examiner

*Primary Examiner* — Shin Lin Chen
(74) *Attorney, Agent, or Firm* — Jones Day

(57) ABSTRACT

Provided herein are recombinant cardiomyocytes and cardiomyocyte cell lines expressing human Ether-a-go-go Related Gene (hERG) potassium ion channel, including, for example, stable cell lines, that comprise a transfected or transduced nucleic acid sequence encoding hERG. Also provided herein are methods of using the recombinant cardiomyocytes and cardiomyocyte cell lines expressing hERG for screening compounds for cardiotoxicity, including methods for determining the activity of compounds to inhibit hERG.

9 Claims, 20 Drawing Sheets

Specification includes a Sequence Listing.

SEQ ID NO: 1

```
Met Pro Val Arg Arg Gly His Val Ala Pro Gln Asn Thr Phe Leu Asp
Thr Ile Ile Arg Lys Phe Glu Gly Gln Ser Arg Lys Phe Ile Ile Ala
Asn Ala Arg Val Glu Asn Cys Ala Val Ile Tyr Cys Asn Asp Gly Phe
Cys Glu Leu Cys Gly Tyr Ser Arg Ala Glu Val Met Gln Arg Pro Cys
Thr Cys Asp Phe Leu His Gly Pro Arg Thr Gln Arg Arg Ala Ala Ala
Gln Ile Ala Gln Ala Leu Leu Gly Ala Glu Glu Arg Lys Val Glu Ile
Ala Phe Tyr Arg Lys Asp Gly Ser Cys Phe Leu Cys Leu Val Asp Val
Val Pro Val Lys Asn Glu Asp Gly Ala Val Ile Met Phe Ile Leu Asn
Phe Glu Val Val Met Glu Lys Asp Met Val Gly Ser Pro Ala His Asp
Thr Asn His Arg Gly Pro Pro Thr Ser Trp Leu Ala Pro Gly Arg Ala
Lys Thr Phe Arg Leu Lys Leu Pro Ala Leu Leu Ala Leu Thr Ala Arg
Glu Ser Ser Val Arg Ser Gly Gly Ala Gly Gly Ala Gly Ala Pro Gly
Ala Val Val Val Asp Val Asp Leu Thr Pro Ala Ala Pro Ser Ser Glu
Ser Leu Ala Leu Asp Glu Val Thr Ala Met Asp Asn His Val Ala Gly
Leu Gly Pro Ala Glu Glu Arg Arg Ala Leu Val Gly Pro Gly Ser Pro
Pro Arg Ser Ala Pro Gly Gln Leu Pro Ser Pro Arg Ala His Ser Leu
Asn Pro Asp Ala Ser Gly Ser Ser Cys Ser Leu Ala Arg Thr Arg Ser
Arg Glu Ser Cys Ala Ser Val Arg Arg Ala Ser Ser Ala Asp Asp Ile
Glu Ala Met Arg Ala Gly Val Leu Pro Pro Pro Arg His Ala Ser
Thr Gly Ala Met His Pro Leu Arg Ser Gly Leu Leu Asn Ser Thr Ser
Asp Ser Asp Leu Val Arg Tyr Arg Thr Ile Ser Lys Ile Pro Gln Ile
Thr Leu Asn Phe Val Asp Leu Lys Gly Asp Pro Phe Leu Ala Ser Pro
Thr Ser Asp Arg Glu Ile Ile Ala Pro Lys Ile Lys Glu Arg Thr His
Asn Val Thr Glu Lys Val Thr Gln Val Leu Ser Leu Gly Ala Asp Val
Leu Pro Glu Tyr Lys Leu Gln Ala Pro Arg Ile His Arg Trp Thr Ile
Leu His Tyr Ser Pro Phe Lys Ala Val Trp Asp Trp Leu Ile Leu Leu
Leu Val Ile Tyr Thr Ala Val Phe Thr Pro Tyr Ser Ala Ala Phe Leu
Leu Lys Glu Thr Glu Glu Gly Pro Pro Ala Thr Glu Cys Gly Tyr Ala
Cys Gln Pro Leu Ala Val Val Asp Leu Ile Val Asp Ile Met Phe Ile
Val Asp Ile Leu Ile Asn Phe Arg Thr Thr Tyr Val Asn Ala Asn Glu
Glu Val Val Ser His Pro Gly Arg Ile Ala Val His Tyr Phe Lys Gly
Trp Phe Leu Ile Asp Met Val Ala Ala Ile Pro Phe Asp Leu Leu Ile
Phe Gly Ser Gly Ser Glu Glu Leu Ile Gly Leu Leu Lys Thr Ala Arg
Leu Leu Arg Leu Val Arg Val Ala Arg Lys Leu Asp Arg Tyr Ser Glu
Tyr Gly Ala Ala Val Leu Phe Leu Leu Met Cys Thr Phe Ala Leu Ile
Ala His Trp Leu Ala Cys Ile Trp Tyr Ala Ile Gly Asn Met Glu Gln
Pro His Met Asp Ser Arg Ile Gly Trp Leu His Asn Leu Gly Asp Gln
```

FIGURE 2

```
Ile Gly Lys Pro Tyr Asn Ser Ser Gly Leu Gly Gly Pro Ser Ile Lys
Asp Lys Tyr Val Thr Ala Leu Tyr Phe Thr Phe Ser Ser Leu Thr Ser
Val Gly Phe Gly Asn Val Ser Pro Asn Thr Asn Ser Glu Lys Ile Phe
Ser Ile Cys Val Met Leu Ile Gly Ser Leu Met Tyr Ala Ser Ile Phe
Gly Asn Val Ser Ala Ile Ile Gln Arg Leu Tyr Ser Gly Thr Ala Arg
Tyr His Thr Gln Met Leu Arg Val Arg Glu Phe Ile Arg Phe His Gln
Ile Pro Asn Pro Leu Arg Gln Arg Leu Glu Glu Tyr Phe Gln His Ala
Trp Ser Tyr Thr Asn Gly Ile Asp Met Asn Ala Val Leu Lys Gly Phe
Pro Glu Cys Leu Gln Ala Asp Ile Cys Leu His Leu Asn Arg Ser Leu
Leu Gln His Cys Lys Pro Phe Arg Gly Ala Thr Lys Gly Cys Leu Arg
Ala Leu Ala Met Lys Phe Lys Thr His His Ala Pro Pro Gly Asp Thr
Leu Val His Ala Gly Asp Leu Leu Thr Ala Leu Tyr Phe Ile Ser Arg
Gly Ser Ile Glu Ile Leu Arg Gly Asp Val Val Val Ala Ile Leu Gly
Lys Asn Asp Ile Phe Gly Glu Pro Leu Asn Leu Tyr Ala Arg Pro Gly
Lys Ser Asn Gly Asp Val Arg Ala Leu Thr Tyr Cys Asp Leu His Lys
Ile His Arg Asp Asp Leu Leu Glu Val Leu Asp Met Tyr Pro Glu Phe
Ser Asp His Phe Trp Ser Ser Leu Glu Ile Thr Phe Asn Leu Arg Asp
Thr Asn Met Ile Pro Gly Ser Pro Gly Ser Thr Glu Leu Glu Gly Gly
Phe Ser Arg Gln Arg Lys Arg Lys Leu Ser Phe Arg Arg Arg Thr Asp
Lys Asp Thr Glu Gln Pro Gly Glu Val Ser Ala Leu Gly Pro Gly Arg
Ala Gly Ala Gly Pro Ser Ser Arg Gly Arg Pro Gly Gly Pro Trp Gly
Glu Ser Pro Ser Ser Gly Pro Ser Ser Pro Glu Ser Ser Glu Asp Glu
Gly Pro Gly Arg Ser Ser Ser Pro Leu Arg Leu Val Pro Phe Ser Ser
Pro Arg Pro Pro Gly Glu Pro Pro Gly Gly Glu Pro Leu Met Glu Asp
Cys Glu Lys Ser Ser Asp Thr Cys Asn Pro Leu Ser Gly Ala Phe Ser
Gly Val Ser Asn Ile Phe Ser Phe Trp Gly Asp Ser Arg Gly Arg Gln
Tyr Gln Glu Leu Pro Arg Cys Pro Ala Pro Thr Pro Ser Leu Leu Asn
Ile Pro Leu Ser Ser Pro Gly Arg Arg Pro Arg Gly Asp Val Glu Ser
Arg Leu Asp Ala Leu Gln Arg Gln Leu Asn Arg Leu Glu Thr Arg Leu
Ser Ala Asp Met Ala Thr Val Leu Gln Leu Leu Gln Arg Gln Met Thr
Leu Val Pro Pro Ala Tyr Ser Ala Val Thr Thr Pro Gly Pro Gly Pro
Thr Ser Thr Ser Pro Leu Leu Pro Val Ser Pro Leu Pro Thr Leu Thr
Leu Asp Ser Leu Ser Gln Val Ser Gln Phe Met Ala Cys Glu Glu Leu
Pro Pro Gly Ala Pro Glu Leu Pro Gln Glu Gly Pro Thr Arg Arg Leu
Ser Leu Pro Gly Gln Leu Gly Ala Leu Thr Ser Gln Pro Leu His Arg
His Gly Ser Asp Pro Gly Ser Tyr Leu Glu Cys Gly Arg Asn Pro Ala
Phe Leu Tyr Lys Val Val Leu Glu Met Asp Tyr Lys Asp Asp Asp Asp
Lys
```

Underline: Linker
Bold: Flag tag

FIGURE 2 (Continued)

SEQ ID NO: 2
```
ATGCCGGTGC GGAGGGGCCA CGTCGCGCCG CAGAACACCT TCCTGGACAC
CATCATCCGC AAGTTTGAGG GCCAGAGCCG TAAGTTCATC ATCGCCAACG
CTCGGGTGGA GAACTGCGCC GTCATCTACT GCAACGACGG CTTCTGCGAG
CTGTGCGGCT ACTCGCGGGC CGAGGTGATG CAGCGACCCT GCACCTGCGA
CTTCCTGCAC GGGCCGCGCA CGCAGCGCCG CGCTGCCGCG CAGATCGCGC
AGGCACTGCT GGGCGCCGAG GAGCGCAAAG TGGAAATCGC CTTCTACCGG
AAAGATGGGA GCTGCTTCCT ATGTCTGGTG GATGTGGTGC CCGTGAAGAA
CGAGGATGGG GCTGTCATCA TGTTCATCCT CAATTTCGAG GTGGTGATGG
AGAAGGACAT GGTGGGGTCC CCGGCTCATG ACACCAACCA CCGGGGCCCC
CCCACCAGCT GGCTGGCCCC AGGCCGCGCC AAGACCTTCC GCCTGAAGCT
GCCCGCGCTG CTGGCGCTGA CGGCCCGGGA GTCGTCGGTG CGGTCGGGCG
GCGCGGGCGG CGCGGGCGCC CCGGGGGCCG TGGTGGTGGA CGTGGACCTG
ACGCCCGCGG CACCCAGCAG CGAGTCGCTG GCCCTGGACG AAGTGACAGC
CATGGACAAC CACGTGGCAG GGCTCGGGCC CGCGGAGGAG CGGCGTGCGC
TGGTGGGTCC CGGCTCTCCG CCCCGCAGCG CGCCTGGCCA GCTCCCATCG
CCCCGGGCGC ACAGCCTCAA CCCCGACGCC TCGGGCTCCA GCTGCAGCCT
GGCCCGGACG CGCTCCCGAG AAAGCTGCGC CAGCGTGCGC CGCGCCTCGT
CGGCCGACGA CATCGAGGCC ATGCGCGCCG GGGTGCTGCC CCCGCCACCG
CGCCACGCCA GCACCGGGGC CATGCACCCA CTGCGCAGCG GCTTGCTCAA
CTCCACCTCG GACTCCGACC TCGTGCGCTA CCGCACCATT AGCAAGATTC
CCCAAATCAC CCTCAACTTT GTGGACCTCA AGGGCGACCC CTTCTTGGCT
TCGCCCACCA GTGACCGTGA GATCATAGCA CCTAAGATAA AGGAGCGAAC
CCACAATGTC ACTGAGAAGG TCACCCAGGT CCTGTCCCTG GGCGCCGACG
TGCTGCCTGA GTACAAGCTG CAGGCACCGC GCATCCACCG CTGGACCATC
CTGCATTACA GCCCCTTCAA GGCCGTGTGG GACTGGCTCA TCCTGCTGCT
GGTCATCTAC ACGGCTGTCT TCACACCCTA CTCGGCTGCC TTCCTGCTGA
AGGAGACGGA AGAAGGCCCG CCTGCTACCG AGTGTGGCTA CGCCTGCCAG
CCGCTGGCTG TGGTGGACCT CATCGTGGAC ATCATGTTCA TTGTGGACAT
CCTCATCAAC TTCCGCACCA CCTACGTCAA TGCCAACGAG GAGGTGGTCA
GCCACCCCGG CCGCATCGCC GTCCACTACT TCAAGGGCTG GTTCCTCATC
GACATGGTGG CCGCCATCCC CTTCGACCTG CTCATCTTCG GCTCTGGCTC
TGAGGAGCTG ATCGGGCTGC TGAAGACTGC GCGGCTGCTG CGGCTGGTGC
GCGTGGCGCG GAAGCTGGAT CGCTACTCAG AGTACGGCGC GGCCGTGCTG
TTCTTGCTCA TGTGCACCTT TGCGCTCATC GCGCACTGGC TAGCCTGCAT
CTGGTACGCC ATCGGCAACA TGGAGCAGCC ACACATGGAC TCACGCATCG
GCTGGCTGCA CAACCTGGGC GACCAGATAG GCAAACCCTA CAACAGCAGC
GGCCTGGGCG GCCCCTCCAT CAAGGACAAG TATGTGACGG CGCTCTACTT
```

FIGURE 3

```
CACCTTCAGC AGCCTCACCA GTGTGGGCTT CGGCAACGTC TCTCCCAACA
CCAACTCAGA GAAGATCTTC TCCATCTGCG TCATGCTCAT TGGCTCCCTC
ATGTATGCTA GCATCTTCGG CAACGTGTCG GCCATCATCC AGCGGCTGTA
CTCGGGCACA GCCCGCTACC ACACACAGAT GCTGCGGGTG CGGGAGTTCA
TCCGCTTCCA CCAGATCCCC AATCCCTGC GCCAGCGCCT CGAGGAGTAC
TTCCAGCACG CCTGGTCCTA CACCAACGGC ATCGACATGA ACGCGGTGCT
GAAGGGCTTC CCTGAGTGCC TGCAGGCTGA CATCTGCCTG CACCTGAACC
GCTCACTGCT GCAGCACTGC AAACCCTTCC GAGGGGCCAC CAAGGGCTGC
CTTCGGGCCC TGGCCATGAA GTTCAAGACC ACACATGCAC CGCCAGGGGA
CACACTGGTG CATGCTGGGG ACCTGCTCAC CGCCCTGTAC TTCATCTCCC
GGGGCTCCAT CGAGATCCTG CGGGGCGACG TCGTCGTGGC CATCCTGGGG
AAGAATGACA TCTTTGGGGA GCCTCTGAAC CTGTATGCAA GGCCTGGCAA
GTCGAACGGG GATGTGCGGG CCCTCACCTA CTGTGACCTA CACAAGATCC
ATCGGGACGA CCTGCTGGAG GTGCTGGACA TGTACCCTGA GTTCTCCGAC
CACTTCTGGT CCAGCCTGGA GATCACCTTC AACCTGCGAG ATACCAACAT
GATCCCGGGC TCCCCCGGCA GTACGGAGTT AGAGGGTGGC TTCAGTCGGC
AACGCAAGCG CAAGTTGTCC TTCCGCAGGC GCACGGACAA GGACACGGAG
CAGCCAGGGG AGGTGTCGGC CTTGGGGCCG GGCCGGGCGG GGGCAGGGCC
GAGTAGCCGG GGCCGGCCGG GGGGCCGTG GGGGAGAGC CCGTCCAGTG
GCCCCTCCAG CCCTGAGAGC AGTGAGGATG AGGGCCCAGG CCGCAGCTCC
AGCCCCCTCC GCCTGGTGCC CTTCTCCAGC CCCAGGCCCC CCGGAGAGCC
GCCGGGTGGG GAGCCCCTGA TGGAGGACTG CGAGAAGAGC AGCGACACTT
GCAACCCCCT GTCAGGCGCC TTCTCAGGAG TGTCCAACAT TTTCAGCTTC
TGGGGGACA GTCGGGGCCG CCAGTACCAG GAGCTCCCTC GATGCCCCGC
CCCCACCCCC AGCCTCCTCA ACATCCCCCT CTCCAGCCCG GGTCGGCGGC
CCCGGGGCGA CGTGGAGAGC AGGCTGGATG CCCTCCAGCG CCAGCTCAAC
AGGCTGGAGA CCCGGCTGAG TGCAGACATG GCCACTGTCC TGCAGCTGCT
ACAGAGGCAG ATGACGCTGG TCCCGCCCGC CTACAGTGCT GTGACCACCC
CGGGGCCTGG CCCCACTTCC ACATCCCCGC TGTTGCCCGT CAGCCCCCTC
CCCACCCTCA CCTTGGACTC GCTTTCTCAG GTTTCCCAGT TCATGGCGTG
TGAGGAGCTG CCCCCGGGGG CCCCAGAGCT TCCCCAAGAA GGCCCCACAC
GACGCCTCTC CCTACCGGGC CAGCTGGGGG CCCTCACCTC CCAGCCCCTG
CACAGACACG GCTCGGACCC GGGCAGTTAC CTCGAGTGCG GCCGCAACCC
AGCTTTCTTG TACAAAGTGG TTCTCGAGAT GGACTACAAA GACGATGACG
ACAAGTA
```

Underscore: Linker
Underscore Gray = attB2 site
Bold: Flag tag
GTA at end of sequence : Stop codon

FIGURE 3 (Continued)

RECOMBINANT CARDIOMYOCYTES AND CARDIOMYOCYTE CELL LINES EXPRESSING HERG

This application is a U.S. National Stage filing under 35 U.S.C. § 371 of International Application No. PCT/CA2017/051076, filed Sep. 13, 2017, which claims the benefit of and priority to U.S. Provisional Application No. 62/395,371, filed Sep. 15, 2016, the entire content of each of which are incorporated by reference herein in their entirety.

1. TECHNICAL FIELD

The present disclosure relates generally to recombinant cardiomyocytes and cardiomyocyte cell lines expressing hERG and uses thereof.

2. BACKGROUND

Cardiotoxicity is a leading cause of attrition in clinical studies and post-marketing withdrawal. The human Ether-a-go-go Related Gene 1 (hERG1) $K^+$ ion channel is implicated in cardiotoxicity. Therefore, screening of candidate drugs for activity against cardiac ion channels, including hERG1, is recommended.

The hERG1 ion channel (also referred to as KCNH2 or Kv11.1) is a key element for the rapid component of the delayed rectified potassium currents ($I_{Kr}$) in cardiac myocytes, required for the normal repolarization phase of the cardiac action potential (Curran et al. (1995) *Cell* 80: 795-803; Tseng (2001) *J. Mol. Cell. Cardiol.* 33: 835-49; Vandenberg et al. (2001) *Trends. Pharm. Sci.* 22: 240-246). Loss of function mutations in hERG1 cause increased duration of ventricular repolarization, which leads to prolongation of the time interval between Q and T waves of the body surface electrocardiogram (long QT syndrome-LQTS) (Splawski et al. (2000) *Circulation* 102: 1178-1185; Witchel et al. (2000) *Clin. Exp. Pharmacol. Physiol.* 27: 753-766). LQTS leads to serious cardiovascular disorders, such as tachyarrhythmia and sudden cardiac death.

In vitro screening of candidate drugs for activity against the hERG cardiac ion channel have generally involved the use of non-cardiac cell lines (e.g., human embryonic kidney (HEK 293) cells and Chinese hamster ovary (CHO) cells; see, e.g., Haraguchi et al. (2015) *BMC Pharmacol Toxicol.* 16: 39) for the prediction of drug-induced ECG abnormalities. There remains a need for suitable cell lines derived from cardiac cells, for improved in vitro screening of compounds for drug discovery and/or drug development.

3. SUMMARY

The present disclosure provides novel recombinant cardiomyocytes and cardiomyocyte cell lines, and methods for their use, including for screening compounds for cardiotoxicity.

Provided herein are recombinant cardiomyocytes and cell lines, including stable cell lines, that comprise a transfected or transduced nucleic acid sequence encoding hERG. In some embodiments, hERG comprises an amino acid sequence (see, e.g, amino acids 1-1159) as set forth in SEQ ID NO: 1.

In some embodiments, the recombinant cardiomyocytes are designated hMYO-hERG. In some embodiments, the recombinant cardiomyocytes are transduced adult human ventricular cardiomyocytes. Exemplary cells include those deposited as ATCC Designation No. PTA-123324, or progeny, derivatives or descendants from the cells, including from culturing PTA-123324 cells to obtain progeny, derivative or descendant cells.

Provided herein are methods of preparing cell lines, wherein the cell lines comprise recombinant cardiomyocytes expressing hERG and stable cell lines comprising such cardiomyocytes. In some embodiments, methods as provided herein comprise transfecting or transducing immortalized cardiomyocytes, including for example, immortalized adult human ventricular cardiomyocytes, with a nucleic acid sequence encoding hERG. In some embodiments, the nucleic acid sequence is transferred on a vector by transfecting or transducing the vector. In some embodiments, the vector is a retroviral vector, such as a lentiviral vector. In some embodiments, when the vector is a lentiviral vector, the method further comprises the step of generating pseudo-lentiviral particles.

Provided herein are methods for determining cardiotoxicity (e.g., hERG-related or non-hERG-related) of compounds using recombinant cardiomyocytes or cardiomyocyte cell lines as provided herein.

Provided herein are methods of screening compounds for cardiotoxicity, the methods comprising using recombinant cardiomyocytes or cardiomyocyte cell lines as provided herein, including in methods for determining the activity of compounds to inhibit hERG.

In some embodiments, provided herein are methods for determining the activity of a compound to inhibit hERG (e.g., by blocking or obstructing a hERG channel), wherein the methods comprise using recombinant cardiomyocytes or cardiomyocyte cell lines as provided herein.

In some embodiments, the methods for determining the activity of a compound to inhibit hERG comprise: a) providing recombinant cardiomyocytes overexpressing hERG; b) contacting the cardiomyocytes with a compound; c) measuring a test current (e.g., in a patch clamp apparatus); and d) determining if the test current is reduced in the presence of the compound, wherein a reduced test current is indicative of hERG inhibitory activity. In some embodiments, the test current is compared before and after contacting the recombinant cardiomyocytes with the compound.

Provided herein are methods of screening compounds for cardiotoxicity comprising using recombinant cardiomyocytes or cardiomyocyte cell lines as provided herein, including in methods for determining the activity of compounds to reduce cell viability.

In some embodiments, the methods for determining the activity of compounds to reduce cell viability comprise: a) providing recombinant cardiomyocytes overexpressing hERG; b) contacting the cardiomyocytes with a compound in the presence of a viability indicator compound; c) measuring a signal of the indicator compound; and d) determining if the signal is reduced or increased in the presence of the compound, wherein a reduced or increased signal is indicative of reduced cell viability. In some embodiments, the signal is an absorbance, luminescence or fluorescence signal. In some embodiments, the signal is a fluorescence signal. In some embodiments, the cell viability is compared before and after contacting the recombinant cardiomyocytes with the compound.

In some embodiments, the recombinant cardiomyocytes or cardiomyocyte cell lines used in the various methods as provided herein are designated hMYO-hERG. Exemplary cells include those deposited as ATCC Designation No. PTA-123324, or progeny, derivatives, or descendants from the cells, including from culturing PTA-123324 cells to obtain progeny, derivative, or descendant cells.

Provided herein are methods of using the recombinant cardiomyocytes or cardiomyocyte cell lines as disclosed herein, or progeny, derivatives or descendants from the recombinant cardiomyocytes or cardiomyocyte cell lines, including from cells deposited as ATCC Designation No. PTA-123324, as disclosed herein. Such uses include drug screening for cardiotoxicity (e.g., hERG-related or non-hERG-related).

Provided herein are kits comprising the recombinant cells or cell lines as provided herein, including, for example, those designated as hMYO-hERG. In some embodiments, the kits comprise cells from the cells deposited as ATCC Designation No. PTA-123324, or progeny, derivatives or descendants from the cells, including from culturing PTA-123324 cells to obtain progeny, derivative, or descendant cells.

4. BRIEF DESCRIPTION OF THE FIGURES

FIG. 1 shows a schematic representation depicting S1-S6 helices of hERG.

FIG. 2 shows the amino acid sequence of SEQ ID NO: 1 comprising an exemplary hERG amino acid sequence (see, e.g., amino acids 1-1159, as set forth in SEQ ID NO: 1). SEQ ID NO: 1 additionally comprises an exemplary linker amino acid sequence (see, e.g., amino acids 1160-1177 as set forth in SEQ ID NO: 1) and an exemplary FLAG tag amino acid sequence (see, e.g., amino acids 1178-1185 as set forth in SEQ ID NO: 1).

FIG. 3 shows SEQ ID NO: 2, nucleic acid sequence encoding amino acid sequence as set forth in SEQ ID NO: 1.

FIG. 4A shows an HIV based lentiviral vector carrying an exemplary nucleic acid sequence encoding hERG. FIGS. 4B-4C shows the expression of hERG in the generated hMYO-hERG cells, HEK-hERG cells, and HeLa-hERG cells compared with control and other cell lines. In FIGS. 4B-4C, HEK, hMYO and HeLa are control cells. HEK-hERG, hMYO-hERG, HeLa-hERG are recombinant cell lines that have been transduced with nucleic acid sequences encoding hERG. hMYO-Nav1.5-2 is a cell line expressing control plasmids encoding a subunit of Nav1.5 ion channel (negative control for hERG ion channel). hMYO-Nav1.5-6 is a cell line expressing a subunit of Nav1.5 ion channel (negative control for hERG ion channel).

Figure 7A:
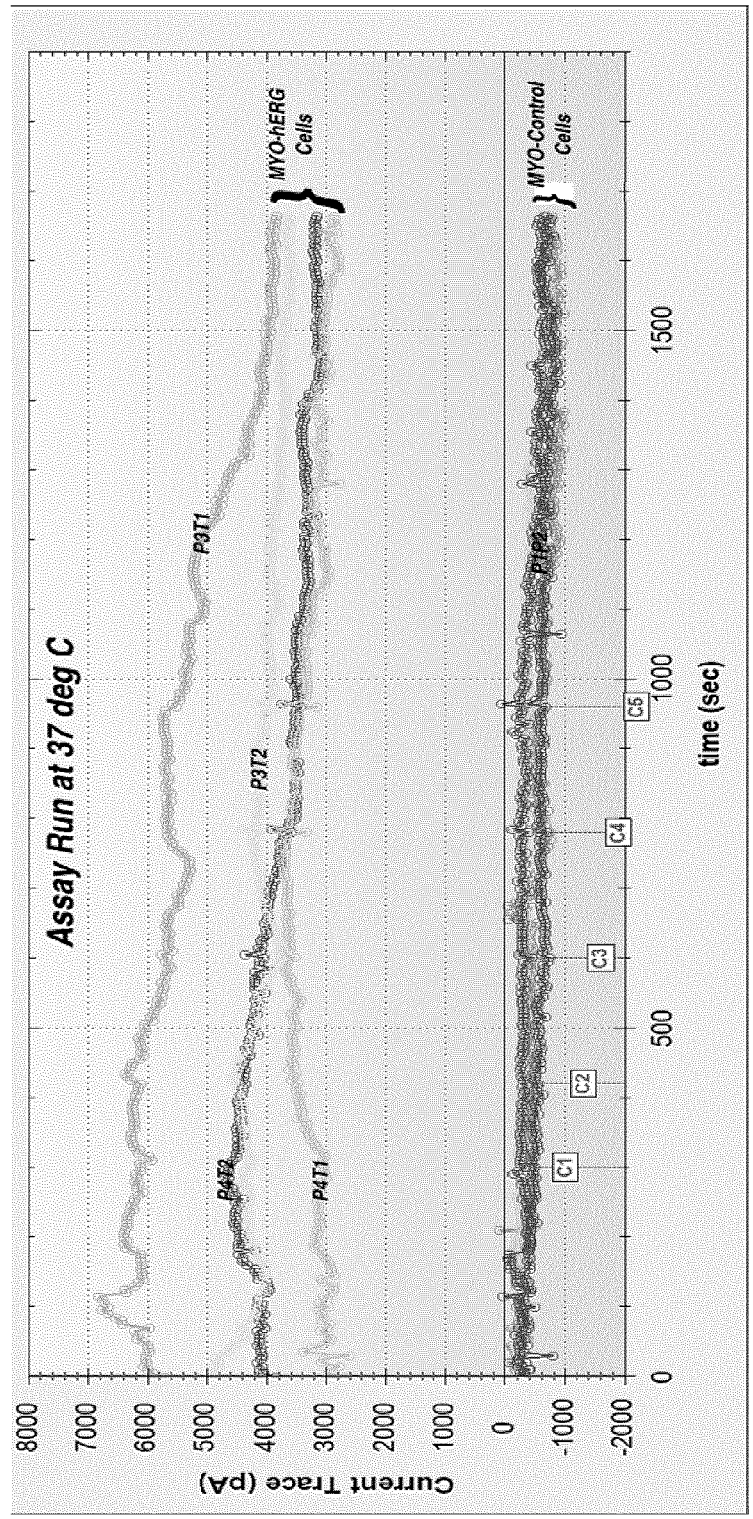
Figure 7B:
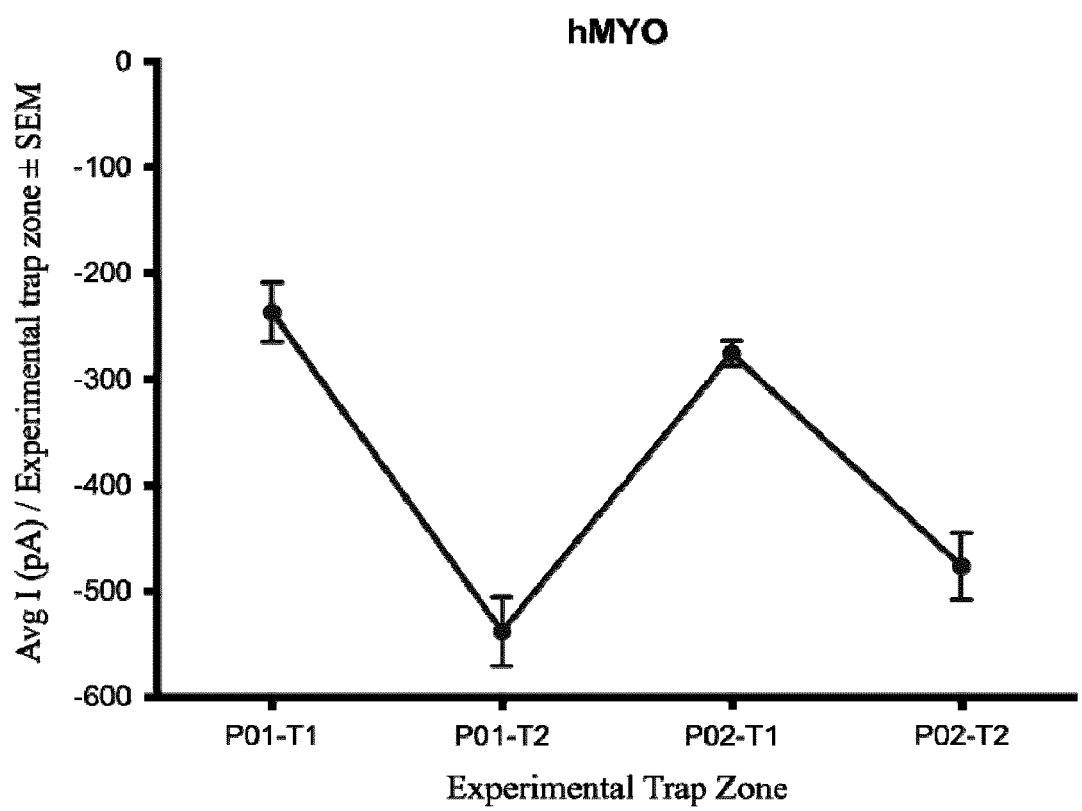
Figure 7C:
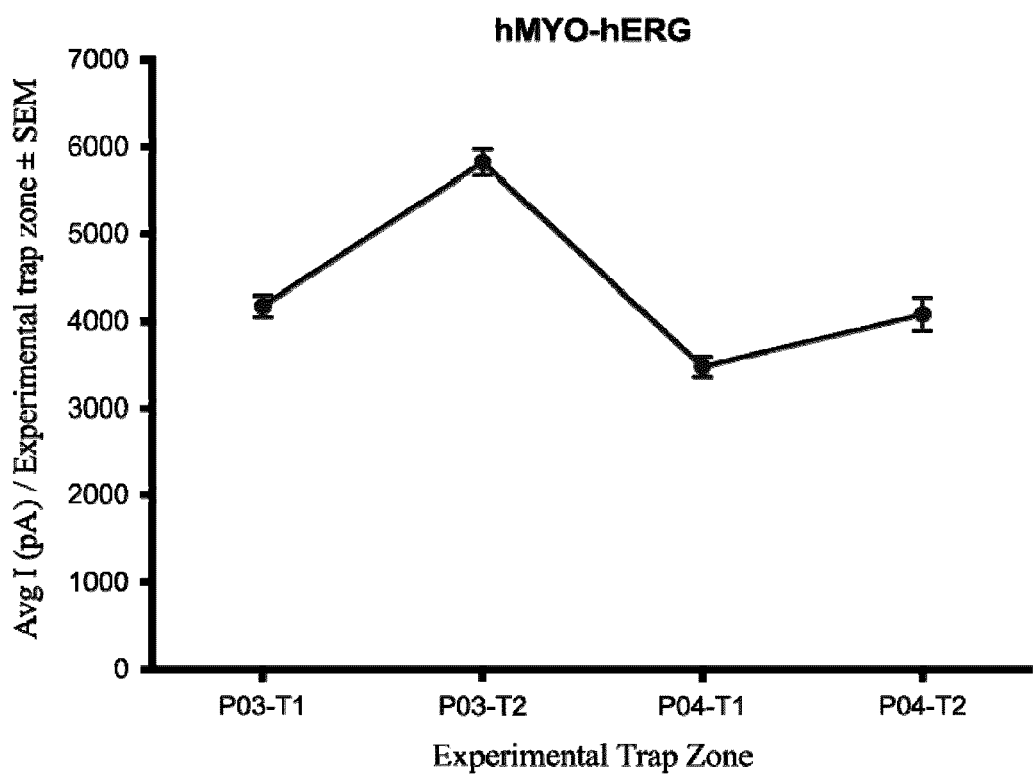

FIG. 7A shows currents of hMYO-hERG cells of passage No. 14 and the currents of hMYO cells (control without transfected or transduced hERG) at 37° C. FIG. 7B shows currents exhibited in the hMYO cells that did not express hERG. FIG. 7C shows currents exhibited in the hMYO-hERG cells expressing hERG.

Figure 8:
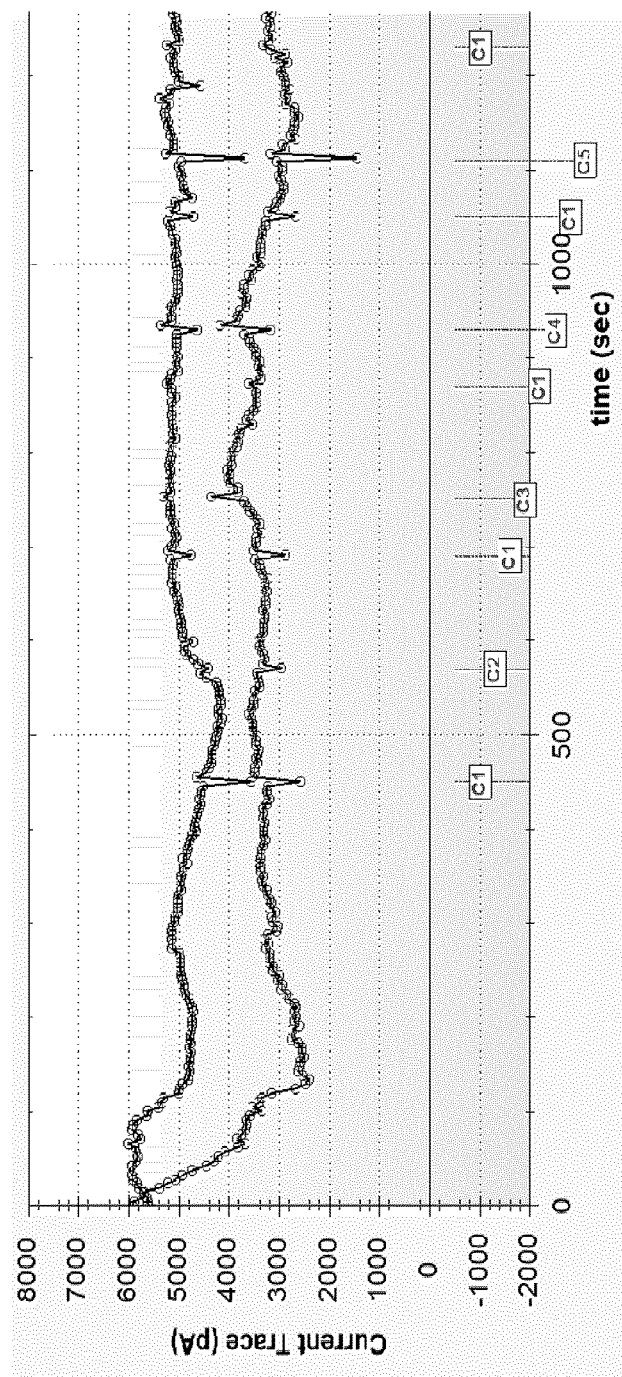

FIG. 8 shows currents of the hMYO-hERG cells of passage No. 17 at 37° C.

Figure 9:
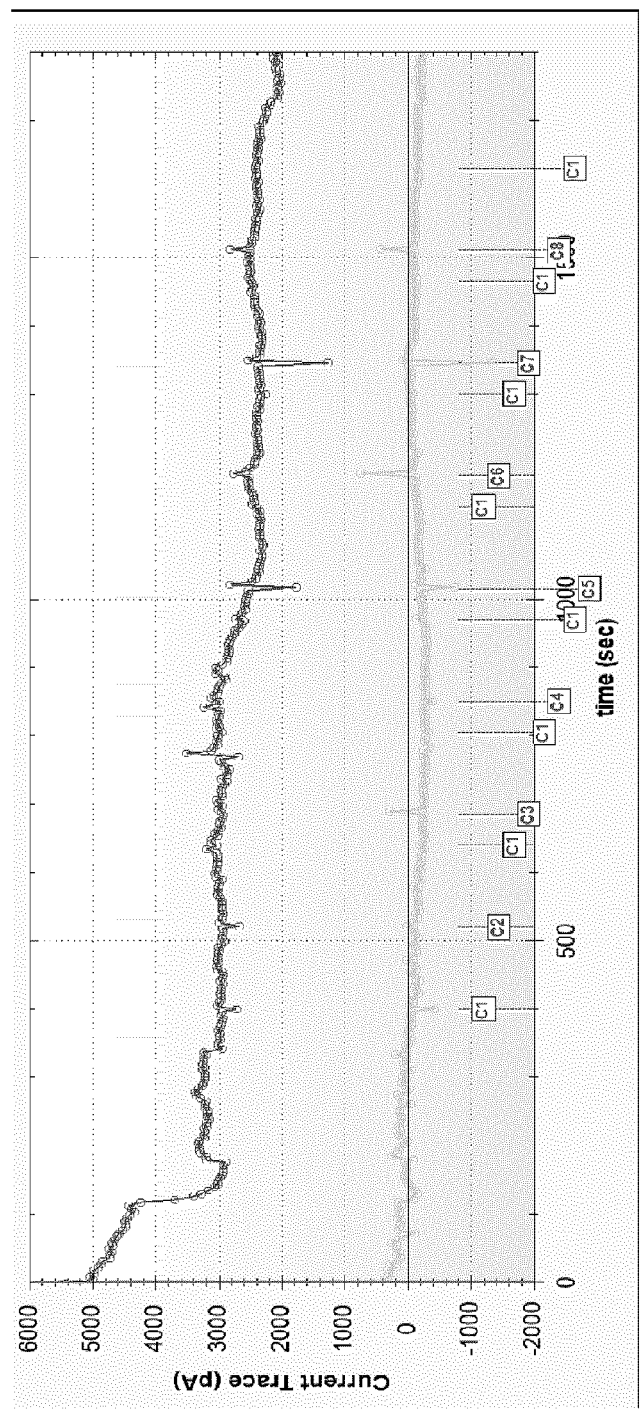

FIG. 9 shows currents of the hMYO-hERG cells of passage No. 25 at 37° C.

Figure 10:
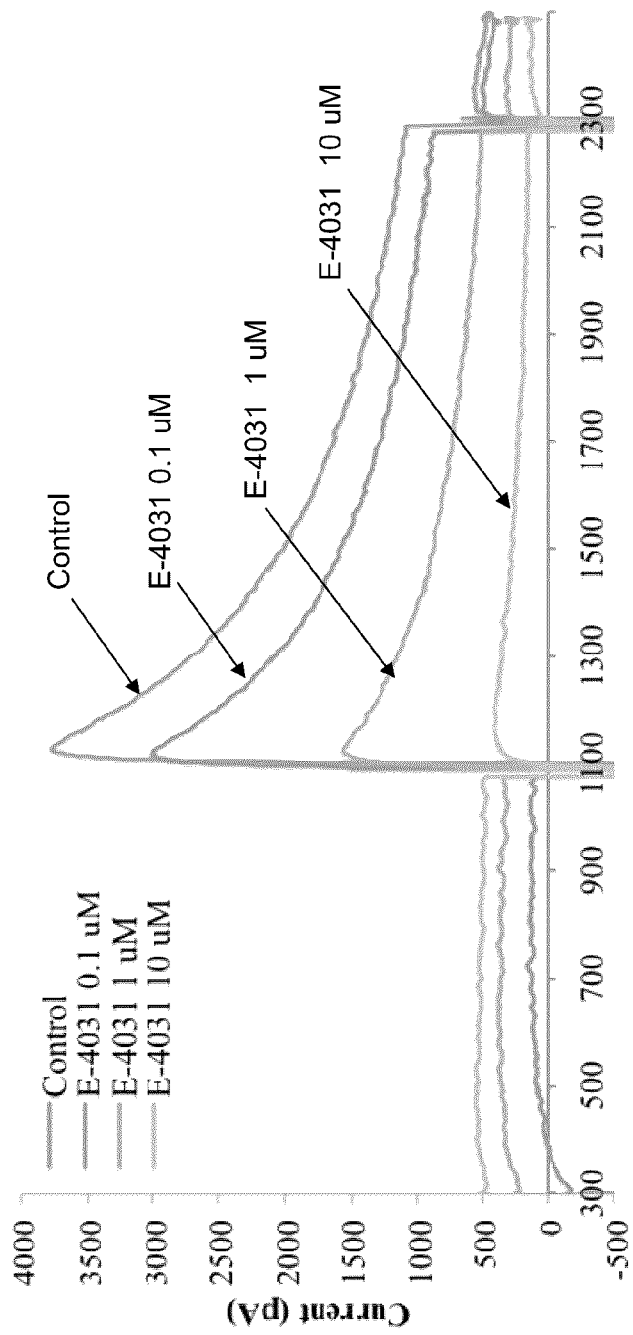

FIG. 10 shows block of hERG tail current by E-4031 in hMYO-hERG cells.

Figure 11:
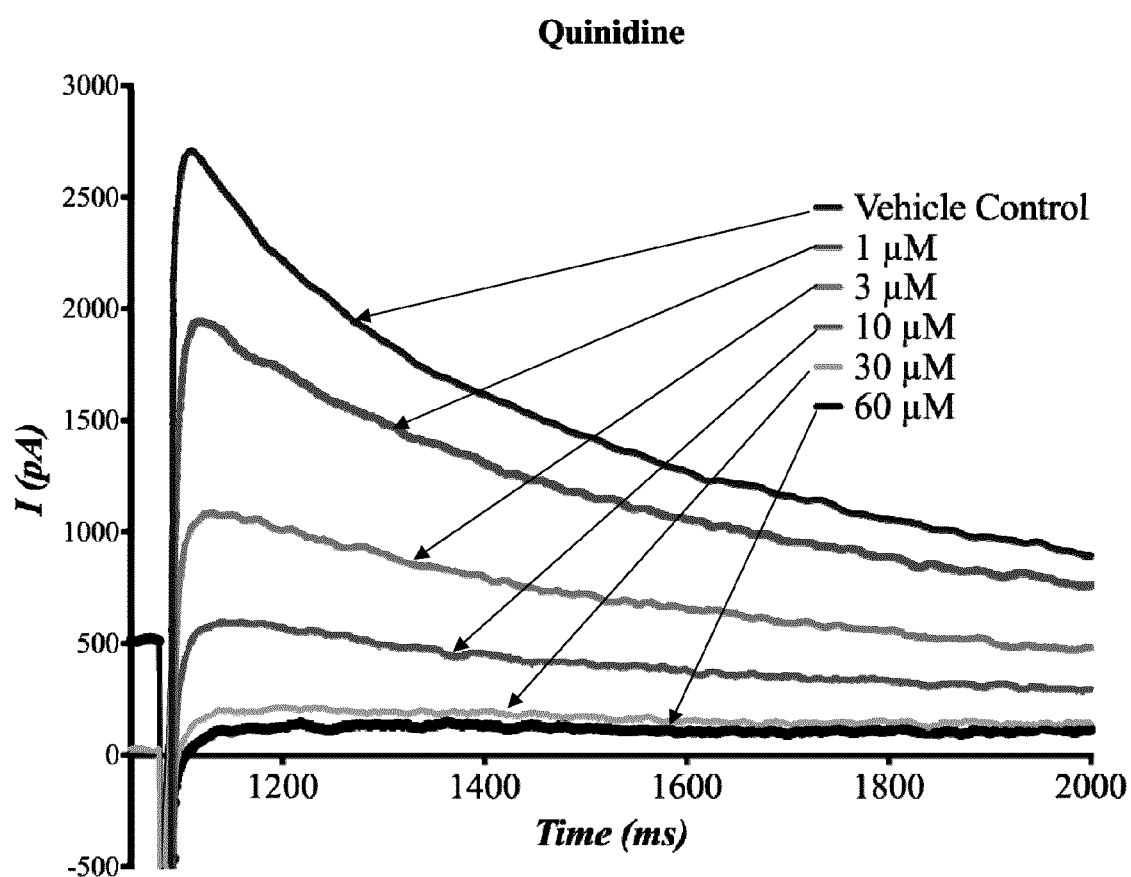

FIG. 11 shows block of hERG tail current by quinidine in hMYO-hERG cells.

Figure 12A:
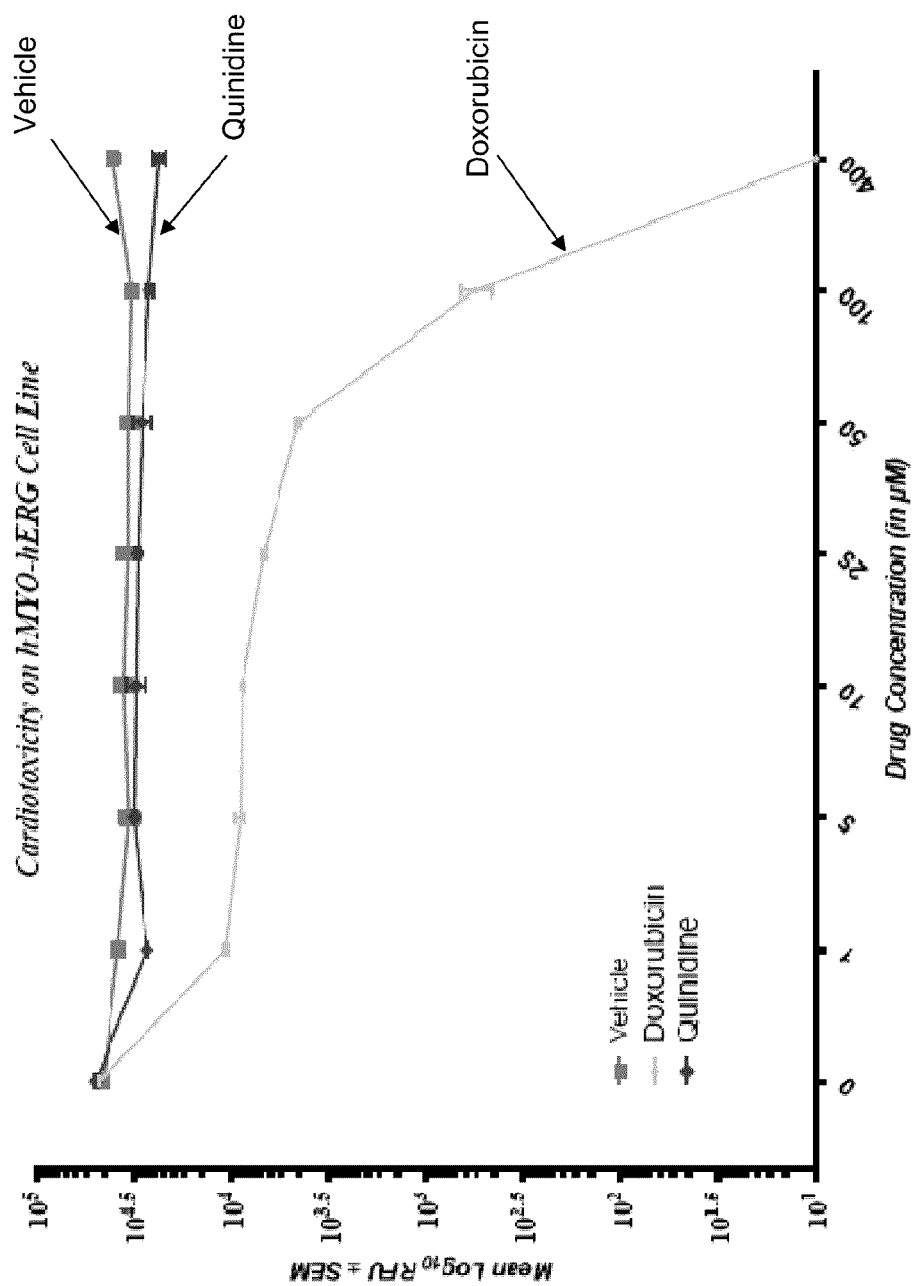
Figure 12B:
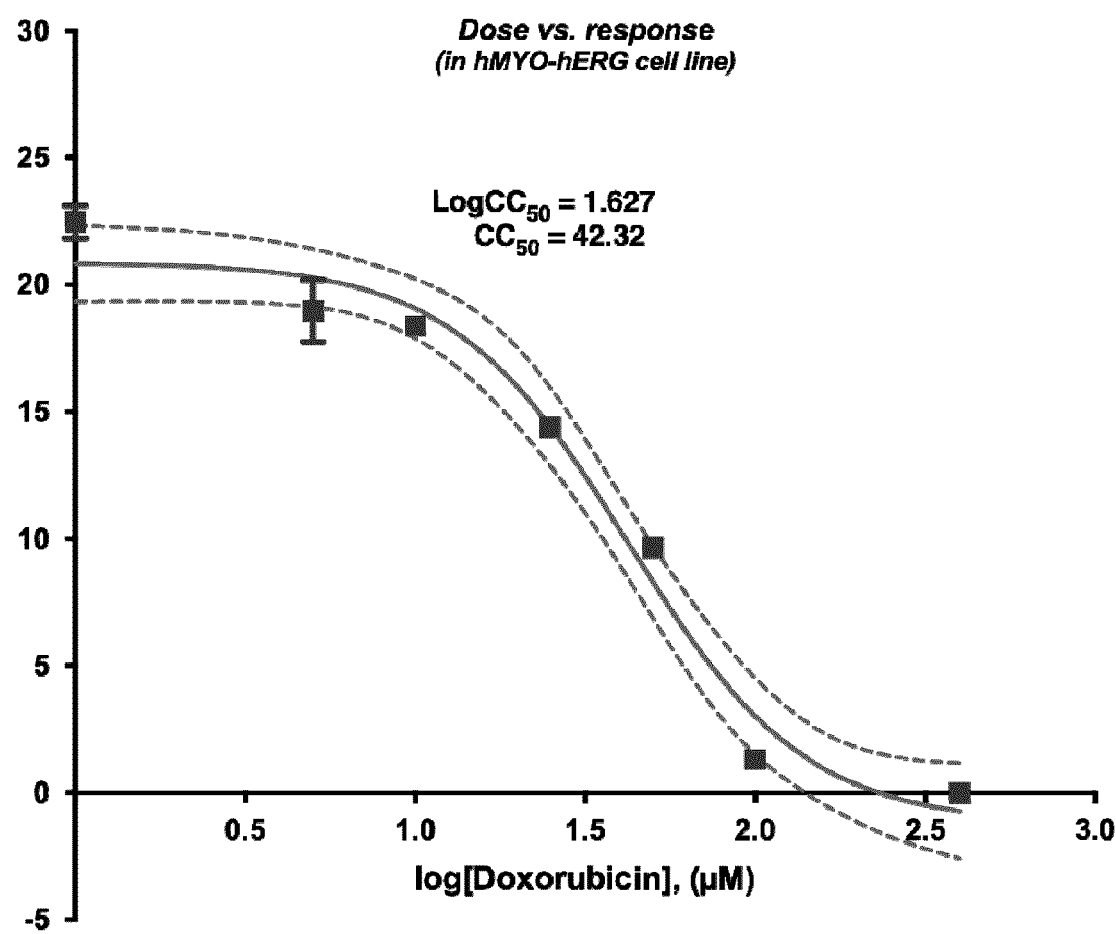

FIG. 12A shows an exemplary determination of cell viability using SetuBlue cell viability reagent: hMYO-hERG cells were plated in 96 well plate and exposed to various concentration of control and test compounds. Cells were assayed with Setublue reagent, incubated at 37° C. at standard culture conditions, and fluorescence was measured at 530/590 using PerkinElmer EnSpire® multimode plate reader. FIG. 12B shows an exemplary $CC_{50}$ value as determined by locating the X-axis value corresponding to one-half the maximum (plateau) relative fluorescence unit (RFU) value using GraphPad Prism software.

5. DETAILED DESCRIPTION

5.1 Definitions

As used herein, the term "human ERG," "human ERG1," "hERG" or "hERG1" refers to a human Ether-à-go-go-Related Gene of chromosome 7q36.1 that codes for a protein known as Kv11.1, the alpha (a) subunit of potassium voltage-gated channel, subfamily H (eag-related), member 2. It will be known to those of ordinary skill in the art that hERG or hERG1 can be also called different names, such as erg1, ERG1, KCNH2, Kv11.1, LQT2, and SQT1. See, e.g., "KCNH2 potassium voltage-gated channel, subfamily H (eag-related), member 2 [Homo sapiens (human)]," Gene ID: 3757, updated 3-Nov.-2013, http://www.ncbi.nlm.nih.gov/gene/3757. As used herein, the term "hERG" or "hERG1" refers interchangeably to the gene and the protein known as Kv11.1 encoded by the gene. See also, e.g., "Potassium voltage-gated channel subfamily H member 2, Gene KCNH2, UniProt Kb-Q12809 (KCNH2_human)," (http://www.uniprot.org/uniprot/Q12809). An exemplary hERG polypeptide sequence is set forth in GenBank Accession Number BAA37096, and an exemplary hERG nucleic acid sequence is set forth in GenBank Accession Number SEG_AB00905S. In some embodiments, the amino acid sequence set forth in SEQ ID NO: 1 comprises a hERG amino acid sequence (see, e.g., amino acids 1-1159 as set forth in SEQ ID NO: 1).

As used herein, the term "hERG channel" refers to a potassium voltage-gated channel comprising Kv11.1, which is the alpha (α) subunit of the channel which forms a pore through a plasma membrane for passage of potassium ions across a plasma membrane.

As used herein, the term "protein" or "polypeptide" refers to any polymer comprising amino acids, including any of the 20 naturally occurring amino acids, regardless of its size. The 20 naturally occurring amino acids may be classified into non-polar amino acids (Ala, Ile, Leu, Met, Phe, Pro, Trp, Val), uncharged amino acids (Asn, Cys, Gln, Gly, Ser, Thr, Tyr), acidic amino acids (Asp, Glu), and basic amino acids (Arg, His, Lys). Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein", "polypeptide" and "peptide" are used interchangeably herein, for example, when referring to a gene product.

As used herein, the term "polynucleotide" refers to a polymer comprising a plurality of bases, such as deoxyribonucleic acid (DNA) or ribonucleic acid (RNA), or base pairs, and includes DNA, cDNA, genomic DNA, and chemically synthesized DNA and RNA. Polynucleotides optionally containing non-natural bases are also included in the term "polynucleotide." Specific examples of non-natural bases include 4-acetylcytidine, 5-(carboxyhydroxylmethyl) uridine, 2'-O-methylcytidine, 5-carboxymethylaminomethyl-2-thiouridine, 5-carboxymethylaminomethyluridine, dihydrouridine, 2'-O-methylpseudouridine, β-D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, β-D-mannosylqueosine, 5-methoxycarbonylmethyl-2-thiouridine, 5-methoxycarbonylmethyluridine, 5-methoxyuridine, 2-methylthio-N-6-isopentenyladenosine, N-((9-β-D-ribofuranosyl-2-methyltiopurine-6-yl)carbamoyl)threonine, N-((9-β-D-ribofuranosylpurine-6-yl)N-methyl-carbamoyl)threonine, uridine-5-oxyacetic acid-methyl ester, uridine-5-oxyacetic acid, wybutoxosine, pseudouridine, queosine, 2-thiocytidine, 5-methyl-2-thiouridine, 2-thiouridine, 4-thiouridine, 5-methyluridine, N-((9-β-D-ribofuranosylpurine-6-yl)carbamoyl)threonime, 2'-O-methyl-5-methyluridine, 2'-O-methyluridine, wybutosine and 3-(3-amino-3-carboxypropyl)uridine.

As used herein, the term "exogenous nucleic acid sequence" refers to a sequence originating from outside of a given cell. Such a sequence can be introduced or transferred by genetic engineering into a cell or cell line, including by transformation, transfection, or transduction to generate a recombinant cell or cell line. For example, as disclosed herein, an exogenous nucleic acid sequence encoding hERG is introduced or transferred by genetic engineering into a cardiomyocyte or cardiomyocyte cell line, including an immortalized cardiomyocyte or immortalized cardiomyocyte cell line, to generate a recombinant cardiomyocyte or cardiomyocyte cell line. Such a recombinant cardiomyocyte or cardiomyocyte cell line, is designated herein as a "hERG-overexpressing cardiomyocyte" or a "hERG-overexpressing cardiomyocyte cell line". As also disclosed herein, an exogenous nucleic acid sequence encoding hERG, useful for introduction or transfer by genetic engineering into a cell or cell line, optionally comprises additional sequences including, for example, regulatory sequences, selectable marker sequences, and/or tag sequences. An exemplary hERG-encoding nucleic acid sequence is set forth in FIG. 3, and includes a tag sequence (e.g., FLAG tag).

As used herein, the term "transformation" refers to a method by which an exogenous nucleic acid sequence is introduced or transferred into a cell. In some embodiments, a cardiomyocyte is transformed with an exogenous nucleic acid sequence encoding hERG. The exogenous nucleic acid sequence encoding hERG optionally comprises additional sequences including, for example, regulatory sequences, selectable marker sequences, and/or tag sequences. Such a transformed cardiomyocyte is designated herein as a "hERG-overexpressing cardiomyocyte".

As used herein, the term "transfection" refers to a method by which an exogenous nucleic acid sequence is introduced or transferred into a cell by non-viral means, such as, for example, through use of a non-viral vector. In some embodiments, a cardiomyocyte is transfected with an exogenous nucleic acid sequence encoding hERG through use of a non-viral vector. The exogenous nucleic acid sequence encoding hERG optionally comprises additional sequences including, for example, regulatory sequences, selectable marker sequences, and/or tag sequences. Such a transfected cardiomyocyte is designated herein as a "hERG-overexpressing cardiomyocyte".

As used herein, the term "transduction" refers to a method by which an exogenous nucleic acid sequence is introduced or transferred into a cell by viral means, such as, for example, through use of a viral vector. In some embodiments, a cardiomyocyte is transfected with an exogenous nucleic acid sequence encoding hERG through use of a viral vector. The exogenous nucleic acid sequence encoding hERG optionally comprises additional sequences including, for example, regulatory sequences, selectable marker sequences, and/or tag sequences. Such a transduced cardiomyocyte is designated herein as a "hERG-overexpressing cardiomyocyte".

As used herein, the term "cell" refers not only to a given cell, but also to progeny or potential progeny of such a cell, including an immortalized cell, for example, progeny, derivative, or descendent cells of an immortalized cell. Exemplary cells include those deposited as ATCC Designation No. PTA-123324, or progeny, derivatives, or descendants from the cells, including from culturing PTA-123324 cells to obtain progeny, derivative, or descendant cells. Because certain modifications can occur in succeeding generations due to either mutation or environmental influences, such progeny might not, in fact, be identical to the parent cell, but are still included within the scope of the term as used herein.

The term "cell line" refers to immortalized cells (e.g., a cell population) that proliferate indefinitely. A cell line may be derived from primary cells (e.g., a primary cell culture) by immortalizing the cells, for example, with SV40, hTERT, HPV E6/E7, EBV, MycT58A, RasV12, and p53. An exogenous nucleic acid sequence, including, for example, an exogenous nucleic acid sequence encoding hERG, can be introduced or transferred by genetic engineering into a cell line, including by transformation, transfection, or transduction. The exogenous nucleic acid sequence encoding hERG optionally comprises additional sequences including, for example, regulatory sequences, selectable marker sequences, and/or tag sequences. A "stable" cell line is a cell line that exhibits substantially consistent characteristics over time (e.g., as the cells proliferate in culture, for example, with each doubling, or as they are passaged). A stable cell line may be derived from a cell line that has been transformed, transfected, or transduced with an exogenous nucleic acid sequence, including, for example, an exogenous nucleic acid sequence encoding hERG. The exogenous nucleic acid sequence encoding hERG optionally comprises additional sequences including, for example, regulatory sequences, selectable marker sequences, and/or tag sequences.

The terms "progeny" and "descendants" as used herein refer to cells obtained by culturing or otherwise growing a cell as described herein. Exemplary progeny or descendants are cells obtained by culturing cells from those deposited as ATCC Designation No. PTA-123324.

The term "derivative" as used herein refers to a cell that is obtained by modifying, for example, by fusing, transforming, transfecting, transducing, or otherwise changing a cell, including progeny or descendants of the modified cell. Exemplary derivative cells are cells obtained by culturing cells from those deposited as ATCC Designation No. PTA-123324, and modified, including by fusing, transforming, transfecting, transducing, or otherwise changing a cell.

As used herein, the term "host cell" refers to a cell into which an exogenous nucleic acid sequence has been introduced or transferred. In some embodiments, host cells include, but are not limited to, mammalian cells (e.g., human cells such as cardiomyocytes).

As used herein, the term "expression," and grammatical derivatives thereof, generally refers to the cellular processes by which a polypeptide is produced from RNA. For example, a hERG expressing cell produces a hERG protein a hERG encoding nucleic acid sequence such as a hERG encoding RNA.

Figure 4A:
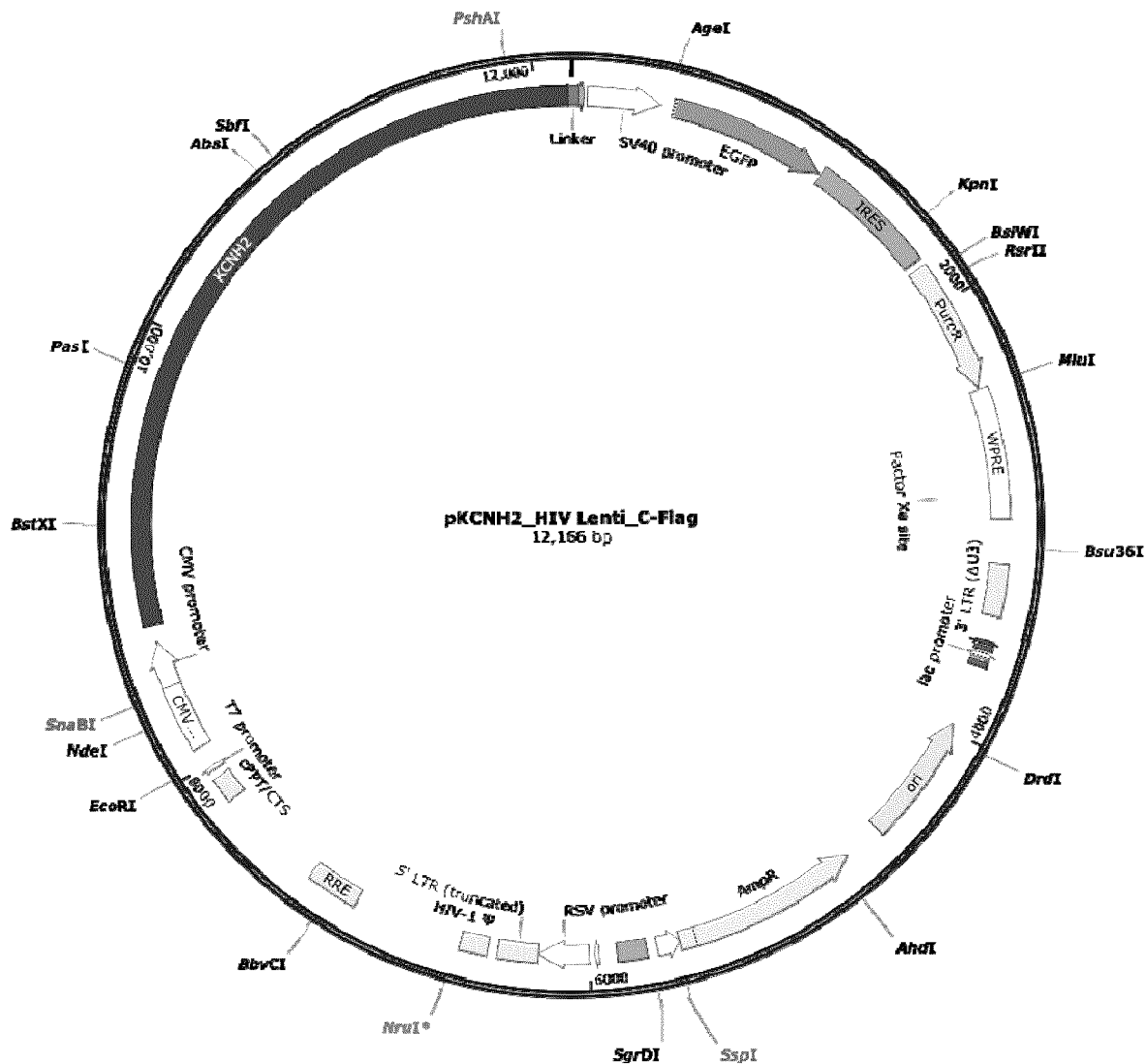
Figure 4B:
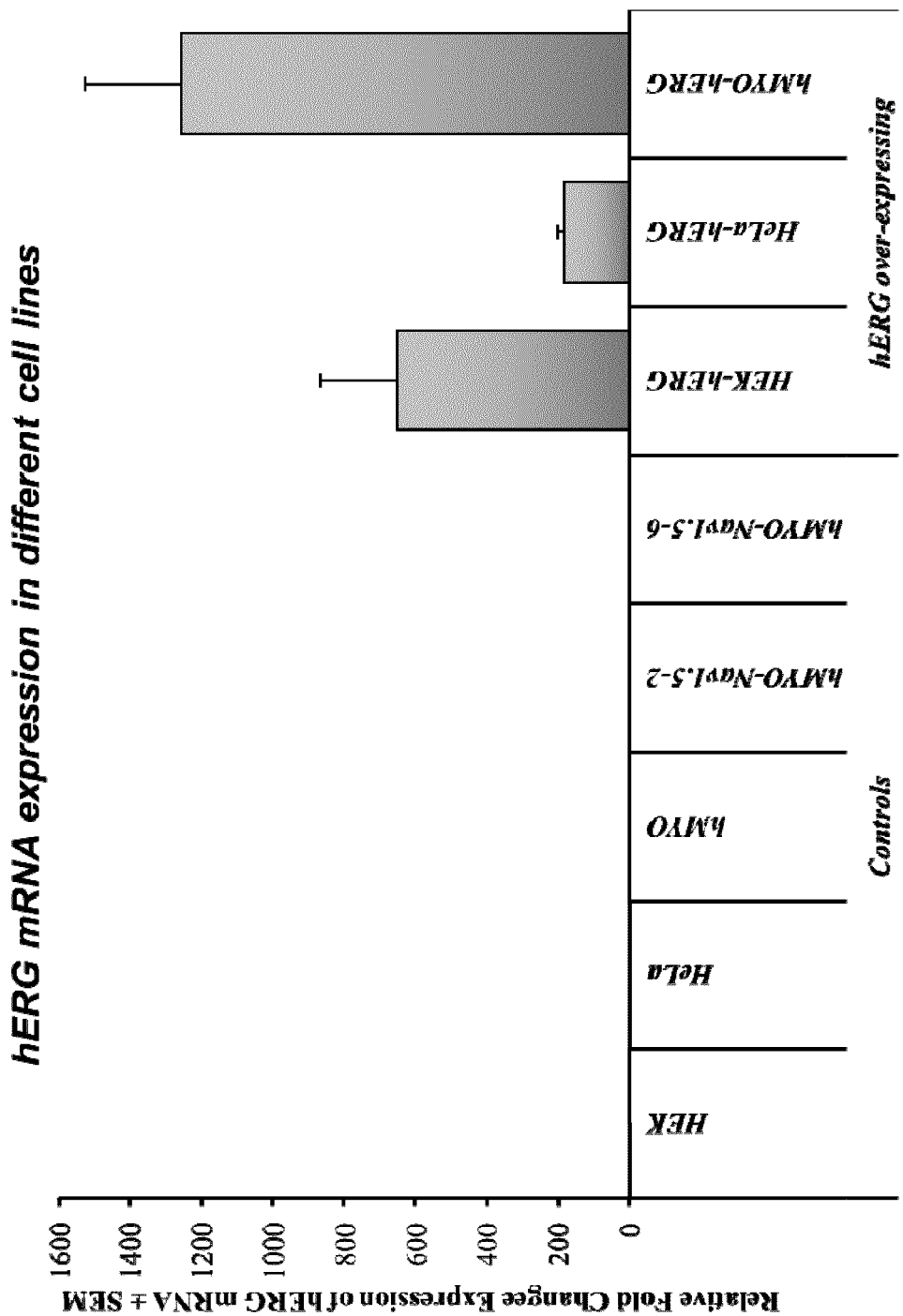
Figure 4C:
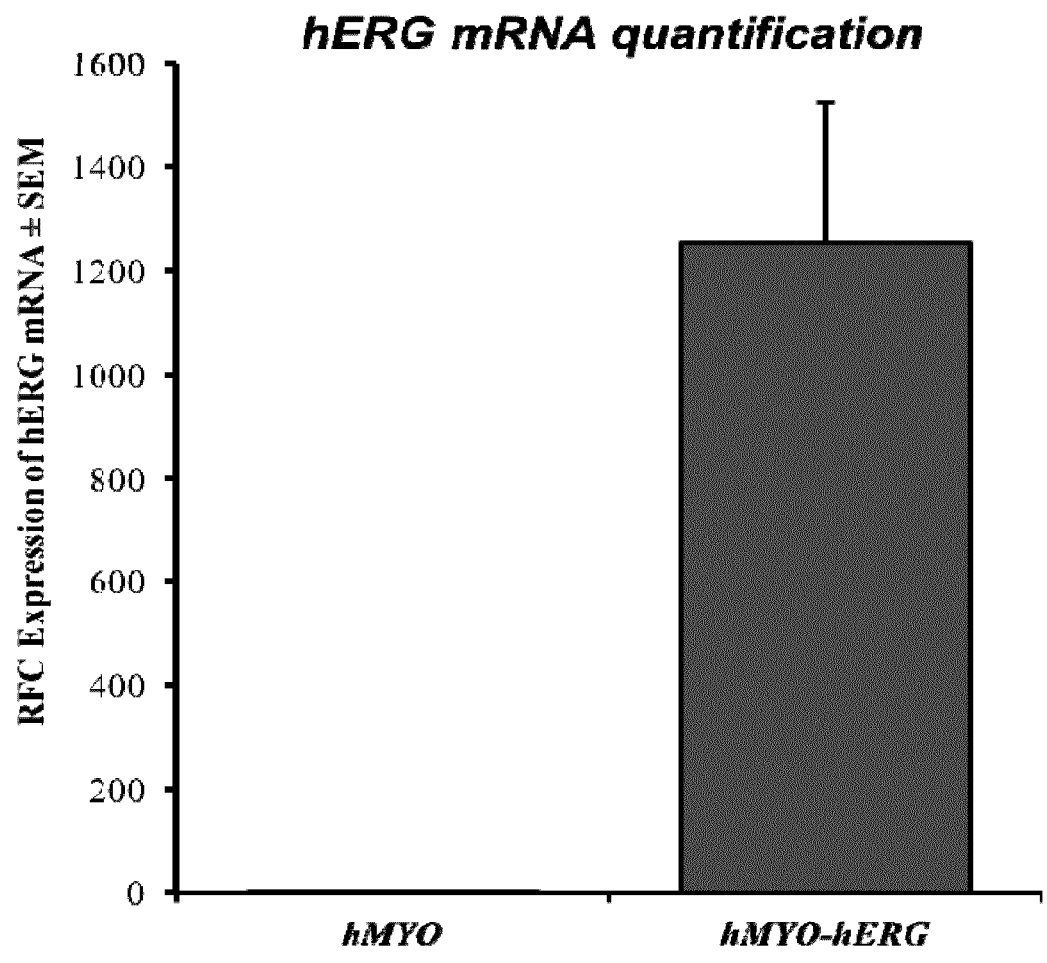

As used herein, "overexpression," and grammatical derivatives thereof, refers to expression of a protein in a genetically engineered cardiomyocyte (e.g., a recombinant cell) at levels above those normally found in the unengineered (e.g., parental) cardiomyocyte under the same culture conditions (see, e.g., Example 2 and FIGS. 4B and 4C).

As used herein, the terms "hERG-overexpressing cells," "hERG-overexpressing cell line," "cardiomyocytes overexpressing hERG," "cardiomyocyte cell line overexpressing hERG," and the like, refers to cells or a cell line in which an exogenous nucleic acid sequence encoding hERG is introduced or transferred by genetic engineering into the cells or cell line, for example, cardiomyocytes or cardiomyocyte cell line. Exemplary hERG-overexpressing cells are those designated hMYO-hERG as disclosed herein (see, e.g., Example 2 and FIGS. 4B and 4C). Additional exemplary hERG-overexpressing cells are cells obtained from those deposited as ATCC Designation No. PTA-123324, including their progeny, descendants, or derivatives thereof.

As used herein, the term "cardiotoxic" or "cardiotoxicity" of a compound refers to cardiotoxicity of the compound in vitro, as measured by in vitro activities of the compound, including hERG inhibitory activity and/or cell viability reduction activity. For example, as disclosed herein, methods for screening compounds for cardiotoxicity and/or methods for determining cardiotoxicity of compounds determine the cardiotoxicity of the compounds by measuring the activity of the compounds to inhibit hERG and/or by measuring the activity of the compounds to reduce cell viability. Such in vitro methods of determining cardiotoxicity are useful for predicting the risk of cardiotoxicity in vivo. Cardiotoxicity of a compound in vivo refers to having a toxic effect on the heart, for example, by a compound having a deleterious effect on the action of the heart, due to poisoning of the cardiac muscle or of its conducting system. Cardiotoxicity can include functional cardiotoxicity (e.g., acute alteration of the mechanical function of the myocardium) or structural cardiotoxicity (e.g., morphological damage to cardiomyocytes or loss of cardiomyocyte viability). In some embodiments, long Q-T syndrome or "LQTS" is an aspect of cardiotoxicity (e.g., an aspect of functional cardiotoxicity). In some embodiments, loss of cell viability is an aspect of cardiotoxicity (e.g., an aspect of structural cardiotoxicity). In some embodiments, a variety of cellular changes, for example, cytoskeletal, nuclear, mitochondrial, golgi and/or other subcellular compartment changes are aspects of morphological damage to cardiomyocytes (e.g., aspects of structural cardiotoxicity).

As used herein, the term "reduced cardiotoxicity" of a compound refers to reduced cardiotoxicity of the compound in vitro. In some embodiments, a compound has reduced cardiotoxicity if it does not inhibit (e.g., by blocking or obstructing, either fully or partially) hERG. In some embodiments, a compound has reduced cardiotoxicity if it does not reduce cardiomyocyte viability.

As used herein, the term "cell viability," for example, as measured by cell death, lack of cell division, or cell dysfunction, refers to the ability of the cell to maintain metabolic capacity, proliferate, and/or maintain integrity of cell membranes, as measured, for example, by a viability assay. Exemplary viability assays include an ATP/ADP assay; a Calcein AM assay; a clonogenic assay; an ethidium homodimer assay; a cytochrome oxidase activity assay; an adenylate kinase (AK) assay; an Alamar Dye/Setublue assay; a lactate dehydrogenase (LDH) assay; formazan-based assays (MTT/XTT); reduction of MTS tetrazolium; dyes such as, e.g., Evans blue, neutral red, methyl violet, propidium iodide, sulforhodamine B, fluorescein diacetate hydrolysis/Propidium iodide staining (FDA/PI staining), carboxyfluorosuccinimide ester (CFSE) dye, Resazurin, Trypan Blue, and a living-cell exclusion dye (dye only crosses cell membranes of dead cells)); detection of mutations in mtDNA; release of components across the mitochondrial permeability transition pore; changes in mitochondrial membrane potential; flow cytometry; green fluorescent protein; a DNA stain that can differentiate necrotic, apoptotic and normal cells; measurement of cytochrome c release; caspase proteolytic cleavage of poly(ADP-ribose) polymerase (PARP); detection of Annexin V; senescence-associated expression of β-galactosidase (SA-β-Gal) activity; a TUNEL assay; and the like One of ordinary skill in the art will understand that the parameters that define cell viability in a particular assay can be diverse, for example, as the redox potential of the cell population, the integrity of cell membranes, or the activity of certain cellular enzymes. Each assay provides a different snapshot of cell health, and can individually or together form the basis of an assay for cell viability. For example, cardiotoxicity of a test compound can be measured in methods using recombinant cardiomyocytes or cardiomyocyte cell lines as provided herein, by measuring cell viability in the presence of the test compound and a viability indicator compound, wherein a reduction in cell viability in the presence of the test compound is detected by measuring a signal from the indicator compound, wherein the signal of the indicator compound is increased or decreased in the presence of the test compound, wherein a reduction or increase in the signal is indicative of reduced cell viability. Reduction in cell viability may be measured when a compound is cytotoxic or cytostatic.

As used herein, the term "reduced cell viability" with reference to cells, including cardiomyocytes, refers to a change in the value of a measured parameter, for example, that indicates cell death, lack of cell division, mitochondrial disruption, calcium dyshomeostasis, and/or decrease in cellular ATP content in the cells, including cardiomycytes, for example, when the cardiomyocytes are contacted with a compound. One of ordinary skill in the art will understand that such changes can be accompanied by mitochondrial membrane potential, loss of endoplasmic reticulum integrity, increased $Ca^{2+}$ mobilization, and ATP depletion in the cells, including cardiomyocytes (see, e.g., Pointon et al. (2013) *Toxicol Sci.* 132(2): 317-26).

As used herein, the term "ion channel" or "ion channel protein," refers to a membrane bound protein that acts as a pore in a cell membrane and permits the selective passage of ions (such as potassium ions), by means of which electrical current passes in and out of the cell, such as a hERG channel.

As used herein, the term "potassium ion channel" or "potassium ion channel protein," refers to an ion channel that permits the selective passage of potassium ions ($K^+$), such as a hERG channel.

As used herein, the term "hERG activity" refers to any observable effect flowing from hERG channel operation (e.g., passage and/or movement and/or flux of potassium ($K^+$) ions across a plasma membrane). A representative, but non-limiting, example of hERG activity in the context of the present disclosure includes conducting electrical current, by passage and/or movement and/or flux of potassium ($K^+$) ions out of the cell across the plasma membrane.

As used herein, the terms "hERG inhibitory activity" or "hERG current inhibitory activity" are used interchangeably, and refer to the activity of a compound to inhibit (e.g., by blocking or obstructing, either fully or partially) a hERG channel, for example, by inhibiting passage and/or movement and/or flux of potassium ($K^+$) ions across a plasma membrane. As described herein, ion passage and/or movement and/or flux through a hERG channel are detected as currents, for example, as detected by a patch clamp technique, as disclosed herein. For example, hERG inhibitory activity of a compound, that is, the activity of a compound to inhibit hERG, can be measured in methods using recombinant cardiomyocytes or cardiomyocyte cell lines as provided herein by measuring current in the presence of the compound, wherein a reduction in current in the presence of the compound indicates hERG inhibitory activity.

As used herein, the term "compound" and "drug" are used interchangeably, and refer to any small molecule which is capable of binding to a target receptor, for example, hERG1. In some embodiments, the compound inhibits hERG activity. In some embodiments, if a compound or drug inhibits hERG activity, the compound or drug may be referred to as a blocker.

As used herein, "high throughput screening" refers to a method that allows a researcher to quickly conduct chemical, genetic or pharmacological tests, the results of which provide starting points for drug design and for understanding the interaction or role of a particular biochemical process in biology. For example, as disclosed herein, methods for screening compounds for cardiotoxicity, and/or methods for determining cardiotoxicity of compounds, for example, measure the activity of the compounds to inhibit hERG and/or the activity of the compounds to reduce cell viability, and are useful as high throughput screening methods.

As used herein, "electrophysiology techniques" refers to the use of electrophysiology measurements to measure voltage change or electric current on a wide variety of scales, including single ion channel proteins. Electrophysiology techniques include electrical recording techniques that enable the measurement of the flow of ions (as measured by ion current), including in in vitro assays with cells. For example, as disclosed herein, methods for determining the activity of compounds to inhibit hERG, for example, by measuring currents, may use electrophysiology techniques, including patch clamp techniques.

As used herein, "patch clamp technique" refers to use of electrophysiology measurements to detect the passage and/or movement and/or flux of ions through ion channels present on cell membranes with high sensitivity. The passage and/or movement and/or flux of ions through ion channels present on cell surfaces are detected as currents. As used herein, the terms "patch clamp technique," "ion flux technique," "patch clamping," "voltage clamping," "electrophysiology measurements," "patch clamp electrophysiology measurements," and the like, are used interchangeably to refer to "patch clamp technique." Patch clamp technique are useful to measure hERG inhibitory activity in methods as disclosed herein.

As used herein, the term "determine" and grammatical derivatives thereof mean qualitative and/or quantitative determinations, including measuring current, voltage, and the like.

As used herein, the term "modulate" refers to an increase, decrease, or other alteration of any, or all, chemical and biological activities or properties of a hERG polypeptide. The term "modulation" as used herein refers to both upregulation (e.g., activation or stimulation) and downregulation (e.g., inhibition or suppression) of a response.

5.2 Embodiments

Provided herein are genetically engineered (e.g., transfected or transduced) hERG -expressing cells or cell lines comprising recombinant human cardiomyocytes and cell lines overexpressing hERG. Also provided herein are methods of preparing recombinant cardiomyocytes or cardiomyocyte cell lines overexpressing hERG, including cardiomyocytes transduced with a vector encoding hERG. Further provided herein are methods of using recombinant cardiomyocytes or cardiomyocyte cell lines.

Provided herein are recombinant cardiomyocytes and recombinant cell lines overexpressing hERG and uses thereof. The recombinant cardiomyocytes or cardiomyocyte cell lines are more physiologically relevant in methods for determining cardiotoxicity, including drug-induced cardiotoxicity, than other cells and cell lines such as Chinese hamster ovary (CHO) or human embryonic kidney (HEK). Such recombinant cardiomyocytes or cardiomyocyte cell lines are also advantageous as compared with primary cells and cell cultures (e.g., primary cardiac cells, primary stem cells, etc.) in methods for determining cardiotoxicity, including drug-induced cardiotoxicity Recombinant cardiomyocytes or cardiomyocyte cell lines, as provided herein, are particularly advantageous in methods for determining cardiotoxicity, including drug-induced cardiotoxicity, because they possess multiple utilities, including to assess toxicity as well as mechanisms of toxicity as measured, for example, by (i) hERG inhibitory activity, (ii) reduction in cell viability, and (iii) ultrastructural changes in cells, including, for example, changes to cytoskeleton, nucleus, mitochondria, golgi, and other subcellular compartments. Thus, a hERG-overexpressing cell line (e.g., cells from those deposited as ATCC Designation No. PTA-123324, or progeny, derivatives, or descendants from the cells, including from culturing PTA-123324 cells to obtain progeny, derivative, or descendant cells) is simultaneously useful in various assays to measure not only hERG inhibitory activities and reductions in cell viability, but also cell ultrastructural changes to assess mechanisms of toxicity. The use of such a cell line presents a more efficient and economical way of assessing cardiotoxicity, including drug-induced cardiotoxicity.

Recombinant cardiomyocytes or cardiomyocyte cell lines, as provided herein, have many advantages for identifying compounds with hERG inhibitory activity. The recombinant cardiomyocytes or cardiomyocyte cell lines as provided herein perform well using electrophysiology techniques, including manual patch clamping and high throughput automated patch clamping to test current. Moreover, the recombinant cardiomyocytes or cardiomyocyte cell lines as provided herein perform well over a surprisingly wide range of temperatures ranging from physiological temperature to room temperature (e.g., 37° C. and 25° C.). The IKr current in the present recombinant cardiomyocytes or cardiomyocyte cell lines are unexpectedly useful for testing at physiological temperature.

5.2.1. hERG Polypeptides and hERG Genes

The hERG1 ion channel (also referred to as KCNH2 or Kv11.1) is a key element for the rapid component of the delayed rectified potassium currents ($I_{Kr}$) in cardiac myocytes, required for the normal repolarization phase of the cardiac action potential (Curran et al. (1995) *Cell* 80: 795-803; Tseng (2001) *J. Mol. Cell. Cardiol.* 33: 835-49; Vandenberg et al. (2001) *Trends. Pharm. Sci.* 22: 240-246). Loss of function mutations in hERG1 cause increased duration of ventricular repolarization, which leads to prolongation of the time interval between Q and T waves of the body surface electrocardiogram (long QT syndrome-LQTS) (Splawski et al. (2000) *Circulation* 102: 1178-1185; Witchel et al. (2000) *Clin. Exp. Pharmacol. Physiol.* 27: 753-766). LQTS leads to serious cardiovascular disorders, such as tachyarrhythmia and sudden cardiac death.

A human form of the erg gene, hERG (Genbank Accession Number U04270), which encodes hERG potassium ion channel subunits was first described by Warmke & Ganetzky (Warmke & Ganetzky (1994) *Proc. Natl. Acad. Sci. U.S.A.* 91: 3438-3442), incorporated herein by reference. An exemplary hERG polypeptide sequence is set forth in GenBank Accession Number BAA37096, and an exemplary hERG nucleic acid sequence is set forth in GenBank Accession Number SEG_AB00905S.

Figure 1:
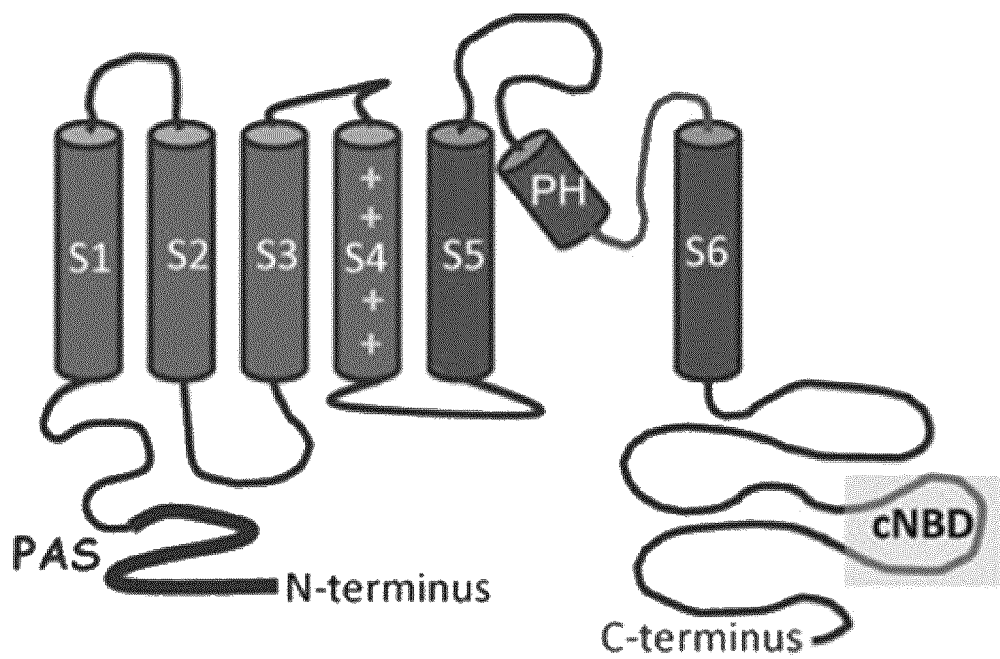

HERG channel may comprise four identical monomer α-subunits, which form the channel's pore through the plasma membrane. Such a hERG tetramer is formed by coassembly of four monomer α-subunits, each of which has six transmembrane spanning α-helical segments (S1-S6), a pore helix situated between S5 and S6, and cytoplasmically located N- and C-termini. Within each hERG subunit, S1-S4 helices form a voltage sensor domain (VSD) that senses transmembrane potential and is coupled to a central $K^+$-selective pore domain (see, e.g., FIG. 1). Each pore domain is comprised of an outer helix (S5) and inner helix (S6) that together coordinate a pore helix and selectivity filter. The carboxy end of the pore helix and selectivity filter contain a highly conserved K channel signature sequence, which in hERG is Thr-Ser-Val-Gly-Phe-Gly. This sequence forms a narrow conduction pathway at the extracellular end of the pore in which K ions are coordinated by a backbone carbonyl oxygen atoms of the signature sequence residues.

Movements of the voltage-sensor domain enable a pore domain to open and close in response to changes in membrane potential. A drug binding site is contained within the central pore cavity of the pore domain, located below the selectivity filter and flanked by the four S6 helices of the tetrameric channel. Without being limited by any theory, inhibiting by blocking or obstructing, either fully or partially, of a central pore cavity or channel of hERG by a compound is a predictor of cardiotoxicity of the compound. Undesired blockade of $K^+$ ion flux in hERG by a compound can lead to long QT syndrome, eventually inducing fibrillation and arrhythmia. Long QT syndrome is a group of disorders that increase the risk for sudden death due to an abnormal heartbeat. The QT refers to an interval between two points (Q and T) on the common electrocardiogram (ECG, EKG) used to record the electrical activity of the heart. This electrical activity, in turn, is the result of ions such as sodium and potassium passing through ion channels in the membranes surrounding heart cells. A prolonged QT interval indicates an abnormality in electrical activity that leads to irregularities in heart muscle contraction. One of these irregularities is a specific pattern of very rapid contractions (tachycardia) of the lower chambers of the heart called torsade de pointes, a type of ventricular tachycardia. The rapid contractions, which are not effective in pumping blood to the body, result in a decreased flow of oxygen-rich blood to the brain. This can result in a sudden loss of consciousness (syncope) and death. hERG blockade is a significant problem experienced during the course of many drug discovery and/or drug development programs.

In some embodiments, a hERG gene as provided herein is the hERG gene of chromosome 7q36.1. In some embodiments, a hERG polypeptide sequence to be expressed in recombinant cardiomyocytes comprises a polypeptide comprising an amino acid sequence identical or substantially identical with amino acids 1-1159 of the amino acid sequence as set forth in SEQ ID NO: 1 (see, e.g., FIG. 2). In some embodiments, a hERG polypeptide sequence comprises an amino acid sequence identical or substantially identical to the amino acid sequence as set forth in SEQ ID NO: 1, which includes a tag sequence. The sequence optionally includes a linker sequence, as shown in FIG. 2. In some embodiments, a hERG polypeptide sequence optionally comprises additional sequences including, for example, regulatory sequences, selectable marker sequences, and/or tag sequences. In some embodiments, an amino acid sequence substantially identical with the amino acid sequence as set forth in SEQ ID NO: 1, or optionally with amino acids 1-1159 of the amino acid sequence as set forth in SEQ ID NO: 1, has an amino acid sequence of about 90% or more identity with the amino acid sequence as set forth in SEQ ID NO: 1, or optionally with amino acids 1-1159 of the amino acid sequence as set forth in SEQ ID NO: 1, wherein the polypeptide has hERG activity. In some embodiments, an amino acid sequence substantially identical with the amino acid sequence as set forth in SEQ ID NO: 1, or optionally with amino acids 1-1159 of the amino acid sequence as set forth in SEQ ID NO: 1, has an amino acid sequence of about 95% or more identity with the amino acid sequence as set forth in SEQ ID NO: 1, or optionally with amino acids 1-1159 of the amino acid sequence as set forth in SEQ ID NO: 1, wherein the polypeptide has hERG activity. In some embodiments, an amino acid sequence substantially identical with the amino acid sequence as set forth in SEQ ID NO: 1, or optionally with amino acids 1-1159 of the amino acid sequence as set forth in SEQ ID NO: 1, has an amino acid sequence of about 98% or more identity with the amino acid sequence as set forth in SEQ ID NO: 1, or optionally with amino acids 1-1159 of the amino acid sequence as set forth in SEQ ID NO: 1, wherein the polypeptide has hERG activity. An exemplary amino acid sequence substantially identical with the amino acid sequence as set forth in SEQ ID NO: 1, or optionally with amino acids 1-1159 of the amino acid sequence as set forth in SEQ ID NO: 1, has an amino acid sequence of about 90%, 91%, 92%, 93%, 94%, 95%, 96%, 97%, 98% or 99% identity with the amino acid sequence as set forth in SEQ ID NO: 1, or optionally with amino acids 1-1159 of the amino acid sequence as set forth in SEQ ID NO: 1, wherein the polypeptide has hERG activity. In some embodiments, examples of the amino acid sequence substantially identical with the amino acid sequence as set forth in SEQ ID NO: 1, or optionally with amino acids 1-1159 of the amino acid sequence as set forth in SEQ ID NO: 1, include an amino acid sequence having mutations such as deletion, substitution or addition in one or a plurality of (e.g., one or more) amino acids, wherein the polypeptide has hERG activity.

In some embodiments, a hERG polypeptide sequence to be expressed in recombinant cardiomyocytes or cardiomyocyte cell lines as provided herein comprises a polypeptide comprising an amino acid sequence as set forth in SEQ ID NO: 1 which has mutations such as deletion, substitution or addition in one or a plurality of (e.g., one or more) amino acids, or a combination thereof. In some embodiments, a hERG polypeptide sequence to be expressed in recombinant cardiomyocytes or cardiomyocyte cell lines as provided herein comprises a polypeptide comprising an amino acid sequence as set forth in SEQ ID NO: 1 in which one to five amino acids are deleted. In some embodiments, a hERG polypeptide sequence to be expressed in recombinant cardiomyocytes or cardiomyocyte cell lines overexpressing hERG as provided herein comprises a polypeptide comprising an amino acid sequence as set forth in SEQ ID NO: 1 to which one to five amino acids are added. In some embodiments, a hERG polypeptide sequence to be expressed in recombinant cardiomyocytes or cardiomyocyte cell lines overexpressing hERG as provided herein comprises a polypeptide comprising an amino acid sequence as set forth in SEQ ID NO: 1 into which one to five amino acids are inserted. In some embodiments, a hERG polypeptide sequence to be expressed in human cardiomyocytes comprise a polypeptide comprising an amino acid sequence as set forth in SEQ ID NO: 1 in which one to five amino acids are substituted with other amino acids. A mutant polypeptide comprising an amino acid sequence having deletion, insertion, substitution or addition of one or a plurality of amino acids and retains the same biological activity of the original (e.g., non-mutated) polypeptide is also included in the scope of the present disclosure. A mutant hERG may comprise such a mutant polypeptide.

Substitution of amino acids refers to a mutation in which one or more amino acid residues in an amino acid sequence are replaced with other amino acids. In some embodiments, a conservative substitution is made in an modification of the amino acid sequence encoded by the hERG gene. A conservative substitution refers to a change in a sequence so that the changed sequence encodes an amino acid similar to the replaced amino acid. Amino acids may be classified into non-polar amino acids (Ala, Ile, Leu, Met, Phe, Pro, Trp, Val), uncharged amino acids (Asn, Cys, Gln, Gly, Ser, Thr, Tyr), acidic amino acids (Asp, Glu), basic amino acids (Arg, His, Lys), neutral amino acids (Ala, Asn, Cys, Gln, Gly, Ile, Leu, Met, Phe, Pro, Ser, Thr, Trp, Tyr, Val), aliphatic amino acids (Ala, Gly), branched amino acids (Ile, Leu, Val), hydroxylamino acids (Ser. Thr), amidic amino acids (Gln, Asn), sulfo-amino acids (Cys, Met), aromatic amino acids (His, Phe, Trp, Tyr), heterocyclic amino acids (His, Trp), imino acids (Pro, 4Hyp) and so on. For example, substitutions between Ala, Val, Leu and Ile, between Ser and Thr, between Asp and Glu, between Asn and Gln, between Lys and Arg, and between Phe and Tyr can be used for retaining the nature of the protein. The number and sites of amino acids to be mutated are not particularly limited.

Polynucleotides encoding an amino acid sequence as set forth in SEQ ID NO: 1 having deletion, insertion, substitution or addition of one or a plurality of amino acids can be prepared according to methods such as site-specific mutagenesis described, for example, in "Molecular Cloning, A Laboratory Manual 2nd ed." (Cold Spring Harbor Press (1989)), "Current Protocols in Molecular Biology" (John Wiley & Sons (1987-1997); especially in Section 8.1-8.5), Hashimoto-Goto et al. (1995) *Gene* 152: 271-5, Kunkel (1985) *Proc. Natl. Acad. Sci. USA* 82: 488-92, Kramer and Fritz (1987) *Method. Enzymol.* 154: 350-67, and Kunkel (1988) *Method. Enzymol.* 85: 2763-6.

Introduction of mutations into polynucleotides may be performed by known methods such as the Kunkel method or the Gapped duplex method using, for example, QuikChange™ Site-Directed Mutagenesis Kit (Stratagene), GeneTailor™ Site-Directed Mutagenesis System (Invitrogen), or TaKaRa Site-Directed Mutagenesis System (In-Fusion® HD Mutagenesis, Mutan-K, Mutan-Super Express Km).

Amino acid residues composing a polypeptide as provided herein may be either naturally occurring amino acid residues or modified amino acid residues. Specific examples of modification of amino acid residues include acylation, acetylation, amidation, arginylation, GPI anchor formation, cross-linking, γ-carboxylation, cyclization, formation of covalent bridges, glycosylation, oxidation, covalent bonding to lipid or fat derivatives, formation of disulfide bonds, selenoylation, demethylation, degradation treatment of proteins, covalent bonding to nucleotides or nucleotide derivatives, hydroxylation, formation of pyroglutamate, covalent bonding to flavin, prenylation, covalent bonding to heme moieties, covalent bonding to phosphatidylinositol, formylation, myristoylation, methylation, ubiquitination, iodination, racemization, ADP-ribosylation, sulfation and phosphorylation.

In some embodiments, a polypeptide as provided herein encompasses fusion proteins where other peptide sequences have been added. Peptide sequences to be added to a polypeptide comprising tag sequences as provided herein (e.g., FLAG tag) may be selected from sequences that make discrimination of a fusion protein easy or sequences that give stability when a fusion protein is expressed by recombinant DNA technology (e.g., influenza hemagglutinin (HA), glutathione S transferase (GST), substance P, multiple histidine tag (6×His, 10×His, etc.), protein C fragment, maltose binding protein (MBP), immunoglobulin constant region fragment, α-tubulin fragment, β-galactosidase, B-tag, c-myc fragment, E-tag (epitope on monoclonal phage), FLAG (Hopp et al. (1988) *Bio/Technol.* 6: 1204-10), lck tag, p18 HIV fragment, HSV-tag (human herpes simplex virus glycoprotein), SV40T antigen fragment, T7-tag (T7 gene10 protein), VSV-GP fragment (Vesicular stomatitis virus glycoprotein), etc).

In some embodiments, a polypeptide as provided herein is a polypeptide which comprises an amino acid sequence as set forth in SEQ ID NO: 1 (alternatively, amino acids 1-1159 of the amino acid sequence as set forth in SEQ ID NO: 1), or an amino acid sequence substantially identical with the amino acid sequence as set forth in SEQ ID NO: 1 (alternatively, amino acids 1-1159 of the amino acid sequence as set forth in SEQ ID NO: 1), and has a hERG activity substantially identical (e.g., physiochemically or pharmacologically) with the hERG activity possessed by a polypeptide comprising the amino acid sequence as set forth in SEQ ID NO: 1 (alternatively, amino acids 1-1159 of the amino acid sequence as set forth in SEQ ID NO: 1). A hERG gene refers to a polynucleotide comprising a nucleic acid sequence encoding hERG. A hERG gene as provided herein encompasses a polynucleotide comprising a nucleic acid sequence identical or substantially identical with the nucleic acid sequence as set forth in SEQ ID NO: 2 (GenBank Accession No. U04270 and see FIG. 3). For example, in addition to polynucleotides encoding the amino acid sequence as set forth in SEQ ID NO: 2, a polynucleotide encoding a mutant polypeptide comprising an amino acid sequence as set forth in SEQ ID NO: 1 having deletion, insertion, substitution or addition of one or plurality of amino acids and has hERG activity may also be used.

A hERG gene as provided herein encompasses genetic polymorphisms of a nucleic acid sequence as set forth in SEQ ID NO: 2. A genetic polymorphism may be easily known by using databases such as GenBank (http://www.ncbi.nlm.nih.gov). Genetic polymorphism includes single nucleotide polymorphism (SNP) and polymorphism caused by a varied number of nucleic acid sequence repeats. Polymorphism caused by deletion or insertion of a plurality of nucleotides (e.g., two to several tens of nucleotides) is also included in genetic polymorphism. For example, polymorphism where a sequence of two to several tens of nucleotides is repeated is also included in genetic polymorphism. Examples of polymorphisms include VNTR (variable number of tandem repeat) (repeat unit composed of several to several tens of nucleotides) and micro-satellite polymorphism (repeat unit composed of about two to four nucleotides).

In some embodiments, a hERG gene as provided herein includes a nucleic acid sequence encoding an amino acid sequence as set forth in SEQ ID NO: 2. A nucleic acid sequence encoding such an amino acid sequence encompasses, in addition to the nucleic acid sequence as set forth in SEQ ID NO: 2, nucleic acid sequences which are different from SEQ ID NO: 2, for example, due to degeneracy of the genetic code. A nucleic acid sequence as set forth in SEQ ID NO: 2 from which non-coding regions are removed may also be used. When a polynucleotide as provided herein is used for expressing a polypeptide by genetic engineering techniques, a nucleic acid sequence with high expression efficiency may be selected and designed in view of codon usage frequency in a cell to be used for expression (Grantham et al. (1981) *Nucleic Acids Res.* 9: 43-74).

In some embodiments, a hERG gene as provided herein encompasses a polynucleotide that hybridizes to a nucleic acid sequence as set forth in SEQ ID NO: 2 or a sequence complementary thereto under stringent conditions and encodes a polypeptide having hERG activity. Examples of such a polynucleotide include isoforms, alternative isoforms and allelic mutants; these are included in a hERG gene as provided herein. Such hERG genes may be obtained from human cDNA libraries or genomic libraries by a known hybridization method, such as colony hybridization, plaque hybridization or Southern blotting, using a polynucleotide comprising the nucleic acid sequence as set forth in SEQ ID NO: 2 or a fragment thereof as a probe. For methods for preparing cDNA libraries, see "Molecular Cloning, A Laboratory Manual 2nd Ed." (Cold Spring Harbor Press (1989)). Alternatively, commercial cDNA libraries or genomic libraries may be used.

In some embodiments, preparation of a cDNA library can be performed as follows: total RNA is prepared from a cell, organ or tissue that is expressing a hERG gene as provided herein by a known method such as the guanidine ultracentrifugation method (Chirwin et al. (1979) *Biochemistry* 18: 5294-9) or the AGPC method (Chomczynski and Sacchi (1987) *Anal. Biochem.* 162: 156-9). Then, mRNA can be purified therefrom by using mRNA Purification Kit (Pharmacia) or the like. Alternatively, a kit such as Quick Prep mRNA Purification Kit (Pharmacia) can be used to prepare mRNA directly from cells, organs or tissues. Subsequently, cDNA can be synthesized from the resultant mRNA with a reverse transcriptase. A cDNA synthesis kit such as AMV Reverse Transcriptase First-Strand cDNA Synthesis Kit (Seikagaku Corporation) can also be used. Alternatively, cDNA can be synthesized and amplified by 5'-RACE method utilizing PCR (Frohman et al. (1988) *Proc. Natl. Acad. Sci. USA* 85: 8998-9002; Belyaysky et al. (1989) *Nucleic Acids Res.* 17: 2919-32). It is also possible to employ a known technique such as oligo-capping method (Maruyama and Sugano (1994) *Gene* 138: 171-4; Suzuki (1997) *Gene* 200: 149-56) in order to prepare a cDNA library with a high full-length cDNA ratio. A cDNA obtained as described above can be incorporated into an appropriate vector. cDNA can be also synthesized directly by concatenating oligo nucleotide sequences.

Stringent conditions as provided herein can be, for example, (2×SSC, 0.1% SDS, 50° C.), (2×SSC, 0.1% SDS, 42° C.) or (1×SSC, 0.1% SDS, 37° C.); more stringent conditions can be, for example, (2×SSC, 0.1% SDS, 65° C.), (0.5×SSC, 0.1% SDS, 42° C.) or (0.2×SSC, 0.1% SDS, 65° C.). More specifically, hybridization using Rapid-hyb buffer (Amersham Life Science) can be performed as described below, for example. Pre-hybridization can be performed at 68° C. for more than 30 min; then, a probe can be added to a hybridization solution, which is retained at 68° C. for more than 1 hr to allow hybrid formation; then, washing can be carried out in 2×SSC, 0.1% SDS at room temperature for 20 min three times, in 1×SSC, 0.1% SDS at 37° C. for 20 min three times, and finally in 1×SSC, 0.1% SDS at 50° C. for 20 min two times. Alternatively, for example, pre-hybridization can be performed in ExpressHyb™ Hybridization Solution (CLONTECH) at 55° C. for more than 30 min; a labeled probe can be added to the solution, which is incubated at 37-55° C. for more than 1 hr; then, washing can be carried out in 2×SSC, 0.1% SDS at room temperature for 20 min three times and in 1×SSC, 0.1% SDS at 37° C. for 20 min once. It is possible to make hybridization conditions more stringent, for example, by raising the temperature of pre-hybridization, hybridization or second washing. For example, it is possible to set temperature of pre-hybridization and hybridization at 60° C., or at 68° C. for more stringent conditions. Those skilled in the art can appropriately select salt concentration and temperature of a buffer, as well as concentration and length of a probe, reaction time, etc., to thereby set conditions for obtaining polynucleotides encoding a hERG gene as provided herein.

For detailed procedures of hybridization, see "Molecular Cloning, A Laboratory Manual 2nd ed." (Cold Spring Harbor Press (1989); especially Section 9.47-9.58), "Current Protocols in Molecular Biology" (John Wiley & Sons (1987-1997); especially Section 6.3-6.4), "DNA Cloning 1: Core Techniques, A Practical Approach 2nd ed." (Oxford University (1995); especially, see Section 2.10 for conditions), and so forth. Examples of polynucleotides which hybridize to a nucleic acid sequence as set forth in SEQ ID NO: 2 or a sequence complementary thereto include polynucleotides comprising a nucleic acid sequence having 50% or more, preferably 70% or more, more preferably 80% or more, still more preferably 90% or more (e.g., 95% or more, or 99% or more) identity to the nucleic acid sequence as set forth in SEQ ID NO: 2. Such identity can be determined with BLAST algorithm (Altschul, (1990) *Proc. Natl. Acad. Sci. USA* 87: 2264-8; Karlin and Altschul, (1993) *Proc. Natl. Acad. Sci. USA* 90: 5873-7). Among programs based on this algorithm, there are programs for determining identity in sequences. BLASTX for amino acid sequence and BLASTN (Altschul et al. (1990) *J. Mol. Biol.* 215: 403-10) for nucleic acid sequences have been developed and are available to the sequences of the present disclosure. For specific analyzing methods, see, for example, http://www.ncbi.nlm.nih.gov.

Genes whose structure and function are similar to those of hERG, such as isoforms or allelic mutants of hERG, (such genes are included in a hERG gene as provided herein) may be obtained from human cDNA library or genomic library by using primers designed based on a nucleic acid sequence as set forth in SEQ ID NO: 2 and a gene amplification technique (PCR) (Current Protocols in Molecular Biology, John Wiley & Sons (1987) Section 6.1-6.4).

Polynucleotides as provided herein encompass polynucleotides encoding an amino acid sequence as set forth in SEQ ID NO: 2 having deletion, insertion, substitution or addition of one or a plurality of amino acids, or sequences complementary to the sequences of these polynucleotides. These polynucleotides of the present disclosure can be prepared according to the site-specific mutagenesis method or the like described in "Molecular Cloning, A Laboratory Manual 2nd ed." (Cold Spring Harbor Press (1989)), "Current Protocols in Molecular Biology" (John Wiley & Sons (1987-1997); especially Section 8.1-8.5), Hashimoto-Goto et al. (1995) *Gene* 152: 271-5, Kunkel (1985) *Proc. Natl. Acad. Sci. USA* 82: 488-92, Kramer and Fritz (1987) *Method. Enzymol.* 154: 350-67, Kunkel (1988)*Method. Enzymol.* 85: 2763-6, etc. Commercial kits can be used for mutagenesis.

Confirmation of a nucleic acid sequence of a polynucleotide as provided herein can be performed by sequencing using conventional methods. For example, the dideoxynucleotide chain termination method (Sanger et al. (1977) *Proc. Natl. Acad. Sci. USA* 74: 5463) can be used. Alternatively, a sequence can be analyzed with an appropriate DNA sequencer. In some embodiments, the sequencing methodology can be sequencing-by-synthesis (SBS). In SBS, extension of a nucleic acid primer along a nucleic acid template (e.g. a target nucleic acid or amplicon thereof) can be monitored to determine the sequence of nucleotides in the template. The underlying chemical process can be polymerization (e.g. as catalyzed by a polymerase enzyme). In a particular polymerase-based SBS embodiment, fluorescently labeled nucleotides can be added to a primer (thereby extending the primer) in a template dependent fashion such that detection of the order and type of nucleotides added to the primer can be used to determine the sequence of the template.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi et al. (1996) *Analytical Biochemistry* 242 (1): 84-9; Ronaghi (2001) *Genome Res.* 11(1): 3-11; Ronaghi et al. (1998) *Science* 281(5375): 363; U.S. Pat. Nos. 6,210,891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be adapted for application of pyrosequencing to amplicons produced according to the present disclosure are described, for example, in PCT/US11/57111, US 2005/0191698 A1, U.S. Pat. Nos. 7,595,883, and 7,244,559, each of which is incorporated herein by reference.

5.2.2. Vectors

In some embodiments, a nucleic acid representing at least part of a hERG gene has been transferred with a vector to human cardiomyocytes. Such transfer is referred to as transfection or transduction.

The type of vector used in the method is not limited. In some embodiments, the vector is a viral vector and the transfer is by transduction. In some embodiments, the vector is a non-viral vector and the transfer is by transfection. Non-viral transfection can be facilitated by a number of techniques, including without limitation electroporation or the use of chemical transfection agents known in the art.

In some embodiments, viral vectors containing a hERG gene (e.g., a nucleic acid sequence encoding hERG) are provided. In some embodiments, the viral vector used herein was engineered by using a virus-derived nucleic acid sequence so that it is capable of integrating any nucleic acid sequence into any cell. A viral vector is useful in retaining a hERG gene as provided herein within host cells and allowing expression of a hERG polypeptide encoded by a hERG gene.

In some embodiments, the viral vector is a retroviral vector, such as a lentiviral vector. Retrovirus refers to any virus belonging to the genus Oncovirus in the subfamily Oncovirinae in the family Retroviridae, and lentivirus refers to any virus belonging to the genus Lentivirus in the subfamily Lentivirinae in the family Retroviridae. In some embodiments, the viral vector is a lentiviral vector. In a some embodiments, an exemplary lentiviral vector as provided herein is shown in exemplary FIG. 4A.

In some embodiments, a retroviral vector is a kind of recombinant retrovirus such as the Moloney murine leukemia virus. Moloney murine leukemia virus has the ability to integrate into the host genome in a stable fashion, and contain a reverse transcriptase that allows integration into a host genome. In some embodiments, a retroviral vector as provided herein is replication-competent. In some embodiments, a retrovial vector as provided herein is replication-defective. In some embodiments, replication defective retrovial vectors are used since they are capable of infecting their target cells and delivering their viral payload, but then fail to continue the typical lytic pathway that leads to cell lysis and death.

In some embodiments, a viral vector is a lentiviral vector, which is a subclass of retroviral vectors. Lentiviral vectors have been adapted to integrate into the genome of non-dividing cells. In some embodiments, a viral genome in the form of RNA is reverse-transcribed when the virus enters the cell to produce DNA, which is then inserted into a genome by the viral integrase enzyme. Such as a vector can remain in the genome and passed on to the progeny of the cell when it divides.

Exemplary retroviral vectors include, but not limited to, pZIPneo (Cepko, C. L. et al. (1984) *Cell.* 37: 1053-1062), pBabePuro (Morgenstern, J. P. and Land, H., *Nucleic Acids Res.* 18: 3587-3596), pCLXSN (IMGENEX, catalog #10041P), ViraPort retroviral gene expression system (Stratagene, catalog #217563), pDON-Al (Takara, catalog #3650) and lentiviral vectors such as pLenti6N5-GW/lacZ (Invitrogen, Carlsbad, Calif., catalog #K4955-10). In some embodiments, viral vectors prepared from viruses other than retrovirus and lentivirus may also be used, e.g., vectors prepared from adenovirus, adeno-associated virus, Sinbis virus, Sendai virus, togavirus, paramyxovirus, poxvirus, poliovirus, herpesvirus and vaccinia virus.

In some embodiments, a retroviral vector is a Vesicular stomatitis virus-G protein (VSV-G) pseudotyped retroviral vector. The term "pseudotyped" or "pseudo" refers to a phenomenon in which the genome of one virus is budding surrounded by the envelope protein of other virus (Zavada (1972) *J. Gen. Virol.* 15: 183-191). Vesicular stomatitis virus (VSV) is a virus belonging to the family Rhabdoviridae and having a negative single-stranded RNA genome. It is believed that the receptor of its envelope protein (G protein) on the cell side is an anionic lipid such as phosphatidylserine (Schlegel et al. (1983) *Cell* 32: 639-646; Mastromarino et al.

(1987) *J. Gen. Virol.* 68: 2359-2369). It is reported that VSV-G pseudotyped retroviral vector has an extremely broad host range compared to conventionally used amphotropic retroviral vectors (Emi et al. (1991) *Proc. Natl. Acad. Sci. USA.* 65: 1202-1207; Arai et al. (1999) *Virol.* 260: 109-115) and that its gene transfer ability can be improved by ultracentrifugation (Burns et al. (1993) *Proc. Natl. Acad. Sci. USA,* 90: 8033-8037). Therefore, by preparing a pseudotyped retrovirus having this VSV-G gene product as an envelope protein, it becomes possible to transfer the hERG gene into various cells more efficiently than achieved by retroviruses having their innate envelope protein. The nature of these VSV-G pseudotyped vectors is the same in lentiviral vectors, and a large number of lentiviral vectors reported are pseudotyped vectors of this kind (Kay et al. (2001) *Nature Med.* 7:33-40), and can be used in the present disclosure.

In some embodiments, a viral vector is linked to downstream region of regulatory sequences so that it comes to enable the expression of a hERG gene as provided herein in a host cardiomyocyte cell into which the viral vector has been introduced. The "regulatory sequences" include promoter and terminator, and optionally include trans-activator, transcription factor, poly-A signals that stabilizes transcript, splicing and polyadenylation signals, and the like. These regulatory sequences contain components necessary for expression of the polynucleotide linked thereto.

In some embodiments, a viral vector as provided herein can contain selectable markers. Exemplary selectable markers include drug resistance genes (neomycin resistance gene, hygromycin resistance gene, puromycin resistance gene, etc.) and fluorescent proteins (GFP, EGFP, etc.). In some embodiments, a signal peptide can be integrated that is useful for directing the intracellularly expressed polypeptide onto cell membranes into a viral vector so that the signal peptide is added to the polypeptide. Further, in some embodiments, addition of linker and insertion of initiation codon (ATG) and termination codon (TAA, TAG or TGA) can be performed.

In some embodiments, when a mammalian cell or other animal cell is used as a host, adenovirus late promoter (Kaufman et al. (1989) *Mol. Cell. Biol.* 9: 946), CAG promoter (Niwa et al. (1991) *Gene* 108: 193-200), CMV immediate early promoter (Seed and Aruffo (1987) *Proc. Natl. Acad. Sci. USA* 84: 3365-9), EF1α promoter (Mizushima et al. (1990) *Nucleic Acids Res.* 18: 5322; Kim et al. (1990) *Gene* 91: 217-23), HSV TK promoter, SRα promoter (Takebe et al. (1988) *Mol. Cell. Biol.* 8: 466), SV40 promoter (Mulligan et al. (1979) *Nature* 277: 108), SV40 early promoter (Genetic Engineering Vol. 3, Williamson ed., Academic Press (1982) pp. 83-141), SV40 late promoter (Gheysen and Fiers (1982) *J. Mol. Appl. Genet.* 1: 385-94), RSV (Rous sarcoma virus)-LTR promoter (Cullen (1987) *Methods Enzymol.* 152: 684-704), MMLV-LTR promoter, CMV enhancer, SV40 enhancer, cPPT (central polypurine tract) sequence, globin intron, etc. may be used.

Insertion of a hERG gene into a viral vector can be performed by ligase reaction. Restriction enzyme sites can also be used (Current Protocols in Molecular Biology, John Wiley & Sons (1987) Section 11.4-11.11; Molecular Cloning, A Laboratory Manual 2nd ed., Cold Spring Harbor Press (1989) Section 5.61-5.63).

In some embodiments, to produce a lentivirus, several vectors (e.g., plasmids) can be transfected into a so-called packaging cell line, such as HEK 293. For example, one or more packaging plasmids, generally referred to as packaging plasmids, encode virion proteins, such as the capsid and the reverse transcriptase. Another plasmid can contain the genetic material to be delivered. In some embodiments, it can transcribed to produce a single-stranded RNA viral genome and is marked by the presence of a Ψ (psi) sequence. This sequence can be used to package the genome into the virion.

The term "viral vector," as used herein, refers to a vector (e.g., plasmid) comprising viral sequences such as viral promoter sequences. A viral vector, such as a lentiviral vector, can be introduced into a packaging cell. A packaging cell such as HEK 293 cell or the like can be used. A viral vector can be introduced into a packaging cell by various methods such as an adenovirus method, electroporation (Cytotechnology 3: 133 (1990)), a cationic liposome method (cationic liposome DOTAP (Boehringer Mannheim), etc.), a method using a positively charged polymer, an electrostatic type liposome method, a internal type liposome method, particle gun bombardment, a liposome method, lipofection (*Proc. Natl. Acad. Sci. USA* 84: 7413 (1987) (e.g., lipofectamine 2000 (Invitrogen), Fugene 6 (Roche Diagnostics), etc.)), a calcium phosphate method (JP 2-227075 A), receptor-mediated gene transfer, a retrovirus method, a DEAE dextran method, a virus-liposome method (Experimental Medicine additional volume "Basic Technology for Gene Therapy", Yodo-sha (1997); Experimental Medicine additional volume "Analytical Experiments on Gene Transfer and Expression", Yodo-sha (1997); *J. Clin. Invest.* 93: 1458-64 (1994); *Am. J. Physiol.* 271: R1212-20 (1996); *Molecular Medicine* 30: 1440-8 (1993); *Experimental Medicine* 12: 1822-6 (1994); *Protein, Nucleic Acid and Enzyme* 42: 1806-13 (1997); *Circulation* 92 (Suppl. II): 479-82 (1995)) and direct transfer of naked-DNA. A commercially available viral vector packaging system can be used (e.g., a LentiPAK™ lentiviral packaging system from GeneCopoeia as described in Example 1).

5.2.3. Cardiomyocyte as Host Cells

In some embodiments, a host cell that expresses hERG as provided herein is a recombinant human cardiomyocyte. In some embodiments, a host cell that expresses hERG as provided herein is a cell derived from human cardiomyocytes. Cardiomyocytes (also known as myocardiocytes or cardiac myocytes) are the muscle cells (myocytes) that make up the cardiac muscle. Each myocardial cell contains myofibrils, which are specialized organelles consisting of long chains of sarcomeres, the fundamental contractile units of muscle cells. Cardiomyocytes show striations similar to those on skeletal muscle cells, but unlike multinucleated skeletal cells, they contain only one nucleus. Cardiomyocytes have a high mitochondrial density, which allows them to produce adenosine triphosphate (ATP) quickly, making them highly resistant to fatigue.

In some embodiments, a human cardiomyocyte cell is an immortalized human cardiomyocyte or an immortalized human cardiomyocyte cell line. In some embodiments, a human cardiomyocyte cell is an immortalized human vascular smooth muscle cell line. In some embodiments, a human cardiomyocyte as provided herein is a human immortalized cell line derived from a post-mitotic primary cell culture. In some embodiments, the post-mitotic cell line is a cardiomyocyte cell line. In another embodiment, the post-mitotic cell line is a vascular smooth muscle cell line. In some embodiments, the post-mitotic cell line is a neuronal cell line. In some embodiments, the post-mitotic cell line is a skeletal myoblast cell line.

In some embodiments, a human cardiomyocyte cell is derived from nonproliferating primary culture. As used herein the term "nonproliferating primary cultures" encompasses cell cultures which become senescent after 2-3 passages (limited passage) and post-mitotic cells in culture. Such cultures also include those cells in culture that have exited the cell cycle and are no longer capable of undergoing mitosis (post-mitotic). As used herein, the term "primary cultures" encompasses cells in culture that have been taken for an organism and not passaged. Primary cultures herein include, but are not limited to, cells in culture originally taken from vascular smooth muscle, skeletal myloblasts, neuronal cells, bone cells (osteoblasts, osteocytes), chondrocytes, and normal cardiomyocytes.

In some embodiments, a cell line integrates functionally with normal or myopathic cardiac tissue as determined by measurement of syncitial beating of the tissue. This syncitial beating can be easily measured in cell culture.

In some embodiments, human cardiomyocytes are from a human ventricular cardiomyocyte cell line. In some embodiments, a human cardiomyocyte cells is from an adult human ventricular cardiomyocyte cell line. In some embodiments, a human cardiomyocyte cell line is AC10 (ATCC Cat. No. PTA-1501). In some embodiments, the human cardiomyocyte cells can be prepared according to the method described in U.S. Pat. No. 7,223,599, which is incorporated herein by reference. Briefly, adult ventricular heart tissue can be obtained from the heart transplantation facility. The ventricular tissue is dissected and minced under a dissection microscope. The tissue is transferred to a glass chamber and extensively trypsinized at 37° C. The enzymatically dissociated cells consisting of a mixture of all the constituent cell types of cardiac tissue are resuspended in DMEM F-12, supplemented with 12.5% Fetal Bovine Serum (FBS) and penicillin-streptomycin and are allowed to attach for an hour. The medium containing a higher concentration of cardiomyocytes that do not attach is transferred to a fresh dish and cultured at 37° C. in 5% $CO_2$. The culture dishes have fibroblasts which are co-cultured with the cardiomyocytes. These fibroblasts are removed by repeated selective plating and by repeated complement fixation using an antibody, 1610, (Sigma Chemical Co.) to the surface protein of fibroblasts (Singer et al. (1989) *J. Invest. Dermatol.* 92:166-170). This resulted in cultures with a high percentage of cardiomyocytes. If the primary cultures stop dividing, an indirect method can be used to transfer a SV-40 gene in order to immortalize the cardiomyocytes. The surviving hybrid cells are plated at low density and subcloned with glass cloning rings (establishing a clone/colony). The clones are grown under selection, and screened for specific cell-type markers by immunocytochemical and molecular genetic analyses to obtain a human cardiomyocyte cell line.

5.2.4. Generation of Recombinant hERG Expressing Cardiomyocytes and Cardiomyocyte Cell Lines In some embodiments, transfer of a hERG gene (e.g., a nucleic acid sequence encoding hERG) into cells can be performed by using a vector as provided herein. In some embodiments, the hERG gene transfer into cells can be performed, for example, by using a viral vector as provided herein.

Gene transfer can be achieved by culturing a host cell, adding a pseudovirus particle to the culture, and culturing further. In some embodiments, a pseudo-lentivirus particle is used. In some embodiments, polybrene (Sigma H9268, also known as hexadimethrine bromide) can be added to a pseudovirus particle to be added to the culture. Twenty-four hours after the addition of the pseudovirus particle, it is preferable to exchange the medium. It is possible to make the expression level per cell highest by culturing the cell for about 72 hours after the medium exchange. Other methods known in the art for gene transfer are included in the present disclosure.

In some embodiments, transfer of a hERG gene (e.g., a nucleic acid sequence encoding hERG) into host cells can be performed using methods as described in Example 2. For example, a cell line expressing hERG can be constructed by transducing adult human ventricular cardiomyocytes cell line with a pseudovirus containing an expression vector that expresses hERG. The expression vector can also contain a reporter gene and confer resistance for positive selection and maintenance. The expression vector can also contain a tag, including a FLAG tag. In some embodiments, transfer of a hERG gene into host cells can be performed by transfection.

In some embodiments, the recombinant cardiomyocytes or cardiomyocyte cell lines as provided herein comprises percentages of hERG-expressing cells. In some embodiments, more than 5% of the recombinant cardiomyocytes in the cardiomyocyte cell line express hERG. In some embodiments, more than 10% of the recombinant cardiomyocytes in the cardiomyocyte cell line express hERG. In some embodiments, more than 20% of the recombinant cardiomyocytes in the cardiomyocyte cell line express hERG. In some embodiments, more than 30% of the recombinant cardiomyocytes in the cardiomyocyte cell line express hERG. In some embodiments, more than 40% of the recombinant cardiomyocytes in the cardiomyocyte cell line express hERG. In some embodiments, more than 50% of the recombinant cardiomyocytes in the cardiomyocyte cell line express hERG. In some embodiments, more than 60% of the recombinant cardiomyocytes in the cardiomyocyte cell line express hERG. In some embodiments, more than 70% of the recombinant cardiomyocytes in the cardiomyocyte cell line express hERG. In some embodiments, more than 80% of the recombinant cardiomyocytes in the cardiomyocyte cell line express hERG. In some embodiments, more than 90% of the recombinant cardiomyocytes in the cardiomyocyte cell line express hERG. In some embodiments, more than 95% of the recombinant cardiomyocytes in the cardiomyocyte cell line express hERG.

In some embodiments, the level of hERG expressed in the recombinant cardiomyocytes as provided herein is 5% to 100% more than level of hERG naturally expressed in a cardiomyocyte. In some embodiments, the level of hERG expressed in the recombinant cardiomyocytes as provided herein is 10% to 100% more than level of hERG naturally expressed in a cardiomyocyte. In some embodiments, the level of hERG expressed in the recombinant cardiomyocytes as provided herein is 2-fold to 100-fold of the level of hERG naturally expressed in a cardiomyocyte. Exemplary level of hERG expressed in the recombinant cardiomyocytes as provided herein is 5%, 10%, 20%, 30%, 40%, 50%, 60%, 70%, 80%, or 90%, more than level of hERG naturally expressed in a cardiomyocyte, or about 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, or 100-fold of the level of hERG naturally expressed in a cardiomyocyte. In some embodiments, the level of hERG naturally expressed in the cardiomyocytes is determined by measuring the level of hERG in the cardiomyocytes prior to the transduction of the viral vector, or prior to the expression of the hERG in the cardiomyocytes via the viral vector.

Recombinant cardiomyocytes and recombinant cell lines overexpressing hERG as provided herein also encompass those cells or cell strains obtained by cell cloning (e.g., subcloning). Further, recombinant cardiomyocytes and recombinant cell lines overexpressing hERG as provided herein also encompass those cells or cell lines that are obtained by transferring an hERG gene again into the cell strain obtained by the cloning.

In some embodiments, recombinant cardiomyocytes and recombinant cell lines overexpressing hERG as provided herein can be subjected to cloning in order to avoid bias in nature during culture and to enable stable evaluation of drugs. Cell cloning can be performed according to conventional methods (e.g., limiting dilution culture method or cell sorting by flow cytometry).

hERG expression levels in the recombinant cardiomyocytes and recombinant cell lines overexpressing hERG as provided herein can be determined by immunohistological analysis methods using anti-hERG antibody. The antibodies can be prepared according to conventional methods. Alternatively, a commercial antibody (such as prepared by Alomene Labs) may be used. Exemplary immunohistological analysis methods include enzyme immunoassay (EIA), radioimmunoassay (RIA), ELISA, Western blotting, flow cytometry, and immunohistochemical staining.

5.2.5 Uses of hERG Expressing Cardiomyocytes and Cardiomyocyte Cell Lines

As shown in the Examples below, recombinant human cardiomyocytes and recombinant cardiomyocyte cell lines overexpressing hERG as provided herein is capable of exhibiting high current with no or minor rundown effect over a relative long time period at 37° C. or room temperature. The advantageous characteristics of such a cell line render it suitable for a range of applications.

In some embodiments, the recombinant human cardiomyocytes overexpressing hERG expressing hERG as provided herein have a peak hERG current as determined by patch clamping with a fully automated high throughput patch clamp system of 7000 pA to 3500 pA. In some embodiments, the recombinant human cardiomyocytes overexpressing hERG as provided herein have a peak hERG current as determined by patch clamping with a fully automated high throughput patch clamp system of 6500 pA or more. In some embodiments, the recombinant human cardiomyocytes overexpressing hERG as provided herein have a peak hERG current as determined by patch clamping with a fully automated high throughput patch clamp system of 6000 pA or more. In some embodiments, the recombinant human cardiomyocytes overexpressing hERG as provided herein have a peak hERG current as determined by patch clamping with a fully automated high throughput patch clamp system of 5500 pA or more. In some embodiments, the recombinant human cardiomyocytes overexpressing hERG as provided herein have a peak hERG current as determined by patch clamping with a fully automated high throughput patch clamp system of 5000 pA or more. In some embodiments, the recombinant human cardiomyocytes overexpressing hERG as provided herein have a peak hERG current as determined by patch clamping with a fully automated high throughput patch clamp system of 4500 pA or more. In some embodiments, the recombinant human cardiomyocytes overexpressing hERG as provided herein have a peak hERG current as determined by patch clamping with a fully automated high throughput patch clamp system of 4000 pA or more.

In some embodiments, the recombinant human cardiomyocytes overexpressing hERG as provided herein have an average hERG current as determined by patch clamping with a fully automated high throughput patch clamp system of 6500 pA to 2500 pA. In some embodiments, the recombinant human cardiomyocytes overexpressing hERG as provided herein have an average hERG current as determined by patch clamping with a fully automated high throughput patch clamp system of 6500 pA or more. In some embodiments, the recombinant human cardiomyocytes overexpressing hERG as provided herein have an average hERG current as determined by patch clamping with a fully automated high throughput patch clamp system of 6000 pA or more. In some embodiments, the recombinant human cardiomyocytes overexpressing hERG as provided herein have an average hERG current as determined by patch clamping with a fully automated high throughput patch clamp system of 5500 pA or more. In some embodiments, the recombinant human cardiomyocytes overexpressing hERG as provided herein have an average hERG current as determined by patch clamping with a fully automated high throughput patch clamp system of 5000 pA or more. In some embodiments, the recombinant human cardiomyocytes overexpressing hERG as provided herein have an average hERG current as determined by patch clamping with a fully automated high throughput patch clamp system of 4500 pA or more. In some embodiments, the recombinant human cardiomyocytes overexpressing hERG as provided herein have an average hERG current as determined by patch clamping with a fully automated high throughput patch clamp system of 4000 pA or more. In some embodiments, the recombinant human cardiomyocytes overexpressing hERG as provided herein have an average hERG current as determined by patch clamping with a fully automated high throughput patch clamp system of 3500 pA or more. In some embodiments, the recombinant human cardiomyocytes overexpressing hERG as provided herein have an average hERG current as determined by patch clamping with a fully automated high throughput patch clamp system of 3000 pA or more. In some embodiments, the recombinant human cardiomyocytes overexpressing hERG as provided herein have an average hERG current as determined by patch clamping with a fully automated high throughput patch clamp system of 2500 pA or more.

In some embodiments, the recombinant human cardiomyocytes overexpressing hERG as provided herein are capable of exhibiting a current that varies by less than about 50%, or alternatively, 45%, or alternatively, 40%, or alternatively, 35%, or alternatively, 30%, or alternatively, 25%, or alternatively, 20%, or alternatively, 15%, or alternatively, 10%, of peak current amplitude over 30 minutes as determined by patch clamping with a fully automated high throughput patch clamp system.

In some embodiments, the recombinant human cardiomyocytes overexpressing hERG as provided herein are capable of exhibiting a current that varies by less than about 50% or alternatively, 45%, or alternatively, 40%, or alternatively, 35%, or alternatively, 30%, or alternatively, 25%, or alternatively, 20%, or alternatively, 15%, or alternatively, 10%, of peak current amplitude over 60 minutes as determined by patch clamping with a fully automated high throughput patch clamp system.

In some embodiments, the current fora compound is measured during the window of about 450-1500 seconds by patch clamping with a fully automated high throughput patch clamp system. In some embodiments, the recombinant human cardiomyocytes overexpressing hERG as provided herein are capable of exhibiting a current that varies by less than about 50% or alternatively, 45%, or alternatively, 40%, or alternatively, 35%, or alternatively, 30%, or alternatively, 25%, or alternatively, 20%, or alternatively, 15%, or alternatively, 10%, of peak current amplitude during 450-1500 seconds {MH}.

Recombinant human cardiomyocytes and recombinant cardiomyocyte cell lines overexpressing hERG as provided herein can be used in a range of applications. Among these applications, of particular value to researchers and drug developers are methods by which a candidate pharmaceutical can be tested for its effect on hERG activity. Since hERG activity is related to long QT (LQT) syndrome, methods as provided herein can assist in the identification of compounds that are likely to give rise to a LQT condition. This ability can minimize the risk to a patient of LQT-related injury. Methods as provided herein can, therefore, be employed in drug design.

Thus, provided herein is a method of measuring hERG current inhibitory activity comprising using the cells or cell lines as provided herein. Also provided herein is a method of screening a compound or a salt thereof for its hERG current altering effect comprising using the cells or cell lines as provided herein.

The following discussion is not meant to be an all-encompassing description of the methods as provided herein. Additionally, although the steps of various methods are disclosed in the context of one single method, it is understood that the general discussion accompanying the methods is intended to apply to disclosed methods. Variations on the disclosed methods can be made fall within the claims and spirit of the present disclosure. Such variations on the disclosed methods will be apparent to those of skill in the art upon contemplation of the present disclosure.

5.2.5.1. Methods for Drug Screening and/or Drug Development

Recombinant human cardiomyocytes and recombinant cardiomyocyte cell lines overexpressing hERG as provided herein can be used in drug screening and development, including for drug-associated cardiotoxicity (e.g., hERG-related cardiotoxicity) that is related to inhibition of (e.g., by blocking or obstructing, either fully or partially) hERG and/or for drug-associated cardiotoxicity (e.g., non-hERG-related cardiotoxicity) that is not specifically related to inhibition of (e.g., by blocking or obstructing, either fully or partially) hERG, as disclosed herein. For any and all of the following methods, the compounds can include novel or previously known drugs.

The methods as provided herein can also be employed to identify the risk of drugs to give rise to arrhythmias, e.g., long QT syndrome (LQT), as measured by inhibition of (e.g., by blocking or obstructing, either fully or partially) hERG. In some embodiments, the methods as provided herein are applied to a candidate pharmaceutical that is in development to assist a drug designer or researcher to identify a candidate pharmaceutical that is likely to give rise to arrhythmias and, if desired, to remove the candidate from the research program, or provide suitable warning to medical practitioners and patients based on data derived from the methods as provided herein.

In some embodiments, the methods as provided herein can be used to identify or screen drugs for their risk of giving rise to LQT. One form of LQT is an inherited cardiac arrhythmia that causes abrupt loss of consciousness, syncope, seizures and sudden death from ventricular tachyarrhythmias, specifically torsade de pointes and ventricular fibrillation (Ward (1964) *J. Ir. Med. Assoc.* 54, 103-106; Romano (1965) *Lancet* 1658-659; Schwartz et al. (1975) *Am. Heart J.* 109: 378-390; Moss et al. (1991) *Circulation* 84: 1136-1144.). This disorder usually occurs in young, otherwise healthy individuals (Ward (1964) *J. Ir. Med. Assoc.* 54: 103-106; Romano (1965) *Lancet* 1658-659; Schwartz et al. (1975) *Am. Heart J.* 109: 378-390). Most LQT gene carriers manifest prolongation of the QT interval on electrocardiograms, a sign of abnormal cardiac repolarization (Vincent et al. (1992) *N. Engl. J. Med.* 327: 846-852).

In some embodiments, the methods as provided herein can be applicable to drugs already in the marketplace to identify drugs that can pose a risk of arrhythmias, e.g., LQT, and can be marked as such.

In some embodiments, the methods as provided herein can be used for screening or selecting compounds from the collections of a chemical or compound library, for example, new drug candidates generated by organic or medicinal chemists as part of a drug discovery and/or drug development program.

In some embodiments, the methods as provided herein can be used to design compounds or drugs with reduced cardiotoxicity or reduced risk to a patient.

5.2.5.2. Methods of Identifying Candidate Compounds as hERG Channel Inhibitors Recombinant human cardiomyocytes and recombinant cardiomyocyte cell lines overexpressing hERG as provided herein can be used in drug screening and development, including for drug-associated cardiotoxicity that is related to inhibition of (e.g., by blocking or obstructing, either fully or partially) hERG. For any and all of the following methods, the compounds can include novel or previously known drugs.

In some embodiments, provided herein are methods of identifying candidate compounds as hERG inhibitors. For example, many therapeutics are hERG inhibitors. While some of these therapeutics were designed as hERG channel inhibitors, others exhibit hERG channel inhibition as an undesired side effect. The cells or cell lines as provided herein can be used to identify a candidate compound as a hERG channel inhibitor.

In some embodiments, the methods as provided herein comprise providing the recombinant human cardiomyocytes and recombinant cardiomyocyte cell lines overexpressing hERG of the present disclosure. A candidate compound can then be contacted with the cells or cell lines. In some embodiments, the contacting can be performed by dripping a solution comprising the candidate compound over the cell(s). For example, the contacting can be performed in a sterile environment and/or an environment in which conditions are controlled and maintained at levels which preserve the integrity of the cell(s). Various methods of contacting can be employed according to the present methods and will be apparent to those of skill in the art upon consideration of the present disclosure. A hERG activity is then determined in the presence of the candidate compound. The method of the determination can be dictated, in part, by the nature of the biological activity. In some embodiments, the biological activity is transport of potassium ions, and transport of potassium ions can be detected via detection of a voltage or current, which can accompany transport of potassium ions. Such a current can be detected, and this biological activity determined by employing a patch clamp apparatus, such as the patch clamp apparatus disclosed herein.

In some embodiments, the biological activity of the hERG potassium channel determined in the presence of the candidate compound can be compared with hERG potassium channel activity determined in an absence of the candidate compound. In some embodiments, the comparison is a quantitative comparison, and can optionally involve a statistical analysis. In some embodiments, the candidate compound can be identified as a hERG channel inhibitor if the biological activity of the hERG potassium channel in the presence of the candidate compound is lower than the biological activity of the hERG potassium channel in the absence of the candidate compound. In some embodiments, hERG current inhibitory activities can be determined by using as an indicator the ratio of the amplitude of hERG current after contacting a compound to the amplitude of hERG current before contacting the compound.

In some embodiments, an extracellular ion concentration or another intervention (such as an applied electric field, or a compound that alters the membrane potential) can be manipulated to set a membrane potential at a level that will likely change when a compound binds to the target hERG channel.

For example, stably-transduced human cardiomyocyte cells can be grown in culture plates and then loaded with a voltage-sensitive dye (e.g., carbocyanides, DiANEPP, diBAC, etc.) with a dynamic range and response time that allows detection of transmembrane voltage. A compound of interest can then be applied to each well of the dish, with the appropriate control also being applied. Transmembrane potential can then be recorded using any of a variety of detection methods, such as automated fluorescence detection for multiple samples (e.g., FLIPR technology). By assessing the effects of varying concentrations of compounds in cells that express hERG, the effect of the compound on hERG biological activity can be assessed.

In some embodiments, when a biological activity is potassium ion transport, the determining can be performed by measuring a voltage or current across the structure. In some embodiments, such measurements are performed by employing patch clamp technology, which is also described elsewhere herein. In some embodiments, patch-clamp experiments can be performed at 37° C. In some embodiments, patch-clamp experiments can be performed at room temperature (21-23° C.).

In some embodiments, for example, the amplitude of the hERG current before the contact with the compound is taken as 100% and 0 nA is taken as 0%. Then, inhibition ratio is calculated from the amplitude of the hERG current after the contact with the compound, followed by determination of the hERG current inhibitory activity of the compound. Further, it is also possible to calculate the inhibitory activity value inherent in the test compound by varying the dose of the compound. In some embodiments, when the concentration of the compound inducing 50% inhibition of hERG currents is at least 0.3 μM or more, the compound can be judged as not affecting hERG currents or not having inhibitory activity. In some embodiments, when the concentration of the compound inducing 50% inhibition of hERG currents is at least 1.0 μM or more, the compound can be judged as not affecting hERG currents or not having inhibitory activity. In some embodiments, when the concentration of the compound inducing 50% inhibition of hERG currents is at least 3.0 μM or more, the compound can be judged as not affecting hERG currents or not having inhibitory activity. In some embodiments, when the concentration of the compound inducing 50% inhibition of hERG currents is at least 10.0 μM or more, the compound can be judged as not affecting hERG currents or not having inhibitory activity. In some embodiments, when the concentration of the compound inducing 50% inhibition of hERG currents is at least 30.0 μM or more, the compound can be judged as not affecting hERG currents or not having inhibitory activity.

"$IC_{50}$" or "$IC_{90}$" may be used in some embodiments to determine the inhibitory effect of the compound. As used herein, the terms "$IC_{50}$" and "$IC_{90}$" refer to the concentration of a compound that reduces (e.g., inhibits) the activity of a target by 50% and 90%, respectively. The term "$IC_{50}$" generally describes the inhibitory concentration of the compound. Typically, measurements of $IC_{50}$ and $IC_{90}$ are made in vitro. In some embodiments, where the target is a secondary biological target, for example, a membrane-bound ion channel implicated in cardiac cytotoxicity (e.g., hERG), $IC_{50}$ is the concentration at which 50% inhibition is observed. $IC_{50}$'s and $IC_{90}$'s can be measured according to any method known to one of ordinary skill in the art.

It is known that compounds with hERG current inhibitory activity have arrhythmogenesis effect accompanied by QT interval prolongation effect. Such compounds may induce serious adverse effects such as ventricular tachycardia or sudden death. Therefore, in the development of highly safe pharmaceuticals, it is important to confirm that the test substance (target of development) does not affect hERG currents. The method of measuring hERG current inhibitory activities using the hERG-expressing human cardiomyocyte cell as provided herein facilitates the selection of compounds that do not affect hERG currents. Therefore, recombinant human cardiomyocytes and recombinant cardiomyocyte cell lines overexpressing hERG as provided herein can be used to predict the risk of a candidate drug to induce cardiac arrhythmia, and is useful in developing pharmaceuticals such as therapeutics and prophylactics for various diseases. In some embodiments, the methods as provided herein can be used by a drug designer to identify a candidate drug that poses a risk to a patient of cardiac arryhmia, which can lead to injury or death.

In some embodiments, the methods as provided herein include providing recombinant human cardiomyocytes and recombinant cardiomyocyte cell lines overexpressing hERG of the present disclosure. A compound (e.g., candidate drug) can then be contacted with the cells or cell lines. The contacting can be achieved in any convenient and feasible way. For example, a candidate drug can be suspended in a solution and the solution can be dripped onto the cells or cell lines. Alternatively, the cells can be placed in a bathing solution or medium and a candidate drug can be added to the bathing solution or the medium. Then, hERG inhibitory activity in the presence of a candidate drug is determined. This determination can be made by employing the techniques disclosed herein. For example, biological activity of potassium ion transport can be determined by patch clamp or ion flux. The hERG inhibitory activity in an absence of a candidate drug is compared to hERG inhibitory activity in the presence of the candidate drug. In some embodiments, hERG inhibitory activity in the absence of a candidate drug can be determined by employing the same techniques that were employed to determine the biological activity in the presence of the candidate drug (e.g., patch clamp or ion flux techniques). In some embodiments, this determination can be made just prior to the determination of activity in the presence of a candidate drug. In some embodiments, the activity of a channel in the absence of a candidate drug can also be determined well ahead of time or can comprise a standard reference activity, eliminating the need for performing the assay.

In some embodiments, the analysis of the comparison can provide data on the risk of a candidate drug to induce cardiac arrhythmia. For example, if hERG inhibitory activity in the presence of a candidate drug is greater than hERG inhibitory activity in an absence of the candidate drug, it is indicative of a risk of the drug to induce cardiac arrhythmia in a subject.

5.2.5.2.1 Patch Clamp Techniques

Various assays and techniques known in the art can be used for practicing the methods as provided herein. The assays described herein are meant to be representative; those of skill in the art, upon consideration of the present disclosure, will recognize additional assays and techniques that are useful in performing the present methods. In some embodiments, the assays are in vitro biological assays for testing hERG1 channel activity, for example, a FluxOR™ potassium ion channel assay, or electrophysiology measurements in single cells, as explained below.

In some embodiments, the methods as provided herein comprise monitoring ion flow through a pore using patch clamp, or voltage clamp. The clamp technique and improvements thereof, have been developed to study electrical currents in cells, and to study ion transfer through channels. To measure these currents, the membrane of a cell is closely attached to the opening of the patch micropipette so that a very tight seal is achieved. This seal prevents current from leaking outside of the patch micropipette. The resulting high electrical resistance across the seal can be exploited to perform high resolution current measurements and apply voltages across the membrane. Different configurations of the patch clamp technique can be employed. (Sakmann & Neker, (1984) *Ann. Rev. Physiol.* 46: 455).

Thus, in some embodiments, the present disclosure provides methods of measuring hERG currents using a hERG-expressing cell or hERG-expressing cell population as provided herein by the patch clamp technique. In some embodiments, provided herein are methods of measuring hERG currents using the recombinant human cardiomyocytes overexpressing hERG as provided herein by a fully automated high throughput patch clamp system.

Recombinant human cardiomyocytes overexpressing hERG can be obtained by the above-described methods. In some embodiments, the channel current as determined by patch clamping with a fully automated high throughput patch clamp system for hERG-expressing cell as provided herein is 3500 pA or more. In some embodiments, the channel current as determined by patch clamping with a fully automated high throughput patch clamp system for hERG-expressing cell as provided herein is 4000 pA or more. In some embodiments, the channel current as determined by patch clamping with a fully automated high throughput patch clamp system for hERG-expressing cell as provided herein is 4500 pA or more. In some embodiments, the channel current as determined by patch clamping with a fully automated high throughput patch clamp system for a hERG-expressing cell as provided herein is 5000 pA or more. In some embodiments, the channel current as determined by patch clamping with a fully automated high throughput patch clamp system for the hERG-expressing cell as provided herein is 6000 pA or more. Such a hERG-expressing cells or hERG-expressing cell lines is also included in the scope of the present disclosure. It should be noted here that the higher the expression level is, the higher the channel current as determined by patch clamp technique becomes.

In some embodiments for practicing methods of measuring hERG currents as provided herein, a recombinant cardiomyocytes cells overexpressing hERG as provided herein can be cultured for a specific period of time and suspended in a buffer suitable for measurement. Any buffer which does not affect hERG currents can be used, e.g., phosphate buffer or Tris-HCl buffer at pH 6-8. In some embodiments, phosphate buffered saline (pH 7.4) is used.

Subsequently, hERG currents can be recorded by a patch clamp technique, e.g., with a fully automated high throughput patch clamp system. hERG currents can be induced by giving various holding potentials and depolarizing pulses to cells. These conditions can be set by those skilled in the art (Zhou et al. (1998) *Biophysical Journal,* 74, 230-241). For example, hERG currents can be induced by changing the holding potential from −80 mV to +20 mV for 1 sec and then applying a depolarizing pulse to −50 mV for 1 sec. The peak value of the tail current can be used when the potential is restored to −50 mV. In some embodiments, the voltage command can be set as described in Example 4 or Example 5.

In some embodiments, a cell without a compound and the cell with a compound which is known to inhibit hERG currents can be prepared as controls. Specific examples of compounds that inhibit hERG currents include astemizole (Talialatel et al. (1998) *Mol. Pharmacol.* 54: 113-21), E-4031 (Zhou et al. (1998) *Biophys. J.* 74: 230-41; Kim et al. (2005) *J. Appl. Physiol.* 98(4): 1469-1477), risperidone (Kongsamut et al. (2002) *Eur. J. Pharmacol.* 450: 37-41), verapanil (Zhang et al. (1999) *Circ. Res.* 84: 989-98) and quinidine (Jiesheng et al. (2001) *J. Pharmacol. Exp. Ther.* 299: 290-6).

In some embodiments, an in vitro biological assay comprises patch clamp electrophysiology measurements, which use a high throughput single cell planar patch clamp approach (see, e.g., Schroeder et al. (2003) *J. Biomol. Screen.* 8(1): 50-64). In some embodiments, single cells are from a human adult cardiomyocyte cell line expressing hERG as provided herein. For example, human cardiomyocyte cells are dispensed into a patch plate. Amphotericin is used as a perforating agent to gain electrical access to the cells. The hERG tail current is measured prior to the addition of a compound by perforated patch clamping. Following addition of the compound, a second recording of the hERG current is performed. Post-compound hERG currents are usually expressed as a percentage of pre-compound hERG currents (% control current) and plotted against concentration for each compound. Where concentration dependent inhibition is observed, the Hill equation is used to fit a sigmoidal line to the data and an $IC_{50}$ (concentration at which 50% inhibition is observed) is determined.

5.2.5.2.2 Ion Flux Assay

A compound can be tested for its ability to modulate a potassium channel by determining the influx of ion tracers through the channel. Representative labeled potassium ions that can be employed to assay channel conductance include but are not limited to $^{41}K$. In some embodiments, aliquots of a cell suspension comprising recombinant human cardiomyocytes overexpressing hERG are incubated for 10 minutes at 37° C. in the presence of channel openers and test substances in a total volume of 100 pM (0.20-0.25 mg protein). Ion flux is initiated by the addition of HEPES/TRIS solution also containing 4 mM guanidine HCl (final) and 1000 dpm/nmol $^{14}C$ guanidine. The reaction can be continued for 30 seconds and be stopped by the addition of ice-cold incubation buffer, followed by rapid filtration under vacuum over a glass microfiber filter (grade GF/C, 1.2 µm available from Whatman, Inc. of Clifton, N.J.). The filters are washed rapidly with ice-cold incubation buffer and radioactivity is determined by scintillation counting. Non-specific uptake can be determined in parallel reactions.

In some embodiments, an ion flux assay can further comprise contacting a human cardiomyocytes cells expressing hERG with a test substance. For example, substantial ion flux can be observed in the presence of a hERG channel activator, and a reduction of flux following subsequent application of a test substance indicates an antagonist activity of the test substance. Similarly, observation of enhanced ion flux of an already-activated hERG channel following application of a test substance indicates an agonist activity of the test substance.

In some embodiments, an in vitro biological assay as provided herein is a FluxOR™ potassium ion channel assay (see, e.g., Beacham et al. (2010) *J. Biomol. Screen.* 15(4): 441-446), which allows high throughput screening of potassium ion channel and transporter activities. The FluxOR™ assay monitors the permeability of potassium channels to thallium ($Tl^+$) ions. When thallium is added to the extracellular solution with a stimulus to open channels, thallium flows down its concentration gradient into the cells, and channel or transporter activity is detected with a proprietary indicator dye that increases in cytosolic fluorescence. Accordingly, fluorescence reported in the FluxOR™ system is an indicator of any ion channel activity or transport process that allows thallium into cells.

5.2.5.2.3 Membrane Potential Assay Kit

In some embodiments, methods as provided herein comprise measuring changes in membrane potential on the hERG-expressing human cardiomyocyte cell using FLIPR Membrane Potential Assay Kit (Molecular Devices). For example, changes in membrane potential can be measured by performing the following operations. hERG-expressing cells or cell lines can be prepared according to methods as provided herein in order to prepare a cell suspension of a concentration of $0.2 \times 10^5$ cells/ml to $1.0 \times 10^6$ cells/ml. Subsequently, the cell suspension is plated on plates (such as Biocoat Poly-D-Lysine 384-Well Black/Clear Plate; BECKTON DICKINSON) and cultured further. Subsequently, Component A contained in FLIPR Membrane Potential Assay Kit (Molecular Devices) is dissolved in a measurement buffer (130 mM NaCl, 5 mM KCl, 1 mM $MgCl_2$, 1 mM $CaCl_2$, 24 mM Glucose, 10 mM HEPES (final pH: approx. 7.25)), and a 25 µl aliquot of this solution is added to each well. About one hour after the addition of Component A, changes in membrane potential can be measured with FLIPR (Molecular Devices) or FDSS6000 (Hamamatsu Photonics).

5.2.5.3. Methods of Identifying Candidate Compounds for Reduction in Cell Viability Cardiomyocytes and cardiomyocyte cell lines as provided herein can be used in drug screening and development, including for drug-associated cardiotoxicity that is related to reduction in cell viability. For any and all of the following methods, the compounds can include novel or previously known drugs.

Assays for cell viability include assays that measure metabolic capacity, proliferation, apoptosis, mitochondrial damage, and/or plasma membrane damage using a variety of assays known in the art (e.g., an ATP/ADP assay; a Calcein AM assay; a clonogenic assay; an ethidium homodimer assay; a cytochrome oxidase activity assay; an adenylate kinase (AK) assay; an Alamar Dye/Setublue assay; a lactate dehydrogenase (LDH) assay; formazan-based assays (MTT/XTT); reduction of MTS tetrazolium; dyes such as, e.g., Evans blue, neutral red, methyl violet, propidium iodide, sulforhodamine B, fluorescein diacetate hydrolysis/Propidium iodide staining (FDA/PI staining), carboxyfluorosuccinimide ester (CFSE) dye, Resazurin, Trypan Blue, and a living-cell exclusion dye (dye only crosses cell membranes of dead cells)); detection of mutations in mtDNA; release of components across the mitochondrial permeability transition pore; changes in mitochondrial membrane potential; flow cytometry; green fluorescent protein; a DNA stain that can differentiate necrotic, apoptotic and normal cells; measurement of cytochrome c release; caspase proteolytic cleavage of poly(ADP-ribose) polymerase (PARP); detection of Annexin V; senescence-associated expression of β-galactosidase (SA-β-Gal) activity; a TUNEL assay; and the like). Also see, e.g., "Mammalian Cell Viability—Methods and Protocols,", *Methods in Molecular Biology*, April 2011, edited by Stoddart, Martin J. In such assays, a candidate drug can be contacted with the cells or cell lines. The contacting can be achieved in any convenient and feasible way. For example, a candidate drug can be suspended in a solution and the solution can be dripped onto the cells or cell lines. Alternatively, the cells can be placed in a bathing solution or medium and a candidate drug can be added to the bathing solution or the medium. Viability of the cell(s) in the presence of a candidate drug is determined. In some embodiments, viability is determined by employing a cell proliferation assay, for example, a colorimetric or a fluorescence cell proliferation assay as described herein.

In some embodiments, the analysis of the comparison can provide data on the risk of cardiotoxicity of a candidate drug. For example, if the viability of the cell(s) in the presence of a candidate drug is less than the viability of the cell(s) in an absence of the candidate drug, it is indicative of a risk of the drug to be cardiotoxic in a subject.

5.2.5.3.1 Fluorescence Cell Viability Assay

A compound can be tested for its ability to reduce cell viability, as measured in a fluorometric proliferation assay (e.g., SetuBlue™ Cell Proliferation Assay Kit (Fluorometric)) employing the techniques disclosed herein. The viability of the cell(s) in an absence of a compound is compared to the viability of the cell(s) in the presence of the compound.

5.2.5.3.2 Luminescence Cell Viability Assay

A compound can be tested for its ability to reduce cell viability, as measured in a luminescence assay (e.g., Cell-Titer-Glo®, RealTime-Glo™, CellTox™ Green, TACS® MTT Cell Proliferation Assay, TACS® XTT Cell Proliferation Assay). The viability of the cell(s) in an absence of a compound is compared to the viability of the cell(s) in the presence of the compound.

5.2.5.4. Methods of Predicting Risks of Candidate Compounds to Cause Cardiotoxicity It is further known that compounds with hERG current inhibitor activity as well as compounds with weak or absent hERG current inhibitory activity may be cardiotoxic. Therefore, in the development of highly safe pharmaceuticals, it is important to evaluate the test substance (target of development) for cardiotoxicity in assays to determine hERG current inhibitory activity and/or in assays to determine cell viability inhibitory activity. Cardiomyocytes and cardiomyocyte cell lines, as provided herein, are useful in both assays of hERG current inhibitory activity and cell viability inhibitory activity. In some embodiments, cardiotoxicity of candidate compounds is not caused by inhibition of (e.g., by blocking or obstructing, either fully or partially) hERG. Methods that allow evaluation of cell viability, when combined with methods that allow determination of inhibition of the hERG channel, can identify compounds that are: (i) hERG inhibitors, but not inhibitors of cell viability; (ii) hERG inhibitors and inhibitors of cell viability; (iii) inhibitors of cell viability, but not inhibitors of hERG; and (iv) not inhibitors of hERG and not inhibitors of cell viability. Cardiomyocytes and cardiomyocyte cell lines, as provided herein, are also useful in understanding mechanisms of toxicity of compounds as revealed by ultrastructural changes in the cells and cell lines treated with the compounds, for example, changes in cytoskeleton, nucleus, mitochondria, golgi, and/or other sub-cellular compartments.

The methods of determining cardiotoxicity using the hERG-expressing human cardiomyocyte cardiomyocytes and cardiomyocyte cell lines as provided herein facilitate the selection of compounds that are not cardiotoxic. Therefore, cells or cell lines as provided herein can be used to predict the risk of cardiotoxicity of a candidate drug, and are useful in developing pharmaceuticals such as therapeutics and prophylactics for various diseases. In some embodiments, the methods as provided herein can be used by a drug designer or developer to identify a candidate drug that poses a risk to a patient of cardiotoxicity, which can lead to injury or death.

5.2.5.5. Compounds

Examples of compounds include peptides, proteins, non-peptidic compounds, synthetic compounds, fermentation products, cell extracts, plant extracts and animal tissue extract. The compounds can be either novel compounds or known compounds.

In some embodiments, the compound is selected from a list of compounds that have failed in clinical trials, or were halted in clinical trials due to cardiotoxicity.

In some embodiments, the compound is selected from TABLE A, below:

TABLE A

| Cardiac Hazardous Drugs | |
|---|---|
| Category of Drug | Drug |
| Calcium channel blockers | Prenylamine (TdP reported; withdrawn) |
| | Bepridil (TdP reported; withdrawn) |
| | Terodiline (TdP reported; withdrawn) |
| Psychiatric drugs | Thioridazine (TdP reported) |
| | Chlorpromazine (TdP reported) |
| | Haloperidol (TdP reported) |
| | Droperidol (TdP reported) |
| | Amitriptyline |
| | Nortriptyline |
| | Imipramine (TdP reported) |
| | Desipramine (TdP reported) |
| | Clomapramine |
| | Maprotiline (TdP reported) |
| | Doxepin (TdP reported) |

TABLE A-continued

| Cardiac Hazardous Drugs | |
|---|---|
| Category of Drug | Drug |
| | Lithium (TdP reported) |
| | Chloral hydrate |
| | Sertindole (TdP reported; withdrawn in the UK) |
| | Pimozide (TdP reported) |
| | Ziprasidone |
| Antihistamines | Terfenadine (TdP reported; withdrawn in the USA) |
| | Astemizole (TdP reported) |
| | Diphenhydramine (TdP reported) |
| | Hydroxyzine |
| | Ebastine |
| | Loratadine |
| | Mizolastine |
| Antimicrobial and antimalarial drugs | Erythromycin (TdP reported) |
| | Clarithromycin (TdP reported) |
| | Ketoconazole |
| | Pentamidine (TdP reported) |
| | Quinine |
| | Chloroquine (TdP reported) |
| | Halofantrine (TdP reported) |
| | Amantadine (TdP reported) |
| | Sparfloxacin |
| | Grepafloxacin (TdP reported; withdrawn) |
| | Pentavalent antimonial meglumine |
| Serotonin agonists/antagonists | Ketanserin (TdP reported) |
| | Cisapride (TdP reported; withdrawn) |
| Immunosuppressant | Tacrolimus (TdP reported) |
| Anticancer agents | Doxorubicin |
| | Epirubicin |
| | Idarubicin |
| | Daunorubicin |
| Antidiuretic hormone | Vasopressin (TdP reported) |
| Other agents | Adenosine |
| | Organophosphates |
| | Probucol (TdP reported) |
| | Papaverine (TdP reported) |
| | Cocaine |

In some embodiments, the compound is an anticancer agent, such as anthracyclines, mitoxantrone, cyclophosphamide, fluorouracil, capecitabine and trastuzumab. In some embodiments, the compound is an anthracycline. In some embodiments, the compound is doxorubicin.

In some embodiments, the compound is an immunomodulating drug, such as interferon-alpha-2, interleukin-2, infliximab and etanercept. In some embodiments, the compound is an antidiabetic drug, such as rosiglitazone, pioglitazone and troglitazone. In some embodiments, the compound is an antimigraine drug, such as ergotamine and methysergide. In some embodiments, the compound is an appetite suppressant, such as fenfluramine, dexfenfluramine and phentermine. In some embodiments, the compound is a tricyclic antidepressants. In some embodiments, the compound is an antipsychotic drug, such as clozapine. In some embodiments, the compound is an antiparkinsonian drug, such as pergolide and cabergoline. In some embodiments, the compound is an glucocorticoid. In some embodiments, the compound is an antifungal drugs such as itraconazole and amphotericin B. In some embodiments, the compound is an NSAID, including selective cyclo-oxygenase (COX)-2 inhibitors.

In some embodiments, the compound is selected from the group consisting of an antihistamine, an antiarrhythmic, an antianginal, an antipsychotic, an anticholinergic, an antitussive, an antibiotic, an antispasmodic, a calcium antagonist, an inotrope, an ACE inhibitor, an antihypertensive, a beta-blocker, an antiepileptic, a gastroprokinetic agent, an alphal-blocker, an antidepressant, an aldosterone antagonist, an opiate, an anesthetic, an antiviral, a PDE inhibitor, an antifungal, a serotonin antagonist, an antiestrogen, and a diuretic.

In some embodiments, the compound is an active ingredient in a natural product. In some embodiments, the compound is a toxin or environmental pollutant.

In some embodiments, the compound is an antiviral agent.

In some embodiments, the compound is selected from the group consisting of a protease inhibitor, an integrase inhibitor, a chemokine inhibitor, a nucleoside or nucleotide reverse transcriptase inhibitor, a non-nucleoside reverse transcriptase inhibitor, and an entry inhibitor.

In some embodiments, the compound is capable of inhibiting hepatitis C virus (HCV) infection.

In some embodiments, the compound is an inhibitor of HCV NS3/4A serine protease.

In some embodiments, the compound is an inhibitor of HCV NS5B RNA dependent RNA polymerase.

In some embodiments, the compound is an inhibitor of HCV NS5A monomer protein.

In some embodiments, the compounds is selected from the group consisting of Abacavir, Aciclovir, Acyclovir, Adefovir, Amantadine, Amprenavir, Ampligen, Arbidol, Atazanavir, Balavir, Boceprevirertet, Cidofovir, Darunavir, Delavirdine, Didanosine. Docosanol, Edoxudine, Efavirenz, Emtricitabine, Enfuvirtide, Entecavir, Famciclovir, Fomivirsen, Fosamprenavir, Foscarnet, Fosfonet, Ganciclovir, Ibacitabine, Imunovir, Idoxuridine, Imiquimod, Indinavir, Inosine, Interferon type III, Interferon type II, Interferon type I, Interferon, Lamivudine, Lopinavir, Loviride, Maraviroc, Moroxydine, Methisazone, Nelfinavir, Nevirapine, Nexavir, Oseltamivir (Tamiflu), Peginterferon alfa-2a, Penciclovir, Peramivir, Pleconaril, Podophyllotoxin, Raltegravir, Ribavirin, Rimantadine, Ritonavir, Pyramidine, Saquinavir, Sofosbuvir, Stavudine, Telaprevir, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), and Zidovudine.

In some embodiments, the compound is selected from the group consisting of terfenadine, astemizole, grepafloxacin, terodiline, droperidol, lidoflazine, sertindole, levomethadyl and cisapride.

In some embodiments, the compound is selected from the group consisting of ivabradine, dofetilide, ibutilide, E-4031, MK-499, KN-93, amiodarone, cisapride, haloperidol, droperidol, bepridil, terfenadine, propafenone, domperidone, changrolin, and bertosamil. In some embodiments, the compound is selected from the group consisting of amiodarone, cisapride, droperidol and haloperidol. In some embodiments, the compound is selected from the group consisting of bepridil, domperidone, E-4031 and terfenadine.

In some embodiments, the compound is ivabradine, for which the chemical name is "3-[3-({[(7S)-3,4-dimethoxybicyclo[4.2.0]octa-1,3,5-trien-7-yl]methyl}(methyl)amino) propyl]-7,8-dimethoxy-2,3,4,5-tetrahydro-1H-3-benzazepin-2-one." The structure of ivabradine is provided below:

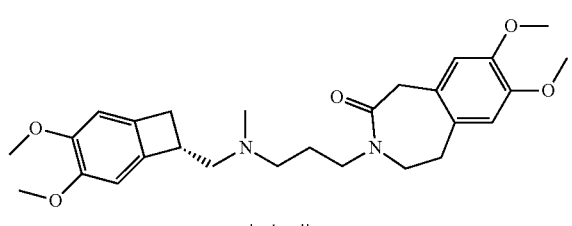

ivabradine

In some embodiments, the compound is a methanesulfonanilide, for example, dofetilide or ibutilide.

In some embodiments, the compound is dofetilide, for which the chemical name is "N-[4-(2-{[2-(4-methane sulfonamidophenoxy)ethyl](methyl)amino}ethyl)phenyl]methanesulfonamide." The structure of dofetilide is provided below:

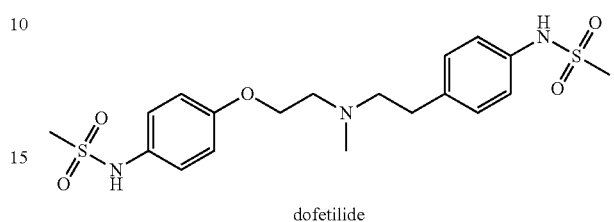

dofetilide

In some embodiments, the compound is cisapride, for which the chemical name is "(±)-cis-4-amino-5-chloro-N-(1-[3-(4-fluorophenoxy)propyl]-3-methoxypiperidin-4-yl)-2-methoxybenzamide." The structure of cisapride is provided below:

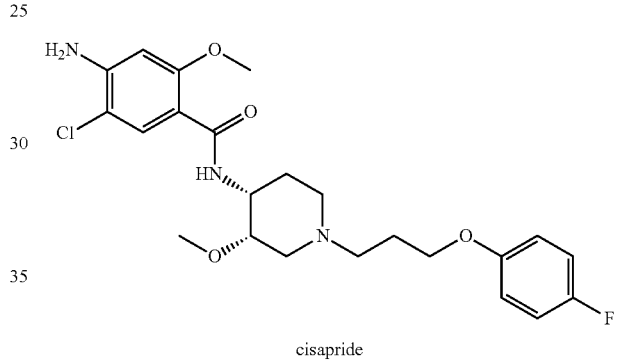

cisapride

In some embodiments, the compound is Daclatasvir (BMS-790052), for which the chemical name is "Methyl [(2S)-1{(2S)-2-[5-(4'-{2-[(2S)-1{(2S)-2-[(methoxycarbonyl)amino]-3-methylbutanoyl}2-pyrrolidinyl]-1H-imidazol-5-yl}4-biphenylyl)-1H-imidazol-2-yl]-1-pyrrolidinyl}3-methyl-1-oxo-2-butanyl]carbamate." The structure of Daclastavir is provided below:

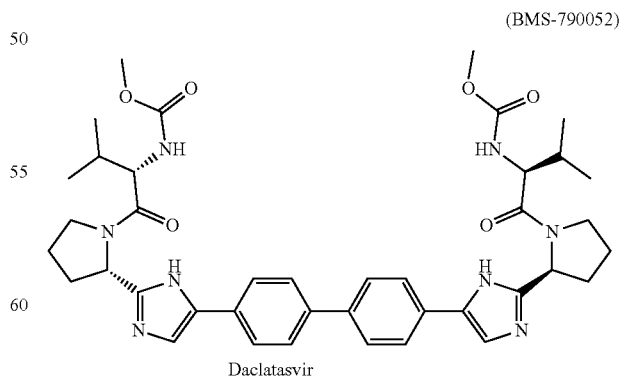

Daclatasvir

In some embodiments, the compound is BMS-986094, for which the chemical name is "(2R)-neopentyl 2-(((((2R,3R,4R)-5-(2-amino-6-methoxy-9H-purin-9-yl)-3,4-dihydroxy- 4-methyltetrahydrofuran-2-yl)methoxy)(naphthalen-1-yloxy)phosphoryl)amino)propanoate." The structure of BMS-986094 is illustrated below:

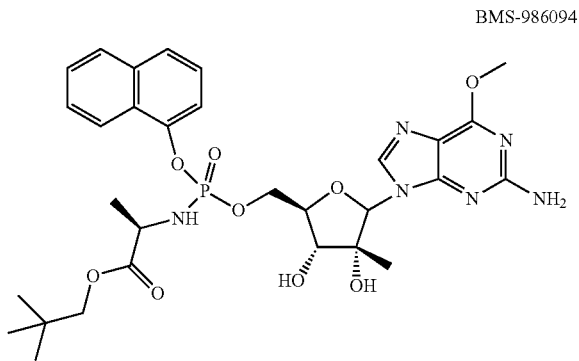 [SMILES: COc1nc(N)nc2c1ncn2C1O[C@H](COP(=O)(N[C@H](C)C(=O)OCC(C)(C)C)Oc2cccc3ccccc23)[C@@H](O)[C@@]1(C)O]

BMS-986094

In some embodiments, the compounds are: (i) hERG inhibitors, but not inhibitors of cell viability; (ii) hERG inhibitors and inhibitors of cell viability; (iii) inhibitors of cell viability, but not inhibitors of hERG; and (iv) not inhibitors of hERG and not inhibitors of cell viability.

The following examples are included to demonstrate preferred embodiments of the disclosure. It should be appreciated by those of ordinary skill in the art that the techniques disclosed in the examples which follow represent techniques discovered by the inventor to function well in the practice of the disclosure, and thus can be considered to constitute preferred modes for its practice. However, those of ordinary skill in the art should, in light of the present disclosure, appreciate that many changes can be made in the specific embodiments which are disclosed and still obtain a like or similar result without departing from the spirit and scope of the disclosure.

6. EXAMPLES

6.1 Example 1: Transfection of HEK-293T Cells to Generate Pseudo-Lenti Viral Particles A hERG expression clone containing a human KCNH2 gene sequence with C-Flag tag (Uniprot Accession # Q12809; GeneCopoeia™ vector EX-A1128-Lv203, see FIG. 4A), CMV promoter, eGFP and puromycin stable selection marker was transformed into stb13 chemically competent *E. coli*. The Promega PureYield™ Plasmid Maxiprep kit (Catalog # A2392) was used to purify the plasmid from transformed bacteria lysates. The purified plasmids were characterized by restriction digestion, UV absorption spectrum and DNA sequencing.

Pseudovirus particles were generated in HEK-293T cells by transfecting using the Lenti-Pac™ HIV Expression Packaging Kit (GeneCopoeia Catalog # HPK-LvTR-20). Briefly, HEK-293T cells (ATCC Cat. No. CRL-11268) were seeded one or two days before the transfection in a 6 well plate or a 10 cm dish in complete growth media (DMEM) supplemented with 10% heat inactivated fetal bovine serum (FBS), so that the cells were 65-80% confluent at the time of transfection. The cells were incubated in humidified incubator at 37° C. with 5% $CO_2$.

Transfections were carried out according to manufacturer's protocols (Genecopoeia/Promega/lnvitrogen). More specifically, 2-3 µg of lentiviral ORF expression plasmid DNA and 4-6 µl of Lenti-Pac™ HIV mix were first mixed in 200 µl Opti-MEM I in a tube. In a separate tube, 12-18 µl of EndoFectin Lenti was diluted with 200 µl Opti-MEM I media. The diluted EndoFectin Lenti reagents were added drop wise to the DNA-containing tube. The mixture was incubated at room temperature for 10-30 minutes to allow the DNA-EndoFectin complex to form. The complex mixture was then added directly to each well and the plate was gently swirled. After incubation at 37° C. and 5% $CO_2$ for 12-16 h, the medium containing the mixtures was gently removed, and fresh growth medium was added. At 36, 48 and 72 hours post transfection, psedudovirus-containing culture medium was collected in sterile capped tubes, and the tubes were centrifuged. The supernatant was filtered through 0.45 µM low protein-binding filters.

The viral titer was estimated by qRT-PCR using Lenti-Pac HIV qRT-PCR Titration Kit (GeneCopoeia, Catalog # HPR-LTK-050). Transduction efficiency was monitored in HEK-293T cells by analyzing eGFP expression using flow cytometry (FACS Calibur BD Bioscience).

6.2 Example 2: Generation of Recombinant Cardiomyocytes and Cardiomyocyte Cell Lines Expressing Herg Cells expressing hERG were prepared by transducing cells from AC10 adult human ventricular cardiomyocytes (ATCC Cat. No. PTA-1501) with the pseudovirus particles generated in Example 1 containing an expression vector that expresses a C-terminal FLAG-tagged hERG. This expression vector also contains a bicistronic eGFP reporter gene and confers puromycin resistance for positive selection and maintenance.

More specifically, adult human ventricular cardiomyocytes (AC10 cells, ATCC catalog # PTA-1501) are referred to herein as hMYO cells and were seeded in a 24-well plate two days before viral infection. The cells reached to 65-80% confluency at the time of transduction. The cells were cultured in DMEM/F-12 (Gibco, Catalog # 11330-032) supplemented with 10-12.5% heat inactivated FBS and 100 units/ml penicillin/streptomycin, and were maintained throughout this study at 37° C. and 5% $CO_2$ in a humidified chamber. Such hMYO cells are useful as control cells.

The cells were infected with diluted pseudovirus particles in presence of low serum growth medium and 5-8 µg/ml of Polybrene (Sigma-Aldrich Catalog # H9268). At 12 hours post infection, cultures were washed with PBS (HyClone catalog # SH30256.01). The cells were then cultured in fresh low serum growth medium (DMEM/F12). 2 days post-transduction, the cells were passaged, split (1:5) by trypsinized, reseeded onto 6-well plate, and incubated for 48 hours in complete growth medium. The transient expression of transgenes in the infected target cells was analyzed by flow cytometry or with a fluorescent microscope. The media was replaced every 3-4 days with fresh low serum growth medium containing 20-50 µg/ml of selection drug (Puromycin) until drug resistance colonies become visible to select stably transduced cells. The drug resistance colonies and cells derived therefrom are designated as hMYO-hERG.

HEK293 cells expressing hERG were prepared also by transduction. More specifically, HEK-hERG cells were prepared by transducing HEK293 cells (human embryonic kidney derived cells) with the pseudovirus particles generated in Example 1 containing an expression vector that expresses a C-terminal FLAG-tagged hERG channel). This expression vector also contains a bicistronic eGFP reporter gene and confers puromycin resistance for positive selection and maintenance.

HeLa cells expressing hERG were also prepared by transduction. More specifically, HeLa cells were prepared by transducing HeLa cells with the pseudovirus particles generated in Example 1 containing an expression vector that expresses a C-terminal FLAG-tagged hERG channel). This expression vector also contains a bicistronic eGFP reporter gene and confers puromycin resistance for positive selection and maintenance.

The expression of hERG in the generated hMYO-hERG and HEK-hERG were analyzed and compared with control and other cell lines. The results are shown in FIGS. 4B-4C. As shown, the level of the hERG expression in the hMYO-hERG cells is substantially higher than control cells and other hERG expressing cells (e.g., HEK-hERG and Hela-hERG cells). The hMYO-hERG cells are designated as hERG-overexpressing cardiomyocytes.

6.3 Example 3: Cell Culture for Patch Clamp

Cell Culture, Cell Harvesting Reagents, and Electrophysiology Buffers for Automated Patch Clamp Ionflux 16

Cell culture medium contains 89% DMEM/F12 (Life Technologies, 11330-057), 10% FBS (Life Technologies, 26140-079), 1% Penicillin/Streptomycin (Life Technologies, 15140-122), and 10 µg/mL puromycin (Life Technologies, A11138-03). 10 µg/ml puromycin is added freshly to the media after overnight incubation of the newly sub-cultured cells.

Serum free medium contains 100% DMEM/F12 (Life Technologies, 11330-057).

Harvesting agent contains 0.05% Trypsin-EDTA solution (Life Technologies, 25300-054).

Extracellular Ringer's Solution (ECS or EC buffer) contains Dulbecco's phosphate-buffered saline (DPBS) (with calcium and magnesium) (Corning, 21-030-CV), and 10 mM HEPES. The solution is adjusted to pH 7.4 with NaOH, and osmolarity is adjusted to be 300 mOsm with sucrose.

Intracellular Solution (ICS) contains 90 mM KF, 30 mM KCl, 11 mM EGTA, 10 mM HEPES, and 2 mM $MgCl_2$. The solution is adjusted to pH 7.2 with KOH, and osmolarity is adjusted to be about 285 mOsm with KCl.

Culturing of Cells from Frozen Vials

One cryopreserved vial of cells ($1\times10^6$ cells/ml) was quickly thawed in 37° C. water bath for 2 to 3 minutes. The cells were added to 7 ml pre-warmed growth cell culture medium, and pelleted by centrifugation at 300×g for 5 minutes at room temperature. Aseptically aspirate the supernatant without disturbing the cell pellet and gently re-suspend the cells in 15 ml of complete growth medium and then transfer to a new T75 flask to culture at high density to optimize recovery. The cells were grown in a 37° C. incubator with 5% $CO_2$ and 95% humidity, and sub-cultured after two days.

Sub-Culturing

The cells in a T75 flask were washed twice with PBS, and then treated with 2 ml 0.05% trypsin at 37° C. for 3 minutes to be detached from the flask. Trypsin was neutralized by adding 5 ml complete cell culture medium, and the cells were gently re-suspended by pipetting up and down 5 times. 2 ml of the resuspension was transferred into a new T75 flask containing 13 ml cell culture medium. The cells were grown in a 37° C. incubator with 5% $CO_2$ and 95% humidity. Following overnight incubation, 10 µg/ml puromycin was added to the flask to maintain the selection. The cells were sub-cultured again when 70-80% confluency was reached (after 2 to 3 days).

Cell Preparation for Automated Patch Clamp Experiments

When the cells reached 80% confluency in a T175 flask, they were shifted from 37° C. to 28° C. (maintaining 5% $CO_2$ and 90% humidity) and incubated for 48 hours. Following this incubation, the cells were washed twice with PBS and treated with 3 ml 0.05% trypsin at 37° C. for 3 minutes. Most cells were floating with minimal amount of clumps under microscope. Trypsin was neutralized by adding 7 ml fresh cell culture media, and the cells were re-suspended by pipetting up and down 5-7 times. The cells were pelleted at 300×g for 5 minutes at room temperature, then re-suspended in 6 ml serum free media, and incubated at 37° C. for 30 minutes. Following the incubation, the cells were pelleted at 300×g, washed once with ECS, and re-suspended in ECS to a final concentration of $3-5\times10^6$ cells/ml. Following resuspension, an amount (250pl) of the cell mixture was added to a designated well of an IonFlux 16 plate to perform the experiment.

6.4 Example 4: Comparison OF hMYO Cells and hMYO-hERG Cells

In this exemplary study, hMYO-hERG cells stably expressing hERG described herein were compared with hMYO cells.

Cells were prepared as described below. The cells were grown to 70% to 90% confluency in a flask (at 37° C. and 5% $CO_2$) and removed from the incubator 1 to 3 days after plating. The cells were then incubated at 30° C. and 5% $CO_2$ for 24-48 hours. After that, growth medium was aspirated from the culture flasks and the cells were gently rinsed with water or PBS to remove residual medium and dead cells. The cells were then rinsed with a total of 3-5 ml of 0.05% trypsin-EDTA solution and the flasks containing cells were incubated at 37° C. for 3-4 minutes. A total of 10 ml of complete media was added to the flask, and the cells were gently dislodged from the flask. The mixture was centrifuged at 300×g for 5 min at room temperature. The cell supernatant was decanted, and the cell pellet was resuspended in 5 ml of serum free medium or serum free CHO-SFM II medium, and incubated for 20-30 minutes at 28° C. and 5% $CO_2$. The cell suspension was then centrifuged at 300×g for 4 min and resuspended in ECS, followed by triturations using a 1000 µl pipettor. The cells were then pelleted with centrifugation and the buffer was carefully aspirated. Cells were resuspended in fresh ECS buffer and incubated for 5-10 minutes at room temperature, but for no more than 20 minutes. 250 µl of the cell suspension was then added to the 'IN' well of Ionflux16 plate (see FIG. 7A) just prior to the experimental run. The cell suspension had a final concentration of about 3 to 5 million cells per milliliter, and this corresponds to about 750,000 to 1,250,000 cells per well.

Figure 5A:
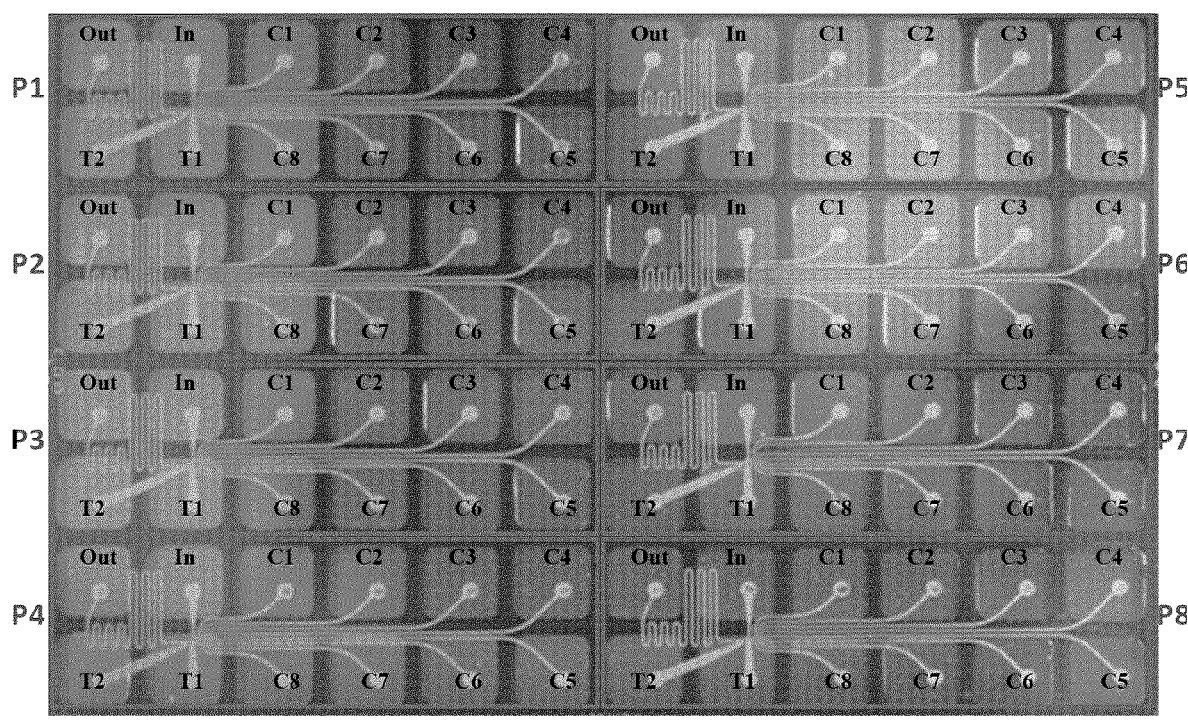
FIG. 5A shows an exemplary Ionflux 16 plate that contains 8 experimental regions (P1 to P8).
Figure 5B:
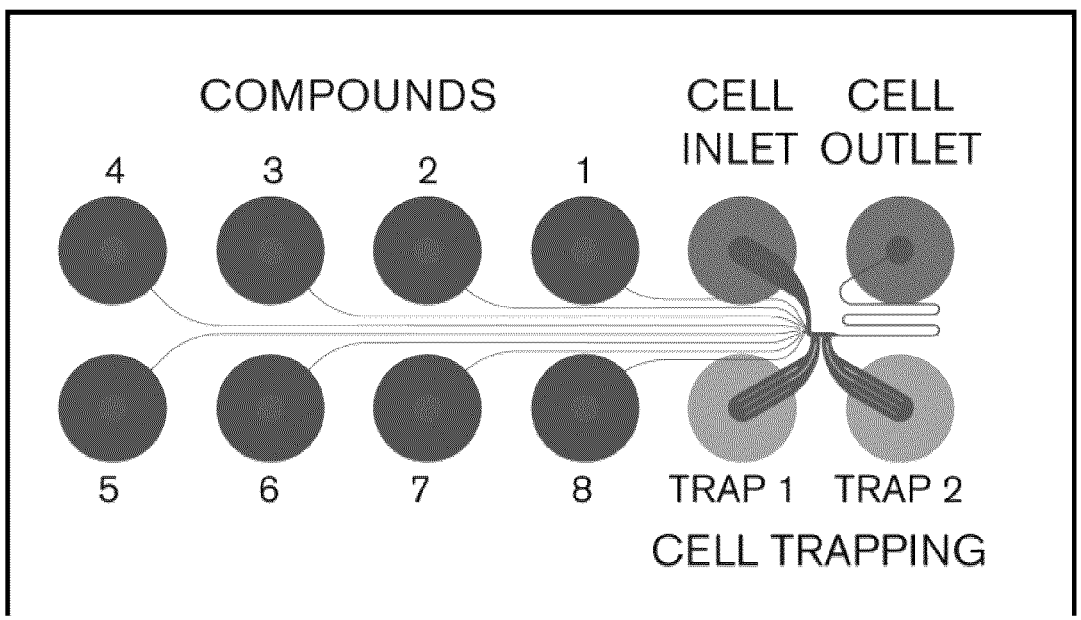
FIG. 5B illustrates each region containing 12 wells.

As shown in FIG. 5A, the Ionflux 16 plate used in this study contains 8 experimental regions (P1 to P8), and each region contains 12 wells (see FIG. 5B). 2 wells are for trapping the cells ('T1' and 'T2'); 8 wells are for compounds (C1-C8), and 2 wells are for cell inlet "In" and outlet "Out." Cells are loaded in the inlet well, ICS is loaded into the trapping wells, and 8 compounds (and/or solutions) are loaded into the remaining 8 wells. The wells are interconnected through microfluidic channels running within the well plate. Cells are pushed through the main flow channel and pulled onto an ensemble of 20 small pipette-like channels by vacuum. There are two such ensembles in each experimental pattern (or region)—T1 and T2, which are exposed to the same group of 8 compounds (and/or solutions). A discrete patch clamp amplifier is used for continuous recording for each ensemble, and a patch clamp amplifier records a sum of currents across all 20 trapped cells resulting in consistent data.

Immediately before the experiments, the cells were washed once in EC buffer. The cells were then resuspended in EC buffer with a concentration of $3\text{-}5\times10^6$ cells/ml. Plates were primed for 3 min according to the following protocol: (1) traps and compounds at 8 psi for t=0-160 s and 1.6 psi for t=160-175 s, (2) traps but not compounds at 1.6 psi for t=175-180 s, and (3) main channel at 1 psi for t=0-160 s and 0.2 psi for 160-180s.

After cell introduction in to the proper inlet wells, the plates were re-primed as follows: (1) traps and compounds at 5 psi for t=0-15 s and 2 psi for t=15-55 s, (2) traps but not compounds at 2 psi for t=55-60 s, and (3) main channel at 1 psi for t=0-20 s, 0.5 psi for t=20-40 s, and 0.2 psi for t=40-60 s.

Then, cells were introduced into the main channel and trapped at lateral trapping sites with a trapping protocol: (1) trapping vacuum of 6 mm Hg for t=0-30 s and 4 mm Hg for t=30-85 s, (2) main channel pressure of 0.1 psi for t=0-2 s, followed by 15 repeated square pulses of 0-0.2 psi with baseline duration of 4.5 s and pulse duration of 0.5 s, followed by 0.1 psi for 8 s.

One to five break protocols were performed and currents were stabilized before compound testing. A negative control (EC buffer with 0.01% DMSO) was tested before compound testing.

Figure 6:
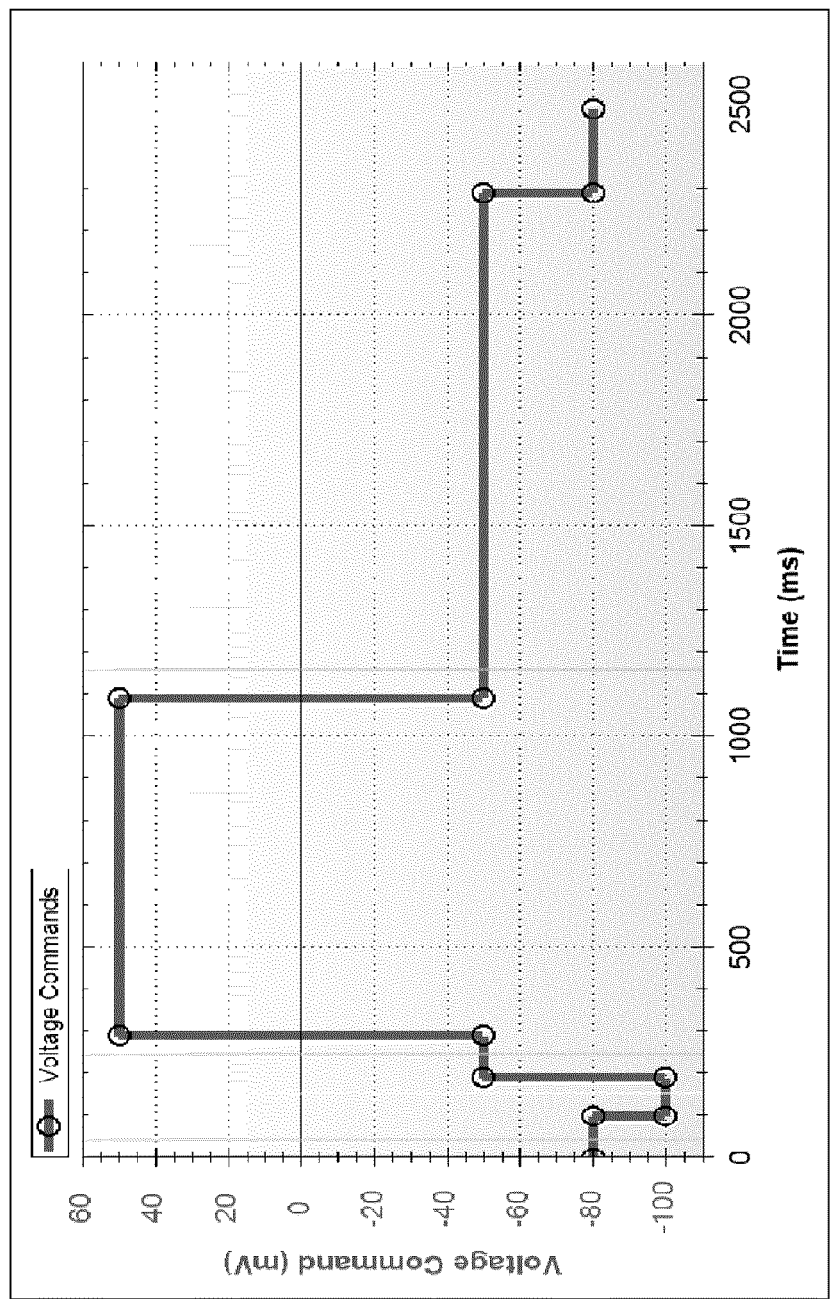
FIG. 6 shows an exemplary voltage command protocol used for hERG current on IonFlux16 automated patch clamp.

Voltage command protocol(s) used in the study for hERG current was similar to those employed in conventional patch clamping: Vh was −80 mV and an initial step to +50 mV for 800 ms inactivated the channels, followed by a 1 s step to −50 mV to elicit the outward tail current that was measured (see FIG. 6).

The current of hMYO-hERG cells of passage No. 14 was compared with the current of hMYO (control without hERG) at 37° C. in the Ionflux 16 plate described above. The hMYO cells were loaded on regions P1 and P2, and the hMYO-hERG cells were loaded on regions P3 and P4. For each region, T1 and T2 cell trap zones were filled with ICS, and a single concentration of ECS buffer was applied five to eight times (C1-C8) to study the stability of whole-cell recordings. The different current amplitude plateaus correspond to the ECS buffer applied at different times. The voltage patch clamp protocol shown in FIG. 6 was performed and the current was measured.

The current obtained was leak-subtracted and represented in FIGS. 7A-7C. The current amplitudes at times C1-C5 for both cell lines are summarized in Table 1 below, and rundown effect is analyzed by normalizing the current amplitudes at times C2-C5 to that at C1.

TABLE 1

Current amplitudes at times C1-C5 for hMYO-hERG cells of passage No. 14

| Compd | Time(s) | PO3_T1 (pA) | Norm to C1 (%) | PO3_T2 (pA) | Norm to C1 (%) | PO4_T1 (pA) | Norm to C1 (%) | PO4_T2 (pA) | Norm to C1 (%) |
|---|---|---|---|---|---|---|---|---|---|
| C1 | 0 | 4263 | 100 | 6005 | 100 | 3032 | 100 | 4550 | 100 |
| C2 | 120 | 4533 | 106 | 6315 | 105 | 3544 | 117 | 4384 | 96 |
| C3 | 300 | 3776 | 89 | 5656 | 94 | 3650 | 120 | 4190 | 92 |
| C4 | 480 | 4244 | 100 | 5652 | 94 | 3662 | 121 | 3720 | 82 |
| C5 | 660 | 4025 | 94 | 5490 | 91 | 3468 | 114 | 3557 | 78 |

As shown in FIGS. 7A-7C, the hMYO cells exhibited currents near zero (about −500 to −200 pA, see FIG. 7B); while the hMYO-hERG cells expressing hERG exhibited substantial stable current sweeps of about 3500-6000 pA (see FIG. 7C). The magnitude of the current achieved in the hMYO-hERG cells is above 6000 pA and on an average of about 4000 pA, and the current remains stable over a longer time period.

Table 1 also shows the stability of the current of the present hMYO-hERG cells with no or minor rundown effect (fainting of current over time). Table 1 shows the current amplitudes for each trap over time (C1-C5). Three trap zones (P3T2, P4T1, and P4T2) show no rundown effect over the time course, and there is about 22% decrease in the magnitude of the current in one of the trap zones (P3T1) (about 15-20% is generally acceptable).

Rundown effect makes it difficult to calculate the true percentage of inhibition by a compound since the decrease in current can be due to both the compound treatment and the rundown effect. Thus, the hMYO-hERG cells stably expressing hERG as provided herein have an advantage over other currently available cell lines since the hMYO-hERG cells do not require the presence of ATP to give consistent high signals without rundown effect.

The experiments were repeated using hMYO-hERG cells of passage No. 17 and passage No. 25. The results for the hMYO-hERG cells of passage No. 17 are shown in FIG. 8 and Table 2. The results for the hMYO-hERG cells of passage No. 25 are shown in FIG. 9 and Table 3.

TABLE 2

Current amplitudes at times C1-C5 for hMYO-hERG cells of passage No. 17

| Compd | Time(s) | PO5_T1 (pA) | Norm to C1 (%) | PO5_T2 (pA) | Norm to C1 (%) |
|---|---|---|---|---|---|
| C1 | 0 | 3435 | 100 | 4342 | 100 |
| C2 | 120 | 3383 | 98 | 4820 | 111 |
| C3 | 300 | 3990 | 116 | 5154 | 119 |
| C4 | 480 | 3693 | 108 | 5132 | 118 |
| C5 | 660 | 2790 | 81 | 4816 | 111 |

TABLE 3

Current amplitudes at times C1-C5 for hMYO-hERG cells of passage No. 25

| Compd | Time(s) | PO4_T1 (pA) | Norm to C1 (%) | PO4_T2 (pA) | Norm to C1 (%) |
|---|---|---|---|---|---|
| C1 | 0 | −73 | 100 | 2983 | 100 |
| C2 | 120 | −133 | 182 | 2954 | 99 |
| C3 | 285 | −70 | 96 | 2963 | 99 |
| C4 | 450 | −283 | 388 | 3068 | 103 |
| C5 | 615 | −170 | 233 | 2563 | 86 |
| C6 | 780 | 197 | −270 | 2606 | 87 |
| C7 | 945 | 13 | −18 | 2425 | 81 |
| C8 | 1110 | −107 | 147 | 2474 | 83 |

As shown, the magnitude of the current achieved for hMYO-hERG cells of passage No. 17 was between about 3500 to about 5000 pA, and remained stable over the course of the experiment with no or minor rundown effect (see FIG. 8 and Table 2).

When hMYO-hERG cells of passage No. 25 were tested the cells were not patched and one of the trap zones (P4-T1) did not work, but the trap zone P4-T2 worked well. After leak subtraction, a stable current sweep of about 2500 pA with a total rundown effect of about 17% (from 01 to C8) was obtained (see FIG. 9 and Table 3).

These exemplary results indicate that a stable current with no or minor rundown effect can be obtained using the hMYO-hERG cells even when the cells have gone through multiple passages.

6.5 Example 5: Evaluation of hERG Inhibitory Activities of Compounds with Fully Automated High Throughput System An evaluation of the hERG inhibitory activities with a compound with full automated high throughput patch clamp system was performed using the hMYO-hERG cells provide herein.

FIG. 10 shows the block of hERG tail current by compound "E-4031" in the hMYO-hERG cells. E-4031 (N-(4-(1-(2-(6-methylpyridin-2-yl)ethyl)piperidine-4-carbonyl) phenyl)methanesulfonamide) is a class Ill antiarrhythmic drug (see, e.g., Zhou et al. (1998) *Biophys. J.* 74: 230-41; Kim et al. (2005) *J. Appl. Physiol.* 98(4): 1469-1477).

FIG. 11 shows the block of hERG tail current by quinidine in the hMYO-hERG cells. Quinidine is known to have strong hERG inhibitory activity (e.g., strong hERG blocker; see, e.g., Vincente et al. (2015) *J Am Heart Assoc.* 4(4): 1-13).

hERG currents were evoked by using standard voltage command used in conventional patch clamping as described above (see Example 4; see also FIG. 6) with some modifications. Currents were recorded at different concentrations of E-4031 (FIG. 10) and quinidine (FIG. 11). As may be seen from the figures, for normalized hERG current sweeps at 37° C. temperature, hERG expression is robust, exhibiting a mean tail current amplitude of ~3700 pA for E-4031 and ~2700 pA for quinidine.

6.6 Example 6: Evaluation of hERG Inhibitory Activities of Additional Compounds with Fully Automated High Throughput System An evaluation of hERG inhibitory activities of additional compounds with full automated high throughout patch clamp system is performed using the hMYO-hERG cells as provided herein.

hERG currents are measured in the same manner as described in Examples 4 and 5. With respect to the inhibitory activities of compounds against hERG channels, inhibition ratios are calculated from the ratios of the peak value of the tail current after the addition of various concentrations of the compound, taking the peak value of the tail current recorded before the addition of the relevant compound as 100%. From the inhibition ratios of compounds at individual concentrations, hERG current inhibitory activity values ($IC_{50}$) are calculated.

Each compound is evaluated at the following concentrations, for example, at 0.01-30 µM. The drugs are allowed to act for about 3-15 minutes.

In the study, certain compounds that are already known to block hERG channels or not block hERG channels when studied by standard patch clamp can be used as positive or negative controls.

In one exemplary study, each compound is used in eight patch plate wells, generally allowing between three and eight successful cells (data points) at the one concentration. During the screen, each compound concentration is screened twice or more to ensure a sufficient number of cells per data point.

6.7 Example 7: Evaluation of Cell Viability

An evaluation of the activity of compound to reduce cell viability was performed using the hMYO-hERG cell line as provided herein. Certain compounds that are already known to inhibit or not inhibit hERG activity were analyzed.

Ninety-six (96) well plate(s) were seeded with hMYO-hERG cells containing approximately $1 \times 10^4$ cells/well. The plates were first incubated for 24 hours at 37° C., 5% $CO_2$, followed by incubation for 48 hours at 28° C., 5% $CO_2$. The wells were then treated with compound(s) of interest for 48 hours at standard cell cultural conditions. A negative control medium without cells was included to determine background signal.

The cells were then assayed for toxicity using a SetuBlue™ Cell Proliferation Assay Kit (Fluorometric) (Biolntersect, Catalog # F6009-2500-A). This kit uses a Blue indicator dye, Resazurin, to measure the metabolic capacity of cells. Resazurin is a non-fluorescent, cell permeable and non-toxic compound. Viable cells efficiently reduce the Blue indicator dye to resorufin, which is highly fluorescent and an indicator of cell viability. Nonviable or dead cells rapidly lose metabolic capacity and are unable to reduce the indicator dye, and thus do not generate a fluorescent signal.

The SetuBlue cell proliferation assay was performed as follows. The old media was aspirated and replaced with fresh 100 µl medium containing 10% volume of SetuBlue reagent containing the Blue indicator dye. The plates were incubated using standard cultural conditions for 1-4 hrs. The plates were than shaken for 10-20 seconds before recording fluorescence at 530/590 nm in PerkinElmer EnSpire® multimode plate reader. The relative fluorescence unit ("RFU") value of each control well was subtracted from all RFU value to yield corrected RFU values. The corrected RFU values at 530/590 nm (Y axis, $Log_{10}$ scale) were plotted against concentration of test compound (X axis). The $CC_{50}$ value were determined by locating the X-axis value corresponding to one-half the maximum(plateau) RFU value using GraphPad Prism software.

FIG. 12A shows the results from one representative experiment, where corrected RFU Values at 530/590 nm (Y axis, $Log_{10}$ scale)±SEM is plotted against drug concentration (in µM). As shown in this figure, doxorubicin, which exhibits long-term cardiotoxicity but only slight effects on hERG (see, e.g., Ducroq et al. (2010) *British Journal of Pharmacology* 159: 93-101; Moulin et al. (2015) *Circ Heart Fail.* 8(1): 98-108; Guo et al. (2015) *Curr Protoc Chem Biol.* 7(3): 141-85; Maillet et al. (2016) *Sci Rep.* 4(6): 25333)) is cardiotoxic on the hMYO-hERG cell line at concentrations above 50 µM. The $CC_{50}$ value for doxorubicin was determined to be 42.32 µM (see FIG. 12B). In contrast, quinidine, known to be a strong hERG blocker (see, e.g., Vincente et al. (2015) *J Am Heart Assoc.* 4(4): 1-13), is shown to be not significantly cardiotoxic on the hMYO-hERG cells at concentrations as high as 400 µM (compare to the control vehicle at 400 µM).

These results indicate that the hMYO-hERG cell line as provided herein can be used to evaluate cardiotoxicity, independent of hERG blockage.

6.8 Example 8: Stable Cell Line Preparation

Cardiomyocytes expressing hERG were prepared by transducing cells as described in Example 2 from AC10 adult human ventricular cardiomyocytes (ATCC Cat. No. PTA-1501), referred to herein as hMYO cells, with the pseudovirus particles generated in Example 1 containing an expression vector that expresses a C-terminal FLAG-tagged hERG. This expression vector also contains a bicistronic eGFP reporter gene and confers puromycin resistance for positive selection and maintenance, The cultured hMYO cells, were transduced at passage P3 and recombinant cardiomyocytes overexpressing hERG were generated. The recombinant cardiomyocytes stably expressing hERG were cultured through multiple passages to generate a stable cell line, which was deposited with the ATCC at passage P11. The deposited recombinant cardiomyocyte cell line was designated as ATCC Designation No. PTA-123324. After deposit, the passage P11 recombinant cardiomyocytes were designated P1 and further cultured in multiple passages for further cell line stability assessment. In subsequent passages, between passages P4 to P10, the recombinant cardiomyocytes were sorted several times for high GFP expression and kept under high puromycin (up to 50 µg/ml) selection media. In subsequent passages, after P10, the recombinant cardiomyocytes were tested up to passage P25 under drug selection (10 µg/ml). These passaged recombinant cardiomyocytes produced high stable hERG currents with an automated patch clamp machine. The deposited cells and subsequent passaged cells were stable in their hERG expression and the stable cells lines were useful in screening methods as disclosed herein.

While this specification contains many specifics, these should not be construed as limitations on the scope or of what may be claimed, but rather as descriptions of features specific to particular embodiments. Certain features that are described in this specification in the context or separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Thus, particular embodiments have been described. Other embodiments are within the scope of the following claims. For example, the actions recited in the claims can be performed in a different order and still achieve desirable results.

All publications and patent applications cited in this specification are herein incorporated by reference as if each individual publication or patent application were specifically and individually indicated to be incorporated by reference. Although the foregoing has been described in some detail by way of illustration and example for purposes of clarity of understanding, it will be readily apparent to those of ordinary skill in the art in light of the teachings of the specification that certain changes and modifications may be made thereto without departing from the spirit or scope of the appended claims.

---

What is claimed is:

1. A recombinant cell line comprising recombinant cardiomyocytes stably expressing human Ether-a-go-go Related Gene (hERG) potassium ion channel, wherein hERG comprises an amino acid sequence as set forth in amino acids 1-1159 of SEQ ID NO: 1, wherein the recombinant cardiomyocytes comprise a transduced nucleic acid sequence encoding hERG, wherein the cell line is designated hMYO-hERG (ATCC Designation No. PTA-123324).

2. The recombinant cell line of claim 1, wherein the recombinant cardiomyocytes are progeny, descendants or derivatives of hMYO-hERG (ATCC Designation No. PTA-123324).

3. An in vitro method of preparing the cell line according to claim 1, comprising:
   transducing human cardiomyocytes with a nucleic acid sequence encoding hERG; and
   selecting the cardiomyocytes stably expressing hERG.

4. The method of claim 3, wherein the transducing is with a vector comprising the nucleic acid sequence.

5. The method of claim 4, wherein the vector is a retroviral vector.

6. The method of claim 5, wherein the vector is a lentiviral vector.

7. The method of claim 6, further comprising generating pseudo-lentiviral particles.

8. A kit comprising the recombinant cardiomyocytes from the cell line of claim 1.

9. A stable cardiomyocyte cell line overexpressing hERG comprising recombinant cardiomyocytes that are progeny, descendants or derivatives of hMYO-hERG (ATCC Designation No. PTA-123324), wherein the recombinant cardiomyocytes comprise a transduced nucleic acid sequence encoding hERG, wherein the cell line is designated hMYO-hERG (ATCC Designation No. PTA-123324).

* * * * *

SEQUENCE LISTING

<160> NUMBER OF SEQ ID NOS: 2

<210> SEQ ID NO 1
<211> LENGTH: 1185
<212> TYPE: PRT
<213> ORGANISM: Artificial Sequence
<220> FEATURE:
<223> OTHER INFORMATION: Synthetic construct

<400> SEQUENCE: 1

Met Pro Val Arg Arg Gly His Val Ala Pro Gln Asn Thr Phe Leu Asp
1               5                   10                  15

Thr Ile Ile Arg Lys Phe Glu Gly Gln Ser Arg Lys Phe Ile Ile Ala
            20                  25                  30

Asn Ala Arg Val Glu Asn Cys Ala Val Ile Tyr Cys Asn Asp Gly Phe
        35                  40                  45

Cys Glu Leu Cys Gly Tyr Ser Arg Ala Glu Val Met Gln Arg Pro Cys
    50                  55                  60

Thr Cys Asp Phe Leu His Gly Pro Arg Thr Gln Arg Arg Ala Ala Ala
65                  70                  75                  80

Gln Ile Ala Gln Ala Leu Leu Gly Ala Glu Glu Arg Lys Val Glu Ile

```
            85                  90                  95
Ala Phe Tyr Arg Lys Asp Gly Ser Cys Phe Leu Cys Leu Val Asp Val
            100                 105                 110

Val Pro Val Lys Asn Glu Asp Gly Ala Val Ile Met Phe Ile Leu Asn
            115                 120                 125

Phe Glu Val Val Met Glu Lys Asp Met Val Gly Ser Pro Ala His Asp
130                 135                 140

Thr Asn His Arg Gly Pro Pro Thr Ser Trp Leu Ala Pro Gly Arg Ala
145                 150                 155                 160

Lys Thr Phe Arg Leu Lys Leu Pro Ala Leu Leu Ala Leu Thr Ala Arg
                165                 170                 175

Glu Ser Ser Val Arg Ser Gly Ala Gly Ala Gly Ala Pro Gly
            180                 185                 190

Ala Val Val Val Asp Val Asp Leu Thr Pro Ala Ala Pro Ser Ser Glu
            195                 200                 205

Ser Leu Ala Leu Asp Glu Val Thr Ala Met Asp Asn His Val Ala Gly
            210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
                245                 250                 255

Asn Pro Asp Ala Ser Gly Ser Ser Cys Ser Leu Ala Arg Thr Arg Ser
            260                 265                 270

Arg Glu Ser Cys Ala Ser Val Arg Arg Ala Ser Ser Ala Asp Asp Ile
            275                 280                 285

Glu Ala Met Arg Ala Gly Val Leu Pro Pro Pro Arg His Ala Ser
290                 295                 300

Thr Gly Ala Met His Pro Leu Arg Ser Gly Leu Leu Asn Ser Thr Ser
305                 310                 315                 320

Asp Ser Asp Leu Val Arg Tyr Arg Thr Ile Ser Lys Ile Pro Gln Ile
                325                 330                 335

Thr Leu Asn Phe Val Asp Leu Lys Gly Asp Pro Phe Leu Ala Ser Pro
            340                 345                 350

Thr Ser Asp Arg Glu Ile Ile Ala Pro Lys Ile Lys Glu Arg Thr His
            355                 360                 365

Asn Val Thr Glu Lys Val Thr Gln Val Leu Ser Leu Gly Ala Asp Val
            370                 375                 380

Leu Pro Glu Tyr Lys Leu Gln Ala Pro Arg Ile His Arg Trp Thr Ile
385                 390                 395                 400

Leu His Tyr Ser Pro Phe Lys Ala Val Trp Asp Trp Leu Ile Leu Leu
                405                 410                 415

Leu Val Ile Tyr Thr Ala Val Phe Thr Pro Tyr Ser Ala Ala Phe Leu
            420                 425                 430

Leu Lys Glu Thr Glu Glu Gly Pro Pro Ala Thr Glu Cys Gly Tyr Ala
            435                 440                 445

Cys Gln Pro Leu Ala Val Val Asp Leu Ile Val Asp Ile Met Phe Ile
            450                 455                 460

Val Asp Ile Leu Ile Asn Phe Arg Thr Thr Tyr Val Asn Ala Asn Glu
465                 470                 475                 480

Glu Val Val Ser His Pro Gly Arg Ile Ala Val His Tyr Phe Lys Gly
                485                 490                 495

Trp Phe Leu Ile Asp Met Val Ala Ala Ile Pro Phe Asp Leu Leu Ile
            500                 505                 510
```

```
Phe Gly Ser Gly Ser Glu Glu Leu Ile Gly Leu Leu Lys Thr Ala Arg
            515                 520                 525

Leu Leu Arg Leu Val Arg Val Ala Arg Lys Leu Asp Arg Tyr Ser Glu
        530                 535                 540

Tyr Gly Ala Ala Val Leu Phe Leu Leu Met Cys Thr Phe Ala Leu Ile
545                 550                 555                 560

Ala His Trp Leu Ala Cys Ile Trp Tyr Ala Ile Gly Asn Met Glu Gln
                565                 570                 575

Pro His Met Asp Ser Arg Ile Gly Trp Leu His Asn Leu Gly Asp Gln
            580                 585                 590

Ile Gly Lys Pro Tyr Asn Ser Ser Gly Leu Gly Gly Pro Ser Ile Lys
        595                 600                 605

Asp Lys Tyr Val Thr Ala Leu Tyr Phe Thr Phe Ser Ser Leu Thr Ser
    610                 615                 620

Val Gly Phe Gly Asn Val Ser Pro Asn Thr Asn Ser Glu Lys Ile Phe
625                 630                 635                 640

Ser Ile Cys Val Met Leu Ile Gly Ser Leu Met Tyr Ala Ser Ile Phe
                645                 650                 655

Gly Asn Val Ser Ala Ile Ile Gln Arg Leu Tyr Ser Gly Thr Ala Arg
            660                 665                 670

Tyr His Thr Gln Met Leu Arg Val Arg Glu Phe Ile Arg Phe His Gln
    675                 680                 685

Ile Pro Asn Pro Leu Arg Gln Arg Leu Glu Glu Tyr Phe Gln His Ala
690                 695                 700

Trp Ser Tyr Thr Asn Gly Ile Asp Met Asn Ala Val Leu Lys Gly Phe
705                 710                 715                 720

Pro Glu Cys Leu Gln Ala Asp Ile Cys Leu His Leu Asn Arg Ser Leu
                725                 730                 735

Leu Gln His Cys Lys Pro Phe Arg Gly Ala Thr Lys Gly Cys Leu Arg
            740                 745                 750

Ala Leu Ala Met Lys Phe Lys Thr Thr His Ala Pro Pro Gly Asp Thr
        755                 760                 765

Leu Val His Ala Gly Asp Leu Leu Thr Ala Leu Tyr Phe Ile Ser Arg
    770                 775                 780

Gly Ser Ile Glu Ile Leu Arg Gly Asp Val Val Ala Ile Leu Gly
785                 790                 795                 800

Lys Asn Asp Ile Phe Gly Glu Pro Leu Asn Leu Tyr Ala Arg Pro Gly
                805                 810                 815

Lys Ser Asn Gly Asp Val Arg Ala Leu Thr Tyr Cys Asp Leu His Lys
            820                 825                 830

Ile His Arg Asp Asp Leu Leu Glu Val Leu Asp Met Tyr Pro Glu Phe
        835                 840                 845

Ser Asp His Phe Trp Ser Ser Leu Glu Ile Thr Phe Asn Leu Arg Asp
    850                 855                 860

Thr Asn Met Ile Pro Gly Ser Pro Gly Ser Thr Glu Leu Glu Gly Gly
865                 870                 875                 880

Phe Ser Arg Gln Arg Lys Arg Lys Leu Ser Phe Arg Arg Thr Asp
                885                 890                 895

Lys Asp Thr Glu Gln Pro Gly Glu Val Ser Ala Leu Gly Pro Gly Arg
            900                 905                 910

Ala Gly Ala Gly Pro Ser Ser Arg Gly Arg Pro Gly Gly Pro Trp Gly
        915                 920                 925
```

Glu Ser Pro Ser Ser Gly Pro Ser Ser Pro Glu Ser Ser Glu Asp Glu
            930                 935                 940

Gly Pro Gly Arg Ser Ser Pro Leu Arg Leu Val Pro Phe Ser Ser
945                 950                 955                 960

Pro Arg Pro Pro Gly Glu Pro Gly Gly Glu Pro Leu Met Glu Asp
                965                 970                 975

Cys Glu Lys Ser Ser Asp Thr Cys Asn Pro Leu Ser Gly Ala Phe Ser
            980                 985                 990

Gly Val Ser Asn Ile Phe Ser Phe Trp Gly Asp Ser Arg Gly Arg Gln
            995                 1000                1005

Tyr Gln Glu Leu Pro Arg Cys Pro Ala Pro Thr Pro Ser Leu Leu
    1010                1015                1020

Asn Ile Pro Leu Ser Ser Pro Gly Arg Arg Pro Arg Gly Asp Val
    1025                1030                1035

Glu Ser Arg Leu Asp Ala Leu Gln Arg Gln Leu Asn Arg Leu Glu
    1040                1045                1050

Thr Arg Leu Ser Ala Asp Met Ala Thr Val Leu Gln Leu Leu Gln
    1055                1060                1065

Arg Gln Met Thr Leu Val Pro Pro Ala Tyr Ser Ala Val Thr Thr
    1070                1075                1080

Pro Gly Pro Gly Pro Thr Ser Thr Ser Pro Leu Leu Pro Val Ser
    1085                1090                1095

Pro Leu Pro Thr Leu Thr Leu Asp Ser Leu Ser Gln Val Ser Gln
    1100                1105                1110

Phe Met Ala Cys Glu Glu Leu Pro Pro Gly Ala Pro Glu Leu Pro
    1115                1120                1125

Gln Glu Gly Pro Thr Arg Arg Leu Ser Leu Pro Gly Gln Leu Gly
    1130                1135                1140

Ala Leu Thr Ser Gln Pro Leu His Arg His Gly Ser Asp Pro Gly
    1145                1150                1155

Ser Tyr Leu Glu Cys Gly Arg Asn Pro Ala Phe Leu Tyr Lys Val
    1160                1165                1170

Val Leu Glu Met Asp Tyr Lys Asp Asp Asp Asp Lys
    1175                1180                1185

<210> SEQ ID NO 2
<211> LENGTH: 3557
<212> TYPE: DNA
<213> ORGANISM: Artificial Sequence
<220> FEATURE:
<223> OTHER INFORMATION: Synthetic construct

<400> SEQUENCE: 2
atgccggtgc ggaggggcca cgtcgcgccg cagaacacct tcctggacac catcatccgc      60
aagtttgagg ccagagccg taagttcatc atcgccaacg ctcgggtgga gaactgcgcc     120
gtcatctact gcaacgacgg cttctgcgag ctgtgcggct actcgcgggc cgaggtgatg     180
cagcgaccct gcacctgcga cttcctgcac gggccgcgca cgcagcgccg cgctgccgcg     240
cagatcgcgc aggcactgct gggcgccgag gagcgcaaag tggaaatcgc cttctaccgg     300
aaagatggga gctgcttcct atgtctggtg gatgtggtgc ccgtgaagaa cgaggatggg     360
gctgtcatca tgttcatcct caatttcgag gtggtgatgg agaaggacat ggtggggtcc     420
ccggctcatg acaccaacca ccggggcccc ccaccagct ggctggcccc aggccgcgcc     480
aagaccttcc gcctgaagct gcccgcgctg ctggcgctga cggccggga gtcgtcggtg     540

```
cggtcgggcg gcgcgggcgg cgcgggcgcc ccggggggccg tggtggtgga cgtggacctg    600
acgcccgcgg cacccagcag cgagtcgctg gccctggacg aagtgacagc catggacaac    660
cacgtggcag ggctcgggcc cgcggaggag cggcgtgcgc tggtgggtcc cggctctccg    720
ccccgcagcg cgcctggcca gctcccatcg ccccgggcgc acagcctcaa ccccgacgcc    780
tcgggctcca gctgcagcct ggcccggacg cgctcccgag aaagctgcgc cagcgtgcgc    840
cgcgcctcgt cggccgacga catcgaggcc atgcgcgccg gggtgctgcc ccgccaccg     900 cgccacgcca gcaccggggc catgcaccca ctgcgcagcg gcttgctcaa ctccacctcg    960
gactccgacc tcgtgcgcta ccgcaccatt agcaagattc cccaaatcac cctcaacttt   1020
gtggacctca agggcgaccc cttcttggct tcgcccacca gtgaccgtga gatcatagca   1080
cctaagataa aggagcgaac ccacaatgtc actgagaagg tcacccaggt cctgtccctg   1140
ggcgccgacg tgctgcctga gtacaagctg caggcaccgc gcatccaccg ctggaccatc   1200
ctgcattaca gccccttcaa ggccgtgtgg gactggctca tcctgctgct ggtcatctac   1260
acggctgtct tcacacccta ctcggctgcc ttcctgctga aggagacgga agaaggcccg   1320
cctgctaccg agtgtggcta cgcctgccag ccgctggctg tggtggacct catcgtggac   1380
atcatgttca ttgtggacat cctcatcaac ttccgcacca cctacgtcaa tgccaacgag   1440
gaggtggtca gccacccggg ccgcatcgcc gtccactact tcaagggctg gttcctcatc   1500
gacatggtgg ccgccatccc cttcgacctg ctcatcttcg gctctggctc tgaggagctg   1560
atcgggctgc tgaagactgc gcggctgctg cggctggtgc gcgtggcgcg gaagctggat   1620
cgctactcag agtacggcgc ggccgtgctg ttcttgctca tgtgcacctt tgcgctcatc   1680
gcgcactggc tagcctgcat ctggtacgcc atcggcaaca tggagcagcc acacatggac   1740
tcacgcatcg gctggctgca caacctgggc gaccagatag gcaaacccta caacagcagc   1800
ggcctgggcg gcccctccat caaggacaag tatgtgacgg cgctctactt caccttcagc   1860
agcctcacca gtgtgggctt cggcaacgtc tctcccaaca ccaactcaga gaagatcttc   1920
tccatctgcg tcatgctcat tggctcccctc atgtatgcta gcatcttcgg caacgtgtcg   1980
gccatcatcc agcggctgta ctcgggcaca gcccgctacc acacacagat gctgcgggtg   2040
cgggagttca tccgcttcca ccagatcccc aatccctgc gccagcgcct cgaggagtac   2100
ttccagcacg cctggtccta caccaacggc atcgacatga acgcggtgct gaagggcttc   2160
cctgagtgcc tgcaggctga catctgcctg cacctgaacc gctcactgct gcagcactgc   2220
aaacccttcc gaggggccac caagggctgc cttcgggccc tggccatgaa gttcaagacc   2280
acacatgcac cgccagggga cacactggtg catgctgggg acctgctcac cgccctgtac   2340
ttcatctccc ggggctccat cgagatcctg cggggcgacg tcgtcgtggc catcctgggg   2400
aagaatgaca tctttgggga gcctctgaac ctgtatgcaa ggcctggcaa gtcgaacggg   2460
gatgtgcggg ccctcaccta ctgtgaccta cacaagatcc atcggacga cctgctggag   2520 gtgctggaca tgtaccctga gttctccgac cacttctggt ccagcctgga gatcaccttc   2580
aacctgcgag ataccaacat gatcccgggc tcccccggca gtacggagtt agagggtggc   2640
ttcagtcggc aacgcaagcg caagttgtcc ttccgcaggc gcacggacaa ggacacggag   2700
cagccagggg aggtgtcggc cttggggccg ggccgggcgg gggcagggcc gagtagccgg   2760
ggccggccgg gggggccgtg gggggagagc ccgtccagtg gccccctccag ccctgagagc   2820 agtgaggatg agggccaagg ccgcagctcc agccccctcc gctggtgcc cttctccagc    2880 cccaggcccc ccggagagcc gccgggtggg gagcccctga tggaggactg cgagaagagc   2940
```

```
agcgacactt gcaacccct gtcaggcgcc ttctcaggag tgtccaacat tttcagcttc      3000 tgggggaca gtcggggccg ccagtaccag gagctccctc gatgcccgc ccccacccc        3060 agcctcctca acatccccct ctccagcccg ggtcggcggc cccggggcga cgtggagagc    3120
aggctggatg ccctccagcg ccagctcaac aggctggaga cccggctgag tgcagacatg    3180
gccactgtcc tgcagctgct acagaggcag atgacgctgg tcccgcccgc ctacagtgct    3240
gtgaccaccc cggggcctgg ccccacttcc acatccccgc tgttgcccgt cagcccctc     3300 cccaccctca ccttggactc gctttctcag gtttcccagt tcatggcgtg tgaggagctg    3360 cccccgggg cccagagct tccccaagaa ggccccacac gacgcctctc cctaccgggc      3420
cagctggggg ccctcacctc ccagcccctg cacagacacg gctcggaccc gggcagttac    3480
ctcgagtgcg gccgcaaccc agctttcttg tacaaagtgg ttctcgagat ggactacaaa    3540
gacgatgacg acaagta                                                   3557
```